(12) United States Patent
Casuscelli et al.

(10) Patent No.: US 9,284,298 B2
(45) Date of Patent: Mar. 15, 2016

(54) PYRAZOLYL-PYRIMIDINE DERIVATIVES AS KINASE INHIBITORS

(75) Inventors: Francesco Casuscelli, Dairago (IT);
Maria Gabriella Brasca, Nerviano (IT);
Marina Caldarelli, Milan (IT);
Giovanni Cervi, Como (IT); Teresa Disingrini, Vanzago (IT); Francesca Quartieri, Arona (IT)

(73) Assignee: NERVIANO MEDICAL SCIENCES S.R.L., Nerviano (MI) (IT)

(*) Notice: Subject to any disclaimer, the term of this patent is extended or adjusted under 35 U.S.C. 154(b) by 52 days.

(21) Appl. No.: 14/110,596

(22) PCT Filed: Apr. 3, 2012

(86) PCT No.: PCT/EP2012/056047
§ 371 (c)(1),
(2), (4) Date: Oct. 8, 2013

(87) PCT Pub. No.: WO2012/139930
PCT Pub. Date: Oct. 18, 2012

(65) Prior Publication Data
US 2014/0051708 A1 Feb. 20, 2014

(30) Foreign Application Priority Data
Apr. 11, 2011 (EP) .................................. 11161925

(51) Int. Cl.
| | | |
|---|---|---|
| *A61K 45/06* | (2006.01) | |
| *A61K 31/506* | (2006.01) | |
| *C07D 403/04* | (2006.01) | |
| *C07D 401/14* | (2006.01) | |
| *C07D 403/14* | (2006.01) | |
| *C07D 413/14* | (2006.01) | |

(52) U.S. Cl.
CPC ............ *C07D 403/04* (2013.01); *A61K 31/506* (2013.01); *A61K 45/06* (2013.01); *C07D 401/14* (2013.01); *C07D 403/14* (2013.01); *C07D 413/14* (2013.01)

(58) Field of Classification Search
CPC .... C07D 403/04; C07D 401/14; A61K 45/06; A61K 31/506
USPC ............. 514/252.19, 275, 256, 274; 435/188; 544/331, 295, 333, 316
See application file for complete search history.

(56) References Cited

FOREIGN PATENT DOCUMENTS

| | | | |
|---|---|---|---|
| EP | 1 785 418 A1 | 5/2007 | |
| WO | WO 2005/014572 A1 | 2/2005 | |
| WO | WO 2005/063737 A1 | 7/2005 | |
| WO | WO 2006/014005 A1 | 2/2006 | |
| WO | WO 2006/071644 A1 | 7/2006 | |
| WO | WO 2007/110344 A1 | 10/2007 | |
| WO | WO 2009/156315 A1 | 12/2009 | |

OTHER PUBLICATIONS

International Search Report dated Aug. 9, 2012 issued in PCT/EP2012/056047.
Alvarez J.V. et al., "Signal Transducer and Activator of Transcription 3 is Required for the Oncogenic Effects of Non-Small-Cell Lung Cancer-Associated Mutations of the Epidermal Growth Factor Receptor", Cancer Research 66 (6):3162-3168 (Mar. 15, 2006).
Amaravadi R. et al., "The Survival Kinases Akt and Pim as Potential Pharmacological Targets", The Journal of Clinical Investigation 115(10):2618-2624 (Oct. 2005).
Ara T. et al., "Interleukin-6 in Bone Metastasis and Cancer Progression", Eur. J. Cancer 46(7):1223-1231 (May 2010).
Baker SJ et al., "Hematopoietic Cytokine Receptor Signaling", Oncogene 26:6724-6737 (2007).
Baxter E.J. et al., "Acquired Mutation of the Tyrosine Kinase JAK2 in Human Myeloproliferative Disorders", Lancet 365:1054-1061 (Mar. 19, 2005).
Bertheau P. et al., "Exquisite Sensitivity of TP53 Mutant and Basal Breast Cancers to a Dose-Dense Epirubicin-Cyclophosphamide Regimen", PLoS Medicine 4(3):0585-0594 (Mar. 2007).
Brault L. et al., "PIM Serine/Threonine Kinases in the Pathogenesis and Therapy of Hematologic Malignancies and Solid Cancers", Haematologica 95(6):1004-1015 (2010).
Bullock A.N. et al., "Structure and Substrate Specificity of the Pim-1 Kinase", The Journal of Biological Chemistry 280(50):41675-41682 (Dec. 16, 2005).
Campbell P.J. et al., "Mechanisms of Disease—The Myeloproliferative Disorders", The New England Journal of Medicine 355:2452-2466 (Dec. 7, 2006).
Carter S.L. et al., "A Signature of Chromosomal Instability Inferred from Gene Expression Profiles Predicts Clinical Outcome in Multiple Human Cancers", Nature Genetics 38(9):1043-1048 (Sep. 2006).
Chan D.M.T. et al., "New N- and O-Arylations with Phenylboronic Acids and Cupric Acetate", Tetrahedron Letters 39:2933-2936 (1998).
Choudhary C. et al., "Mislocalized Activation of Oncogenic RTKs Switches Downstream Signaling Outcomes", Molecular Cell 36:326-339 (Oct. 23, 2009).
Clevenger C.V., "Roles and Regulation of Stat Family Transcription Factors in Human Breast Cancer", American Journal of Pathology 165(5):1449-1460 (Nov. 2004).

(Continued)

*Primary Examiner* — James O Wilson
*Assistant Examiner* — Ebenezer O Sackey
(74) *Attorney, Agent, or Firm* — Scully, Scott, Murphy & Presser, P.C.

(57) ABSTRACT

The present invention relates to pyrazolyl-pyrimidine derivatives which modulate the activity of protein kinases and are therefore useful in treating diseases caused by dysregulated protein kinase activity. The present invention also provides methods for preparing these compounds, pharmaceutical compositions comprising these compounds, and methods of treating diseases utilizing such compounds or the pharmaceutical compositions containing them.

9 Claims, No Drawings

(56) References Cited

OTHER PUBLICATIONS

Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
Cohen P., "Protein Kinases—The Major Drug Targets of the Twenty-First Century?", Nature Reviews—Drug Discovery 1:309-315 (Apr. 2002).
Cohen P., "The Development and Therapeutic Potential of Protein Kinase Inhibitors", Current Opinion in Chemical Biology 3:459-465 (1999).
Cohen A.M. et al., "Increased Expression of the hPim-2 Gene in Human Chronic Lymphocytic Leukemia and Non-Hodgkin Lymphoma", Leukemia & Lymphoma 45(5):951-955 (May 2004).
Constantinescu S.N. et al., "Mining for JAK-STAT Mutations in Cancer", Trends in Biochemical Sciences 33 (3):122-131 (2008).
De Carcer G. et al., "Targeting Cell Cycle Kinases for Cancer Therapy", Current Medicinal Chemistry 14:969-985 (2007).
Deng X. et al., "An Efficient Route to 4-Aryl-5-Pyrimidinylimidazoles Via Sequential Functionalization of 2,4-Dichloropyrimidine", Organic Letters 8(2):269-272 (2006).
Ghoreschi K. et al., "Janus Kinases in Immune Cell Signaling", Immunol Rev. 228(1):273-287 (Mar. 2009).
Hercus T.R. et al., "The Granulocyte-Macrophage Colony-Stimulating Factor Receptor: Linking its Structure to Cell Signaling and its Role in Disease", Blood 114(7):1289-1298 (Aug. 13, 2009).
Huttmann A. et al., "Gene Expression Signatures Separate B-Cell Chronic Lymphocytic Leukaemia Prognostic Subgroups Defined by ZAP-70 and CD38 Expression Status", Leukemia 20:1774-1782 (2006).
Ihle J.N., "Cytokine Receptor Signalling", Nature 377:591-594 (Oct. 19, 1995).
James C. et al., "A Unique Clonal JAK2 Mutation Leading to Constitutive Signalling Causes Polycythaemia Vera", Nature 434:1144-1148 (Apr. 28, 2005).
Jelluma N. et al., "Chromosomal Instability by Inefficient Mps1 Auto-Activation Due to a Weakened Mitotic Checkpoint and Lagging Chromosomes", PLoS One 3(6):e2415 (8 pages) (Jun. 2008).
Jelluma N. et al., "Mps1 Phosphorylates Borealin to Control Aurora B Activity and Chromosomes Alignment", Cell 132:233-246 (Jan. 25, 2008).
Jeong E.G. et al., "Somatic Mutations of JAK1 and JAK3 in Acute Leukemias and Solid Cancers", Clin Cancer Research 14(12):3716-3721 (Jun. 15, 2008).
Jiang N. et al., "Novel 1,3-Dipolar Cycloaddition of Diazocarbonyl Compounds to Alkynes Catalyzed by InC13 in Water", Chem. Commun. 394-395 (2004).
Jones M.H. et al., "Chemical Genetics Reveals a Role for Mps1 Kinase in Kinetochore Attachment During Mitosis", Current Biology 15:160-165 (Jan. 26, 2005).
Kim K-T et al., "Pim-1 is Up-Regulated by Constitutively Activated FLT3 and Plays a Role in FLT3-Mediated Cell Survival", Blood 105(4):1759-1767 (Feb. 15, 2005).
Kops G.J.P.L. et al., "On the Road to Cancer: Aneuploidy and the Mitotic Checkpoint", Nature Reviews—Cancer 5:773-785 (Oct. 2005).
Kralovics R. et al., "A Gain-of-Function Mutation of JAK2 in Myleloproliferative Disorders", The New England Journal of Medicine 352(17):1779-1790 (Apr. 28, 2005).
Kumar A. et al., "Crystal Structures of Proto-Oncogene Kinase Pim1: A Target of Aberrant Somatic Hypermutations in Diffuse Large Cell Lymphoma", J. Mol. Biol. 348:183-193 (2005).

Lacronique V. et al., "A TEL-JAK2 Fusion Protein with Constitutive Kinase Activity in Human Leukemia", Science 278:1309-1312 (Nov. 14, 1997).
Lam P.Y.S. et al., "New Aryl/Heteroaryl C-N Bond Cross-Coupling Reactions Via Arylboronic Acid/Cupric Acetate Arylation", Tetrahedron Letters 39:2941-2944 (1998).
Leonard W.J. et al., "JAKs and STATs: Biological Implications", Annu. Rev. Immunol. 16:293-322 (1998).
Levine R.L. et al., "Activating Mutation in the Tyrosine Kinase JAK2 in Polycythemia Vera, Essential Thrombocythemia, and Myeloid Metaplasia with Myelofibrosis", Cancer Cell 7:387-397(Apr. 2005).
Ma Y. et al., "Expression of Targeting Protein for Xklp2 Associated with Both Malignant Transformation of Respiratory Epithelium and Progression of Squamous Cell Lung Cancer", Clin Cancer Res. 12(4):1121-1127 (Feb. 15, 2006).
Murray P.J., "The JAK-STAT Signaling Pathway: Input and Output Integration", The Journal of Immunology 178:2623-2629 (2007).
Musacchio A. et al., "The Spindle-Assembly Checkpoint in Space and Time", Nature Reviews—Molecular Cell Biology 8:379-393 (May 2007).
Roodman G.D., "New Potential Targets for Treating Myeloma Bone Disease", Clin Cancer Res. 12(20 Suppl):6270s-6273s (Oct. 15, 2006).
Sayyah J. et al., "Jak2 Inhibitors: Rationale and Role as Therapeutic Agents in Hematologic Malignancies", Curr Oncol Rep. 11(2):117-124 (Mar. 2009).
Schmidt M. et al., "Ablation of the Spindle Assembly Checkpoint by a Compound Targeting Mps1", European Molecular Biology Organization Reports 6(9):866-872 (2005).
Shah N. et al., "Potential Roles for the PIMI1 Kinase in Human Cancer—A Molecular and Therapeutic Appraisal", European Journal of Cancer 44:2144-2151 (2008).
Shide K. et al., "Development of ET, Primary Myelofibrosis and PV in Mice Expressing JAK2 V617F", Leukemia 22:87-95 (2008).
Silver J.S. et al., "GP130 at the Nexus of Inflammation, Autoimmunity, and Cancer", Journal of Leukocyte Biology 88:1145-1156 (Dec. 2010).
Spivak J.L., "Animal Models of the MPD: Lack of the Clones", Blood 108(5):1427-1428 (Sep. 1, 2006).
Stucke V.M. et al., "Human Mps1 Kinase is Required for the Spindle Assembly Checkpoint But Not for Centrosome Duplication", The European Molecular Biology Organization 21(7):1723-1732 (2002).
Tamburini J. et al., "Protein Synthesis is Resistant to Rapamycin and Constitutes a Promising Therapeutic Target in Acute Myeloid Leukemia", Blood 114(8):1618-1627 (Aug. 20, 2009).
Tavares F.X. et al., "N-Phenyl-4-Pyrazolo[1,5-b]Pyridazin-3-Ylpyrimidin-2-Amines as Potent and Selective Inhibitors of Glycogen Synthase Kinase 3 with Good Cellular Efficacy", J. Med. Chem. 47:4716-4730 (2004).
Tighe A. et al., "Mps1 Kinase Activity Restrains Anaphase During an Unperturbed Mitosis and Targets Mad2 to Kinetochores", J. Cell Biol. 181(6):893-901 (2008).
Velculescu V.E., "Defining the Blueprint of the Cancer Genome", Carcinogenesis 29(6):1087-1091 (2008).
Wallace T.A. et al., "Jak2 Tyrosine Kinase", Cell Biochemistry and Biophysics 44:213-222 (2006).
Weaver B.A.A. et al., "Aneuploidy Acts Both Oncogenically and as a Tumor Suppressor", Cancer Cell 11:25-36 (Jan. 2007).
Weiss E. et al., "The *Saccharomyces cerevisiae* Spindle Pole Body Duplication Gene MPS1 is Part of a Mitotic Checkpoint", The Journal of Cell Biology 132(1&2):111-123 (Jan. 1996).
Weissman S.A. et al., "Ligand-Free Palladium-Catalyzed Cyanation of Aryl Halides", J. Org. Chem. 70:1508-1510 (2005).
Winey M. et al., "MPS1 and MPS2: Novel Yeast Genes Defining Distinct Steps of Spindle Pole Body Duplication", The Journal of Cell Biology 114(4):745-754 (Aug. 1991).
Yeung P.Y. et al., "A Mild and Efficient Palladium-Catalyzed Cyanation of Aryl Chlorides with K4[Fe(CN)6]", Organic Letters 13(4):648-651 (Feb. 18, 2011).

PYRAZOLYL-PYRIMIDINE DERIVATIVES AS KINASE INHIBITORS

The present invention relates to pyrazolyl-pyrimidine derivatives, to a process for their preparation, to pharmaceutical compositions comprising them, and to their use as therapeutic agents, particularly in the treatment of diseases caused by dysregulated protein kinase activity, such as cancer, cell proliferative disorders, viral infections, immune disorders, neurodegenerative disorders and cardiovascular diseases.

INCORPORATION BY REFERENCE OF SEQUENCE LISTING

The Sequence Listing in an ASCII text file, named as 30427_SequenceListing.txt of 1 KB, created on Oct. 7, 2013, and submitted to the United States Patent and Trademark Office via EFS-Web, is incorporated herein by reference.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology, 1999, 3, 459-465; Nature Rev. Drug Discov. 2002; and Carcinogenesis, 2008, 29, 1087-1091.

Originally identified as activated genes by proviral mutagenesis in a lymphoma mouse model, PIMs (PIM1, PIM2 and/or PIM3 throughout this application) are protein-serine/threonine kinases. PIM kinases are poorly expressed in normal tissues, and overexpressed or even mutated in a discrete number of human cancers, including Lymphoma, Leukaemia, Prostate, Pancreas and Gastric cancers [Shah et al. Eur. J. Cancer, 44, 2144-51, (2008)].

PIM kinases are constitutively active and their activity supports in vitro and in vivo tumor cell growth and survival through modification of an increasing number of common as well as isoform-specific substrates including several cell cycle regulators and apoptosis mediators. PIM1, but not PIM2, seems also to mediate homing and migration of normal and malignant hematopoietic cells by regulating chemokine receptor surface expression [Brault et al. Haematologica, 95, 1004-1015 (2010)].

There is increasing evidence that PIM1 and PIM2 kinases may be involved in mediating the oncogenic effects of some acute myelogenous leukemias (AML)-associated oncogenes. In particular, the oncogenic role of FLT3-mutations (ITD and KD mut., present in 30% of AMLs) and/or translocations involving the MLL gene (occurring in 20% of AMLs) [Kumar, et al. J. Mol. Biol. 348, 183-193, (2005)]. PIM1 is more expressed in FLT3-ITD-transformed AML cells than in WT bone marrow cells. Data suggest that PIM1 as well as PIM2 inhibition may mediate FLT3-ITD-dependent death of AML cells. Interestingly, cells transformed by FLT3 mutations that confer resistance to small-molecule tyrosine kinase inhibitors were still sensitive to knockdown of PIM2, or PIM1 and PIM2, by RNAi [Kim et al., Blood, 105, 1759-67, (2005)].

Moreover, PIM2 has been reported being over-expressed and associated with progression of several malignancies that originate from the B-cell lineage such as chronic lymphocytic leukemia (CLL), diffuse large B-cell lymphoma (DLBCL), mantle cell lymphoma (MCL) or myeloma [Cohen et al. Leuk. Lymphoma, 94, 51, 2004, Huttmann et al. Leukemia, 20, 1774 (2006)].

Interestingly, PIM and AKT/PKB seem to play partly redundant roles in mediating growth and survival of hematopoietic cells, most probably due to overlapping substrates like BAD, p21WAF1/CIP1, p27KIP1, or Cot/Tp1-2 [Choudhary et al., Mol. Cell. 36, 326-39 (2009)].

PIM kinases have been shown to control mTOR inhibition (rapamycin) resistance, proliferation and survival. Therefore, a combination of small molecule inhibitors targeting several survival kinases might be essential for a powerful cancer therapeutic platform [Amaravadi R., et al. J. Clin. Invest. 2005, 115 (10), 2618-24]. Oncogenic protein synthesis through eIF4E binding protein 1 (4E-BP1) seems to be mTOR-independent and controlled by PIM2. This observations suggest that the oncogenic eIF4F translation-initiating complex could be blocked with small molecules PIM2 inhibitors [Tamburini J. et al. Blood 2009, 114 (8), 1718-27 and Brault L. et al. Haematologica 2010, 95 (6), 1004-1015].

The use of mitotic inhibitors in cancer therapy is a widely accepted clinical strategy for the treatment of a broad range of human cancers. Taxanes (paclitaxel and docetaxel) and vinca alkaloids (vincristine and vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types.

Several protein kinases play key roles in the orchestration of the cell cycle and some of them are already subject to targeted therapies in the oncology setting, including Cdk-2 and Aurora-A. The fidelity of mitosis is of paramount importance and several "checkpoints" exist in normal cells to maintain chromosome integrity during the cell cycle.

The Spindle Assembly Checkpoint (SAC) is specifically required for proper chromosomal segregation into the two daughter cells upon cellular division. It ensures that sister chromatids aligned at the metaphase plate do not separate prior to the bipolar attachment of all duplicated chromosomes to the mitotic spindle (reviewed in Musacchio A. and Salmon E. D., Nat Rev Mol Cell Biol, 8(5): 379-93, May 2007).

Even a single un-aligned chromosome is sufficient to trigger the SAC signal, it is a tightly regulated pathway that ultimately results into the inhibition of the anaphase promoting complex/cyclosome (APC/C)-mediated polyubiquitylation and degradation of two key mitotic components: cyclin B1 and Securin. Securin specifically is required to get sister chromatids separation and anaphase transition, instead cyclin B1 inactivates the master mitotic kinase CDK1 promoting mitotic exit. (Reviewed in Musacchio A. and Salmon E. D., Nat Rev Mol Cell Biol, 8(5): 379-93, May 2007).

A large group of proteins has been already identified to play a role in SAC functions: human MPS1 (monopolar spindle 1) kinase, also known as TTK, has certainly a major role. MPS1 is a dual tyrosine and serine/threonine kinase highly conserved from yeast to mammals. The human genome encodes for just one MPS1 gene family member, which does not have high sequence similarities with other protein kinases.

MPS1 is a cell cycle regulating enzyme that is upregulated and activated in mitosis upon phosphorylation (Stucke V M, et al., Embo J. 21 (7): 1723, 2002).

In *saccharomyces cerevisiae*, MPS1 controls spindle-pole body duplication (Winey M. et al., J. Cell Biol. 114: 745, 1991), spindle assembly (Jones, M. H. et al., Curr. Biol. 15: 160, 2005) and the spindle assembly checkpoint (Weiss and Winey, J. Cell. Biol. 132: 111, 1996). Instead, in higher eukaryotes the MPS1 kinase activity is mainly involved in SAC regulation and functions (Jelluma, N. et al., Cell 132: 233, 2008).

RNA interference experiments indicate that in the absence of MPS1 the SAC functions are compromised: mitotic length is reduced and cells divide rapidly without methaphase plate alignment, which ultimately causes aberrant aneuploidization, mitotic catastrophe and is not anymore compatible with cellular survival (Jelluma, N. et al., Cell 132: 233, 2008; Tighe A. et al., J Cell Biol 2008; Jelluma, N. et al., Plos ONE 3 (6): e2415, 2008). Moreover, to support these results, a small molecule ATP-competitor MPS1 inhibitor was described and, despite its not clean selectivity profile, it was shown to be capable to inactivate SAC functions, inactivate nocodazole and taxol mediated mitotic arrest and promote cell death mainly in tumorigenic cell lines (Schmidt et al., EMBO Rep, 6(9): 866, 2005).

Despite that most of the tumors are aneuploid, MPS1 was never found to be mutated in cancer; instead, it has been found upregulated in a number of tumors of different origins, like bladder, anaplastic thyroid, breast and prostate cancer (Yuan B. et al, Clin Cancer Res, 12(4): 1121, 2006). Moreover, it was found in the signature of the top 25 genes over-expressed in CIN and aneuploid tumors which predict clinical outcome in breast and lung cancer, medulloblastoma, glioma, mesothelioma and lymphoma (Carter S L et al., Nat. Genet. 38 (9): 1043, 2006). Finally, it is highly elevated in metastatic tumors and was found to be overexpressed in p53 mutated breast cancers (Bertheau P. et al., Plos Med 4(3): e90, 2007).

Together with the fact that also other SAC components, like MAD2, BUBR1 or BUB1, have been found up-regulated in different tumors (deCarcer G. et al., Curr Med Chem 14(9): 969, 2007), it looks like that SAC functions could be required and essential to keep tumoral highly aneuploid cells capable to segregate and tumoral selectivity of SAC inhibitors is foreseen in particular for highly aneuploid tumors like colon, lung and breast carcinomas (Kops G. J. et al., Nat. Rev Cancer, 5: 773, 2005).

Finally, massive aneuploidy induction and SAC deregulation have been shown to reduce tumorigenesis in tumour prone mice sustaining the hypothesis that SAC inhibition could confer tumour growth inhibition (Weaver et al., Cancer Cell 11(1): 25, 2007). Thus, for these reasons, pharmacological attenuation of MPS1 function may have a therapeutic benefit in the treatment of several diverse cancers.

The JAKs are a family of non-receptor tyrosine kinases consisting of JAK1, JAK2, JAK3 and TYK2. Whereas JAK1, JAK2 and TYK2 are expressed ubiquitously in mammals, JAK3 is primarily expressed in hematopoietic cells. The JAKs play a crucial role in hematopoietic cytokine and growth factors signaling (Nature 1995; 377: 591-594, Annu. Rev. Immunol. 1998; 16: 293-322) and are critically involved in cell growth, survival, development and differentiation of myeloid and immune cells. Effective innate and adaptive immune responses require functional JAK signaling to protect the organism from infections or tumors and mutations, leading to loss of function, make up some of the most common inherited severe immunodeficiencies. As a consequence JAK/STAT signaling has been implicated in the mediation of many abnormal immune responses such as allergies, asthma, autoimmune diseases, transplant rejection, rheumatoid arthritis, amyotrophic lateral sclerosis and multiple sclerosis as well as in solid and hematological malignancies like leukemias and lymphomas (Immunol Rev. 2009; 228: 273-287).

In particular, the ubiquitously expressed JAK2 kinase is exclusively involved in the signal transduction mediated by erythropoietin (EPO), thrombopoietin (TPO), growth hormone (GH) and prolactin (PR). In addition, JAK2 together with the other JAKs are important for the family of cytokines that signal through the Interleukin (IL)-3 receptor (GM-CSF, IL-5) and gp130 receptors (e.g. IL-6, IL-11). All these growth factors and cytokines are mainly involved in proliferation and differentiation of myeloid cells, inflammatory response and cancer (Blood. 2009; 114: 1289-1298; Clin Cancer Res. 2006; 12: 6270s-6273s; J Leukoc Biol. 2010; 88:1145-1156; Eur J. Cancer. 2010; 46: 1223-123).

The binding of the ligand to the specific receptor seems to induce a conformational change in the receptor that allows trans- and/or autophosphorylation of the two bound JAK2 molecules. Activated JAK2 then phosphorylates specific tyrosine residues on the cytoplasmic tails of the receptors, creating docking sites for the SH2 domain of Signal Transducers and Activators of Transcription proteins (STAT). Once bound to the receptors, STATs are themselves phosphorylated by JAK2 on tyrosine residues. Phosphorylated STATs dimerize and translocate into the nucleus, where they regulate gene transcription. Thus, JAK2 is responsible for transducing a signal from the cell surface to the nucleus through a tyrosine phosphorylation signalling mechanism (J. Immun. 2007, 178:2623-2629; Oncogene 2007, 26: 6724-6737 and Cell Biochem Biophys. 2006, 44: 213-222).

JAK2, like the other JAKs, is characterized by a kinase domain (JH1) immediately adjacent to a pseudo-kinase domain (JH2) within the C-terminal half of the protein. The function of the pseudo-kinase domain is to negatively regulate the activity of the kinase domain (N. Engl. J. Med 2006, 355: 2452-2466). An activating point mutation of JAK2 (valine to phenylalanine substitution, JAK2-V617F) in the pseudo-kinase domain, together with other activating mutations in the JAK2 exon12 and in the TPO Receptor (MPLW515L/K), have been identified in hematopoietic cells of patients with myeloproliferative disorders or MPD (Nature 2005; 434: 1144-8; N Engl J Med 2005; 352: 1779-90; Lancet 2005; 365: 1054-61; Cancer Cell 2005; 7: 387-97; Blood 2006, 108: 1427-1428 and Leukemia 2008, 22: 87-95). All these data suggest that JAKs are a suitable target for the development of a MPD specific therapy (Curr. One. Reports 2009, 11: 117-124). In addition, JAK2, and in general the JAK/STAT pathway, have been shown to be activated (e.g. mutation, amplification, translocation) in hematological malignancies like, but not limited to, AML, ALL, Hodgkin's lymphoma, diffuse large B-cell lymphoma and mediastinal large B-cell lymphoma (Science 1997, 278:1309-1312; Trends in Biochemical Sciences 2007; 33: 122-131) and in a variety of solid tumors. The pharmaceutical intervention in the JAK/STAT pathway has been reviewed in AJP 2004; 165: 1449-1460; Cancer Res 2006; 66: 3162-3168; Clin Cancer Res. 2008; 14:3716-3721 and Immunol Rev. 2009; 228: 273-287.

Pyrazolyl-pyrimidine derivatives, known in the art as platelet aggregation inhibitors for the treatment of ischemia, are disclosed in the international patent applications WO2005063737 and WO2006014005; some specific compounds of the aforementioned patent applications are excluded from the present general formula.

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a pyrazolyl-pyrimidine derivative represented by formula (I):

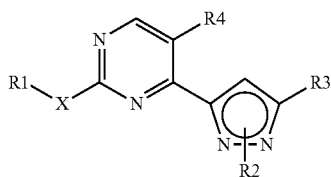

wherein

R1 is hydrogen, halogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl;

R2 is hydrogen or an optionally substituted group selected from straight or branched ($C_1$-$C_6$) alkyl, straight or branched ($C_2$-$C_6$) alkenyl, ($C_3$-$C_7$) cycloalkyl, cycloalkylalkyl, aryl, arylalkyl, heterocyclyl and heterocyclylalkyl;

R3 is a group selected from —CN, —CONR"R''', —CON(OR''')R" and COOR", wherein R" and R''' are, each independently, hydrogen or an optionally substituted group selected from straight or branched ($C_1$-$C_6$) alkyl, ($C_3$-$C_7$) cycloalkyl, cycloalkyl-alkyl, aryl, arylalkyl, heterocyclyl and heterocyclylalkyl or, together with the nitrogen atom to which they are bound, R" and R''' may form a 5- to 7-membered heteroaryl or heterocyclyl group, optionally containing one additional heteroatom selected from N, O and S;

X is a single bond or a divalent radical selected from —NR'—, —O—, —S—, —SO—, —SO$_2$— and —OSO$_2$—, wherein R' is hydrogen or an optionally substituted straight or branched ($C_1$-$C_6$) alkyl, ($C_3$-$C_7$) cycloalkyl, cycloalkyl-alkyl, aryl, arylalkyl, heterocyclyl and heterocyclylalkyl or, together with the nitrogen atom to which they are bound, R' and R1 may form a 5- to 7-membered heteroaryl or heterocyclyl group optionally containing one additional heteroatom selected from N, O and S;

R4 is a group selected from hydrogen, halogen and cyano; or a pharmaceutically acceptable salt thereof, with the proviso that the following compounds are excluded:

N-tert-butyl-1-(6-methoxypyridin-3-yl)-5-(pyrimidin-4-yl)-1H-pyrazole-3-carboxamide, methyl 1-(6-methoxypyridin-3-yl)-5-[2-(methylsulfanyl)pyrimidin-4-yl]-1H-pyrazole-3-carboxylate, methyl 1-(6-methoxypyridin-3-yl)-5-(pyrimidin-4-yl)-1H-pyrazole-3-carboxylate, 1-(6-methoxypyridin-3-yl)-5-(pyrimidin-4-yl)-1H-pyrazole-3-carboxylic acid and

[1-(6-methoxypyridin-3-yl)-5-(pyrimidin-4-yl)-1H-pyrazol-3-yl](4-methylpiperazin-1-yl)methanone.

The present invention also provides methods of synthesizing the substituted derivatives, represented by formula (I), prepared through a process consisting of standard synthetic transformations and isomers, tautomers, hydrates, solvates, complexes, metabolites, prodrugs, carriers, N-oxides and pharmaceutically acceptable salts.

The present invention also provides a method for treating diseases caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PIM3, PKAalpha, PKCbeta, PLK1, RET, ROS1, SULU1, Syk, TLK2, TRKA, TYK, VEGFR2, VEGFR3, ZAP70; more particularly PIM1, PIM2, PIM3, MPS1, JAK2, JAK3.

A preferred method of the present invention is to treat a disease caused by and/or associated with dysregulated protein kinase activity selected from the group consisting of cancer, cell proliferative disorders, viral infections, immune disorders, neurodegenerative disorders and cardiovascular diseases.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma, highly aneuploid tumors and tumors which do overexpress mitotic checkpoint.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

Another preferred method of the present invention is to treat immune disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat neurodegenerative disorders, such as Alzheimer's disease, Parkinson's disease and Huntington's disease.

Another preferred method of the present invention is to treat specific cardiovascular diseases, such as coronary heart diseases, cardiomyopathies, ischaemic heart diseases, heart failure, hypertensive heart diseases, inflammatory heart diseases and valvular heart diseases.

In addition, the method of the present invention also provides tumor angiogenesis and metastasis inhibition as well as the treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent.

The present invention further provides an in vitro method for inhibiting protein kinase activity which comprises contacting the kinase with an effective amount of a compound of formula (I) as defined above.

The present invention also provides a pharmaceutical composition comprising a therapeutically effective amount of a compound of formula (I) or a pharmaceutically acceptable salt thereof and at least one pharmaceutically acceptable excipient, carrier and/or diluent.

The present invention further provides a pharmaceutical composition comprising a compound of formula (I) in combination with one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In another aspect the invention provides a compound of formula (I) or a pharmaceutically acceptable salt thereof, as defined above, for use as a medicament.

Moreover, the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of formula (I) as defined above, also their isomers, tautomers, hydrates, solvates, complexes, metabolites, prodrugs, carriers and N-oxides are object of the present invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bound compounds, which release in vivo the active parent drug according to formula (I). N-oxides are compounds of formula (I) wherein nitrogen and oxygen are tethered through a dative bond.

In formula (I)

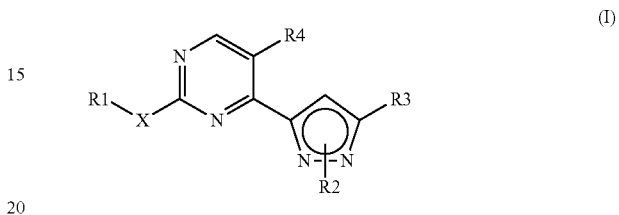

R2 can be bound to any one of the nitrogen atoms of the pyrazole ring as per formula (Ia) and (Ib):

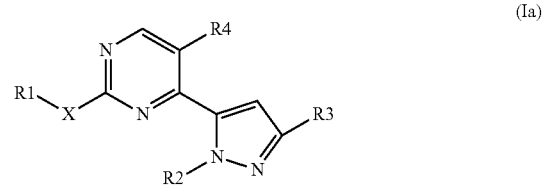

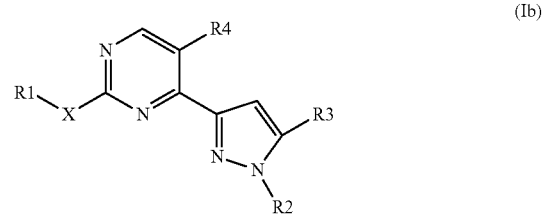

as such, unless otherwise provided, when in compounds of formula (I) only one of the tautomeric forms of formula (Ia) or (Ib) is indicated, the remaining one has still to be intended as comprised within the scope of the invention.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

As such, unless otherwise provided, when in compounds of formula (I) R2 is hydrogen, and only one of the following tautomeric forms of formula (Ia') or (Ib') is indicated, the remaining one has still to be intended as comprised within the scope of the invention:

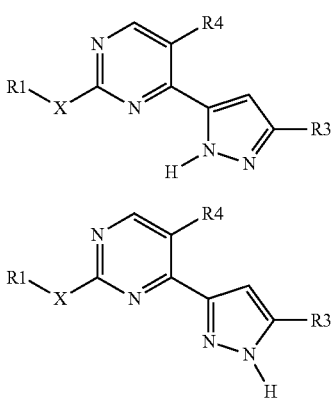

(Ia')

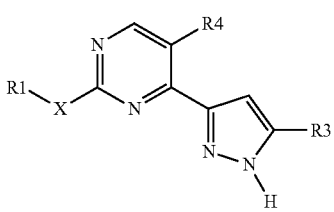

(Ib')

The term "aryl" includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5- to 6-membered ring with from 1 to 3 heteroatoms selected from N, O and S. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl"), we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$(C_3-C_7)$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloheptane, cycloheptene, cycloheptadiene.

With the term "straight or branched $(C_1-C_6)$ alkyl", hence comprehensive of $(C_1-C_4)$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $(C_2-C_6)$ alkenyl", we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $(C_2-C_6)$ alkynyl" we intend any of the groups such as, for instance, ethynyl, 2-propynyl, 4-pentynyl, and the like.

According to the present invention and unless otherwise provided, any of the above R1, R2, R3, R', R" and R'" groups may be optionally substituted, in any of their free positions, by one or more groups, for instance 1 to 6 groups, independently selected from: halogen, nitro, oxo groups (=O), cyano, $(C_1-C_6)$ alkyl, polyfluorinated alkyl, polyfluorinated alkoxy, alkenyl, alkynyl, hydroxyalkyl, aryl, arylalkyl, heterocyclyl, $(C_3-C_7)$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term "halogen" we intend a fluorine, chlorine, bromine or iodine atom.

With the term "cyano" we intend a —CN residue.

With the term "nitro" we intend a —NO$_2$ group.

With the term "alkenyl" or "alkynyl" we intend any of the aforementioned straight or branched $(C_2-C_6)$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term "polyfluorinated alkyl or alkoxy" we intend any of the above straight or branched $(C_1-C_6)$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the terms "alkoxy, aryloxy, heterocyclyloxy" and derivatives thereof, we intend any of the above $(C_1-C_6)$ alkyl, aryl or heterocyclyl groups linked to the rest of the molecule through an oxygen atom (—O—).

From all of the above, it is clear to the skilled person that any group whose name is a composite name such as, for instance, arylamino, has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $(C_3-C_7)$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of formula (I) are the compounds wherein: R3 is CN, CONR"R'" or CON(OR'")R", and R1, X, R2, R4, R', R" and R'" are as defined above.

Another preferred class of compounds of formula (I) are the compounds wherein: X is a single bond or a divalent radical selected from —NR', —O— and —S—, wherein R1, R2, R3, R4, R', R" and R'" are as defined above.

Another preferred class of compounds of formula (I) are the compounds wherein: R1 is hydrogen or an optionally substituted group selected from straight or branched ($C_1$-$C_6$) alkyl, aryl, arylalkyl, heterocyclyl and heterocyclylalkyl or, together with the nitrogen atom to which they are bound, R' and R1 may form a 5- to 7-membered heteroaryl or heterocyclyl group, optionally containing one additional heteroatom selected from N, O and S; and X, R2, R3, R4, R', R" and R'" are as defined above.

Another preferred class of compounds of formula (I) are the compounds wherein: R3 is CN, CONR"R'" or CONHOR'", wherein R'" is hydrogen, and R1, X, R2, R4, R' and R" are as above defined.

Preferred specific compounds (cpd) of formula (I) or a salt thereof are the compounds listed below:

1) 3-{2-[(4-bromo-2-methoxyphenyl)amino]pyrimidin-4-yl}-N-(2,6-diethylphenyl)-1-methyl-1H-pyrazole-5-carboxamide,
2) N-(2,6-diethylphenyl)-3-(2-{[2-methoxy-4-(4-methylpiperazin-1-yl)phenyl]amino}pyrimidin-4-yl)-1-methyl-1H-pyrazole-5-carboxamide,
3) N-(2,6-diethylphenyl)-5-(2-{[2-methoxy-4-(4-methylpiperazin-1-yl)phenyl]amino}pyrimidin-4-yl)-1-methyl-1H-pyrazole-3-carboxamide,
4) 5-{2-[(4-bromo-2-methoxyphenyl)amino]pyrimidin-4-yl}-N-(2,6-diethylphenyl)-1-methyl-1H-pyrazole-3-carboxamide,
5) 3-{2-[(4-bromo-2-methoxyphenyl)amino]pyrimidin-4-yl}-N-(2,6-diethylphenyl)-1-(4-methoxybenzyl)-1H-pyrazole-5-carboxamide,
6) 5-{2-[(4-bromo-2-methoxyphenyl)amino]pyrimidin-4-yl}-N-(2,6-diethylphenyl)-1-(4-methoxybenzyl)-1H-pyrazole-3-carboxamide,
7) N-(2,6-diethylphenyl)-5-{2-[(2-methoxyphenyl)amino]pyrimidin-4-yl}-1-methyl-1H-pyrazole-3-carboxamide,
8) N-(2,6-diethylphenyl)-5-[2-({4-[4-(2-hydroxyethyl)piperazin-1-yl]-2-methoxyphenyl}amino)pyrimidin-4-yl]-1-methyl-1 H-pyrazole-3-carboxamide,
9) N-(2,6-diethylphenyl)-1-(4-methoxybenzyl)-5-(2-{[2-methoxy-4-(4-methylpiperazin-1-yl)phenyl]amino}pyrimidin-4-yl)-1H-pyrazole-3-carboxamide,
10) N-(2,6-diethylphenyl)-1-(4-methoxybenzyl)-5-{2-[(2-methoxyphenyl)amino]pyrimidin-4-yl}-1H-pyrazole-3-carboxamide,
11) N-(2,6-diethylphenyl)-5-(2-{[2-methoxy-4-(4-methylpiperazin-1-yl)phenyl]amino}pyrimidin-4-yl)-1H-pyrazole-3-carboxamide,
12) N-(2,6-diethylphenyl)-1-(4-methoxybenzyl)-3-{2-[(2-methoxyphenyl)amino]pyrimidin-4-yl}-1H-pyrazole-5-carboxamide,
13) N-(2,6-diethylphenyl)-5-[2-({4-[4-(2-hydroxyethyl)piperazin-1-yl]-2-methoxyphenyl}amino)pyrimidin-4-yl]-1H-pyrazole-3-carboxamide,
14) N-(2,6-diethylphenyl)-5-{2-[(2-methoxyphenyl)amino]pyrimidin-4-yl}-1H-pyrazole-3-carboxamide,
15) 3-(2-aminopyrimidin-4-yl)-1-(5-chloro-2-ethylphenyl)-1H-pyrazole-5-carboxamide,
16) 5-(2-aminopyrimidin-4-yl)-1-(5-chloro-2-ethylphenyl)-1H-pyrazole-3-carboxamide,
17) 5-(2-aminopyrimidin-4-yl)-1-(5-chloro-2-methylphenyl)-1H-pyrazole-3-carboxamide,
18) 3-(2-aminopyrimidin-4-yl)-1-(5-chloro-2-methylphenyl)-1H-pyrazole-5-carboxamide,
19) 5-[2-(methylsulfanyl)pyrimidin-4-yl]-1H-pyrazole-3-carboxamide,
20) 1-tert-butyl-5-[2-(methylsulfanyl)pyrimidin-4-yl]-1H-pyrazole-3-carboxamide,
21) 5-[2-(methylsulfanyl)pyrimidin-4-yl]-1-(piperidin-4-yl)-1H-pyrazole-3-carboxamide,
22) 3-[2-(methylsulfanyl)pyrimidin-4-yl]-1-(piperidin-4-yl)-1H-pyrazole-5-carboxamide,
23) 3-(2-hydroxypyrimidin-4-yl)-1-(3-methoxybenzyl)-1H-pyrazole-5-carboxamide,
24) 1-(3-methoxybenzyl)-3-(2-methylpyrimidin-4-yl)-1H-pyrazole-5-carboxamide,
25) 1-tert-butyl-5-(2-phenylpyrimidin-4-yl)-1H-pyrazole-3-carboxamide,
26) 1-tert-butyl-5-{2-[4-(piperazin-1-yl)phenoxy]pyrimidin-4-yl}-1H-pyrazole-3-carboxamide,
27) 1-tert-butyl-5-[2-(dimethylamino)pyrimidin-4-yl]-1H-pyrazole-3-carboxamide,
28) 1-tert-butyl-5-(2-methoxypyrimidin-4-yl)-1H-pyrazole-3-carboxamide,
29) N-hydroxy-5-[2-(methylsulfanyl)pyrimidin-4-yl]-1H-pyrazole-3-carboxamide,
30) N-benzyl-1-tert-butyl-5-(2-phenoxypyrimidin-4-yl)-1H-pyrazole-3-carboxamide,
31) 1-tert-butyl-5-(2-phenoxypyrimidin-4-yl)-N-(propan-2-yl)-1H-pyrazole-3-carboxamide,
32) 1-tert-butyl-5-(2-phenoxypyrimidin-4-yl)-N-phenyl-1H-pyrazole-3-carboxamide,
33) 1-tert-butyl-N-methyl-5-(2-phenoxypyrimidin-4-yl)-1H-pyrazole-3-carboxamide,
34) 1-tert-butyl-N,N-diethyl-5-(2-phenoxypyrimidin-4-yl)-1H-pyrazole-3-carboxamide,
35) 1-tert-butyl-5-[2-(4-cyanophenoxy)pyrimidin-4-yl]-N-methyl-1H-pyrazole-3-carboxamide,
36) 1-tert-butyl-5-[2-(4-cyanophenoxy)pyrimidin-4-yl]-N-(propan-2-yl)-1H-pyrazole-3-carboxamide,
37) 1-tert-butyl-5-[2-(4-cyanophenoxy)pyrimidin-4-yl]-N-phenyl-1H-pyrazole-3-carboxamide,
38) N-benzyl-1-tert-butyl-5-[2-(4-cyanophenoxy)pyrimidin-4-yl]-1H-pyrazole-3-carboxamide,
39) 1-tert-butyl-5-[2-(dimethylamino)pyrimidin-4-yl]-N-methyl-1H-pyrazole-3-carboxamide,
40) 1-tert-butyl-5-[2-(dimethylamino)pyrimidin-4-yl]-N-(propan-2-yl)-1H-pyrazole-3-carboxamide,
41) 1-tert-butyl-5-[2-(dimethylamino)pyrimidin-4-yl]-N-phenyl-1H-pyrazole-3-carboxamide,
42) N-benzyl-1-tert-butyl-5-[2-(dimethylamino)pyrimidin-4-yl]-1H-pyrazole-3-carboxamide,
43) 1-tert-butyl-5-[2-(morpholin-4-yl)pyrimidin-4-yl]-N-phenyl-1H-pyrazole-3-carboxamide and
44) N-benzyl-1-tert-butyl-5-[2-(morpholin-4-yl)pyrimidin-4-yl]-1H-pyrazole-3-carboxamide.

For a reference to any specific compound of formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance, by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

The reported Scheme 1 shows the preparation of intermediate compounds of formula (IVa)-(IVf).

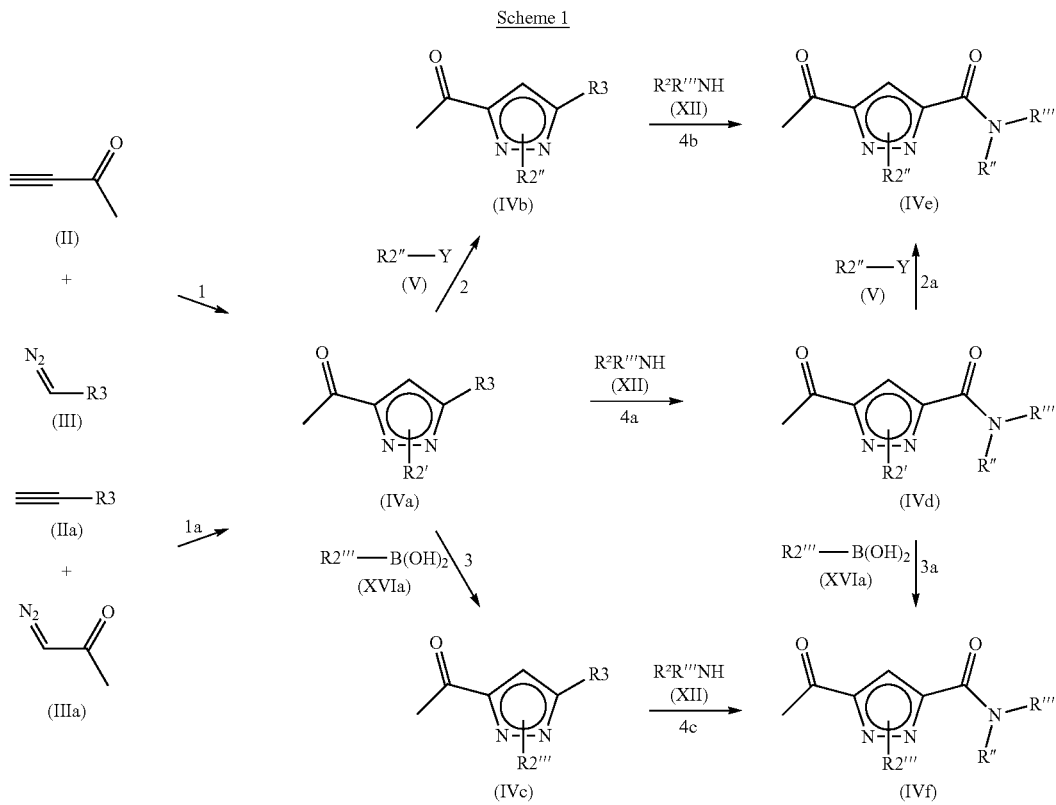

In the above scheme R3 is —COOR5 or —CONR"R'", wherein R5 is an optionally substituted ($C_1$-$C_6$) alkyl and R" and R'" are as defined above; R2' is hydrogen; R2" is as R2 but not hydrogen or aryl; R2'" is as R2 but not hydrogen; and Y represents a suitable leaving group such as iodo, bromo, chloro, or a sulphonate group (e.g. —$OSO_2CF_3$, —$OSO_2CH_3$, —$OSO_2Ph$-pMe).

Accordingly, a process of the present invention comprises the following steps:

st. 1) mixing an α-carbonyl alkyne of formula (II):

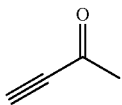

(II)

with an α-diazocarbonyl derivative of formula (III):

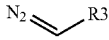

(III)

wherein R3 is —COOR5 or —CONR"R'", wherein R5 is an optionally substituted ($C_1$-$C_6$) alkyl and R" and R'" are as defined above;

alternatively st. 1a) mixing an α-carbonyl alkyne of formula (IIa):

(IIa)

wherein R3 is —COOR5 or —CONR"R'", wherein R5 is an optionally substituted ($C_1$-$C_6$) alkyl and R" and R'" are as defined above, with an α-diazocarbonyl derivative of formula (IIa):

(IIIa)

st. 2) reacting the resultant compound of formula (IVa):

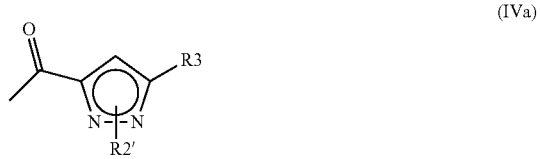

(IVa)

wherein R2' is hydrogen and R3 is as defined above, with a compound of formula (V):

R2"-Y (V)

wherein R2'' is as R2 but not hydrogen or aryl, and Y represents a suitable leaving group such as iodo, bromo, chloro, or a sulphonate group (e.g. —OSO$_2$CF$_3$, —OSO$_2$CH$_3$, —OSO$_2$Ph-pMe), to give a compound of formula (IVb):

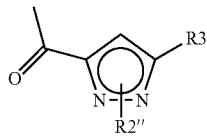
(IVb)

wherein R2'' is as defined above; optionally
st. 4b) reacting the resultant compound of formula (IVb) wherein R3 is —COOR5, and R5 is as defined above, with a compound of formula (XII):

R''R'''NH (XII)

wherein R'' and R''' are as defined above, to give a compound of formula (IVe):

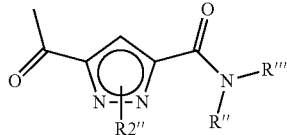
(IVe)

wherein R2'', R'' and R''' are as defined above;
or
st. 3) reacting a compound of formula (IVa), as defined above, with a compound of formula (XVIa):

R2'''—B(OH)$_2$ (XVIa)

wherein R2''' is as R2 but not hydrogen, to give a compound of formula (IVc):

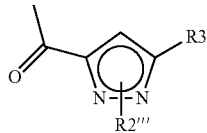
(IVc)

wherein R2''' and R3 are as defined above; optionally
st. 4c) reacting a compound of formula (IVc) wherein R3 is COOR5 and R5 is as defined above, with a compound of formula (XII):

R''R'''NH (XII)

wherein R'' and R''' are as defined above, to give a compound of formula (IVf):

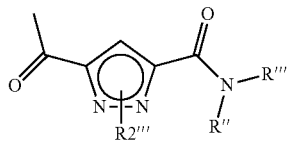
(IVf)

wherein R2''', R'' and R''' are as defined above;
or
st. 4a) reacting a compound of formula (IVa), wherein R2' is hydrogen and R3 is COOR5, wherein R5 is as defined above, with a compound of formula (XII)

R''R'''NH (XII)

by the preparation of the corresponding acid derivative, or a salt thereof, or to give directly a compound of formula (IVd):

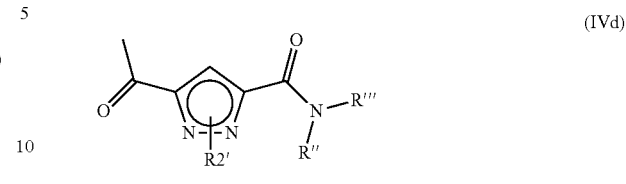
(IVd)

wherein R2' is hydrogen and R'' and R''' are as defined above; optionally
st. 2a) reacting a compound of formula (IVd) as defined above, with a compound of formula (V) as defined above, to give a compound of formula (IVe) as defined above;
or
st. 3a) reacting a compound of formula (IVd) as defined above, with a compound of formula (XVIa) as defined above, to give a compound of formula (IVf) as defined above.

The reported Scheme 2 shows the preparation of a compound of formula (I):

Scheme 2

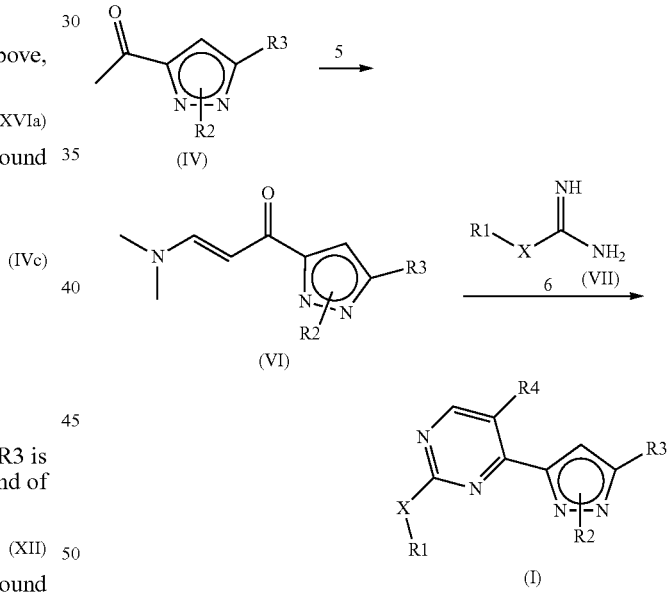

In the above scheme R2 is as defined in formula (I); R3 is a group selected from —CONR''R''' and COOR5, wherein R5 is an optionally substituted (C$_1$-C$_6$) alkyl and R'' and R''' are as defined above; R1 is hydrogen or an optionally substituted group selected from amino, straight or branched (C$_1$-C$_6$) alkyl, (C$_3$-C$_7$) cycloalkyl, cycloalkyl-alkyl, aryl, arylalkyl, heterocyclyl and heterocyclylalkyl; X is a single bond or a divalent radical selected from —NR'—, —O— and —S—, wherein R' is as defined above; and R4 is hydrogen.

Accordingly, a process of the present invention comprises the following steps:
st. 5) mixing the compound of formula (IV) obtained as described in steps 1), 1a), 2), 2a), 3), 3a), 4a), 4b) or 4c):

(IV)

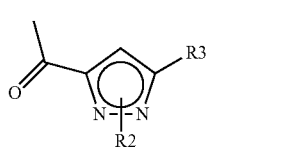

wherein R2 is as defined in formula (I) and R3 is a group selected from —CONR"R'" and COOR5, wherein R5 is an optionally substituted (C$_1$-C$_6$) alkyl and R" and R'" are as defined above, with a dimethylformamide-dialkylacetale;

st. 6) reacting the resultant compound of formula (VI):

(VI)

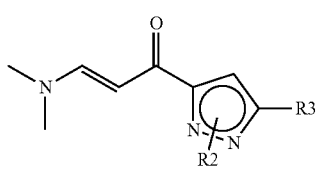

wherein R2 and R3 are as defined above, with a compound of formula (VII):

(VII)

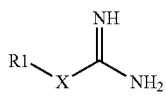

wherein X is a single bond or a divalent radical selected from —NR', —O— and —S—, wherein R' is as defined above; and R1 is hydrogen or an optionally substituted group selected from amino, straight or branched (C$_1$-C$_6$) alkyl, (C$_3$-C$_7$) cycloalkyl, cycloalkyl-alkyl, aryl, arylalkyl, heterocyclyl and heterocyclylalkyl; so as to obtain a compound of formula (I):

(I)

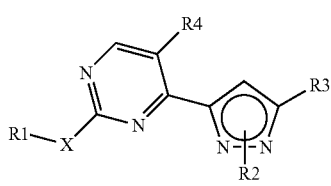

wherein R1 is hydrogen or an optionally substituted group selected from amino, straight or branched (C$_1$-C$_6$) alkyl, (C$_3$-C$_7$) cycloalkyl, cycloalkyl-alkyl, aryl, arylalkyl, heterocyclyl and heterocyclylalkyl; X is a single bond or a divalent radical selected from —NR', —O— and —S—, wherein R' is as defined above; R2 is as defined in formula (I); R3 is a group selected from —CONR"R'" and COOR5, wherein R5, R" and R'" are as defined above; and R4 is hydrogen; optionally converting a compound of formula (I) into another different compound of formula (I), and if desired, converting a compound of formula (I) into a pharmaceutically acceptable salt thereof or converting a salt into the free compound (I).

The present invention further provides an alternative process for the preparation of a compound of formula (I) as defined above, reported in Scheme 3 below:

Scheme 3

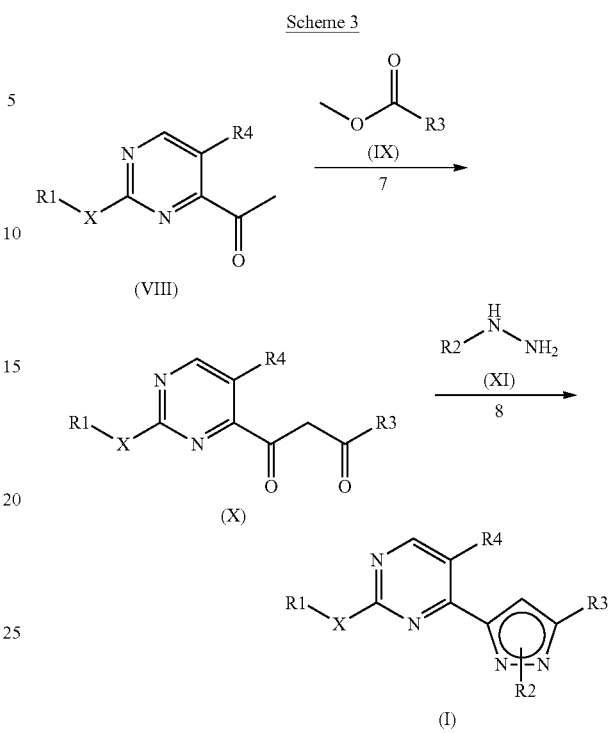

In the above scheme R1 is hydrogen or an optionally substituted group selected from amino, straight or branched (C$_1$-C$_6$) alkyl, (C$_3$-C$_7$) cycloalkyl, cycloalkyl-alkyl, aryl, arylalkyl, heterocyclyl and heterocyclylalkyl; X is a single bond or a divalent radical selected from —NR'—, —O— and —S—, wherein R' is as defined above; R4 is as defined in formula (I); R3 is COOR5, wherein R5 is as defined above; and R2 is as defined in formula (I).

Accordingly, a process of the present invention comprises the following steps:

st. 7) reacting a compound of formula (VIII):

(VIII)

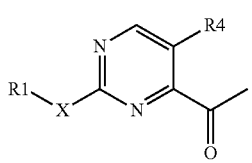

wherein R1 is hydrogen or an optionally substituted group selected from amino, straight or branched (C$_1$-C$_6$) alkyl, (C$_3$-C$_7$) cycloalkyl, cycloalkyl-alkyl, aryl, arylalkyl, heterocyclyl and heterocyclylalkyl; X is a single bond or a divalent radical such as —NR'—, —O— and —S—, wherein R' is as defined above and R4 is as defined in formula (I), with a compound of formula (IX):

(IX)

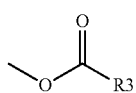

wherein R3 is COOR5, wherein R5 is as defined above;

st. 8) reacting the resultant compound of formula (X):

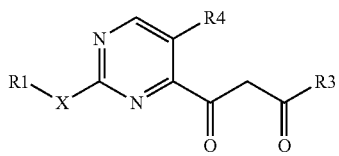

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; X is a single bond or a divalent radical such as —NR'—, —O— and —S—, wherein R' is as defined above; R3 is —COOR5, wherein R5 is as defined above; and R4 is as defined in formula (I), with an hydrazine of formula (XI) or a salt thereof:

wherein R2 is as defined in formula (I), so as to obtain a compound of formula (I):

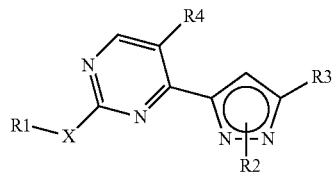

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; X is a single bond or a divalent radical such as —NR'—, —O— and —S—, wherein R' is as defined above; R2 is as defined in formula (I); R3 is —COOR5, wherein R5 is as defined above; and R4 is as defined in formula (I); optionally converting a compound of formula (I) into another different compound of formula (I), and if desired, converting a compound of formula (I) into a pharmaceutically acceptable salt thereof or converting a salt into the free compound of formula (I).

The present invention further provides an alternative process for the preparation of a compound of formula (I) as defined above, reported in Scheme 4 below:

Scheme 4

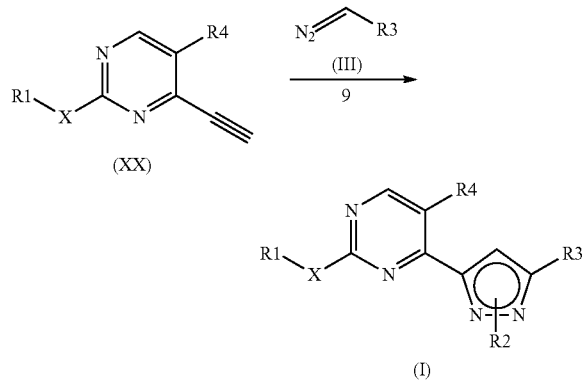

In the above scheme R1 and R4 are as defined in formula (I); X is a single bond or a divalent radical selected from —NR'—, —O— and —S—, wherein R' is as defined above; R3 is COOR5 or CONR"R'", wherein R5, R" and R'" are as defined above; and R2 is hydrogen.

Accordingly, a process of the present invention comprises the following steps:

st. 9) reacting a compound of formula (XX):

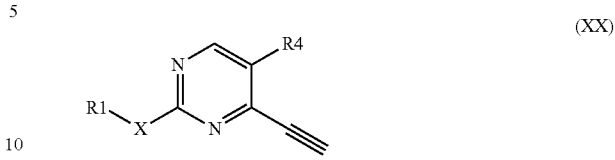

wherein R1 is as defined in formula (I) and X is a single bond or a divalent radical selected from —NR'—, —O— and —S— wherein R' is as defined above; and R4 is as defined in formula (I); with an α-diazocarbonyl compound of formula (III):

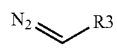

wherein R3 is —COOR5 or —CONR"R'", wherein R5, R" and R'" are as defined above;

so as to obtain a compound of formula (I):

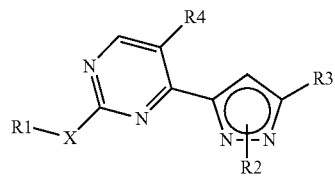

wherein R1 is as defined in formula (I); X is a single bond or a divalent radical selected from —NR'—, —O— and —S—, wherein R' is as defined above; R2 is hydrogen; R3 is COOR5 or CONR"R'", wherein R5, R" and R'" are as defined above; and R4 is as defined in formula (I); optionally converting a compound of formula (I) into another different compound of formula (I), and if desired, converting a compound of formula (I) into a pharmaceutically acceptable salt thereof or converting a salt into the free compound (I).

As said above, the compounds of formula (I) which are prepared according to the process object of the invention, can be conveniently converted into other compounds of formula (I) by operating according to well-known synthetic conditions, the following being examples of possible conversions:

Conv. a) converting a compound of formula (I) wherein R3 is COOR5 wherein R5 is an optionally substituted ($C_1$-$C_6$) alkyl into the corresponding compound of formula (I) wherein R3 is a group COOH, or a salt thereof, under acidic or basic conditions:

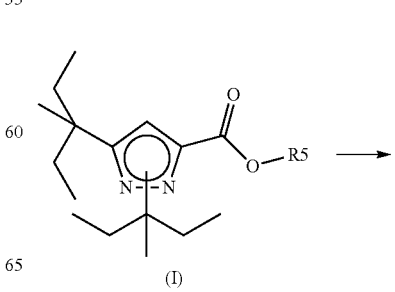

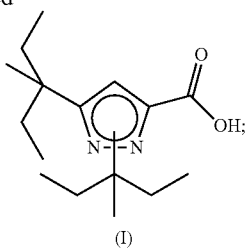
(I)

Conv. b) converting a compound of formula (I) wherein R3 is a group COOH or a salt thereof, into the corresponding compound of formula (I) wherein R3 is a group —CONR"R'" or —CON(OR'")R" wherein R" and R'" are as defined above, through reaction with a derivative of formula R"R'"NH (XII) or R"NHOR'" (XIII), wherein R" and R'" are as defined above, under basic conditions and in the presence of a suitable condensing agent:

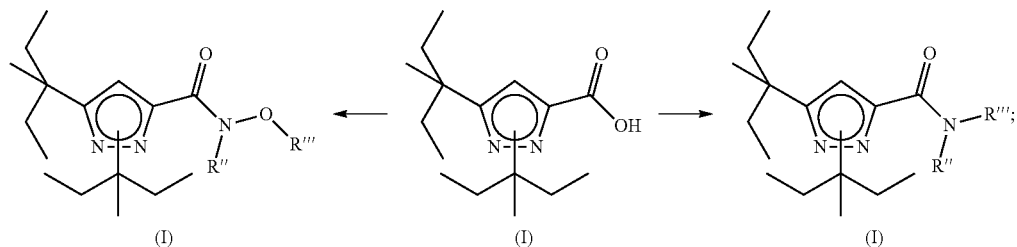

Conv. c) converting a compound of formula (I) wherein R3 is COOR5 and R5 is an optionally substituted (C₁-C₆) alkyl into the corresponding compound of formula (I) wherein R3 is a group —CONR"R'" or —CON(OR'")R", wherein R" and R'" are as defined above, through reaction with a derivative of formula R"R'"NH (XII) or R"NHOR'" (XIII) wherein R" and R'" are as defined above:

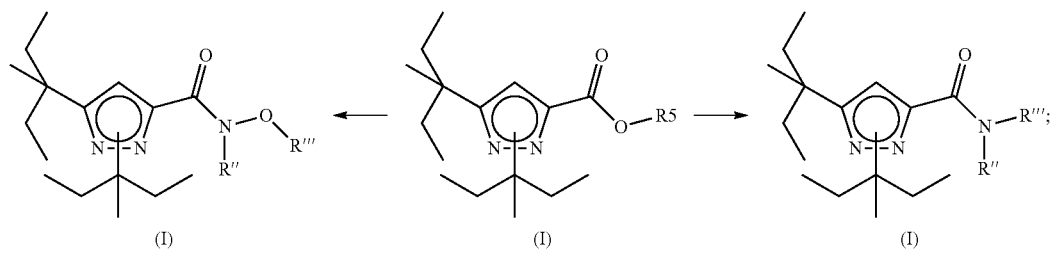

Conv. d) converting a compound of formula (I) wherein R1 is an optionally substituted group selected from straight or branched (C₁-C₆) alkyl, (C₃-C₇) cycloalkyl, cycloalkyl-alkyl, aryl, arylalkyl, heterocyclyl and heterocyclylalkyl; and X is —S— into the corresponding compound of formula (I) wherein X is —SO₂— under oxidative conditions:

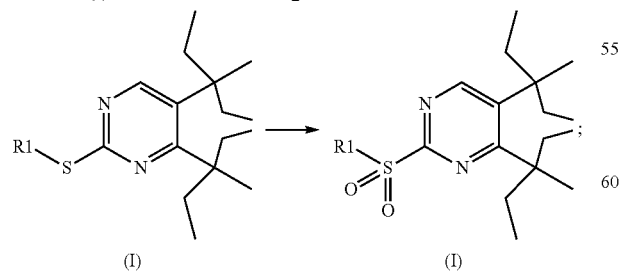

Conv. e) converting a compound of formula (I) wherein R1 is an optionally substituted group selected from straight or branched (C₁-C₆) alkyl, (C₃-C₇) cycloalkyl, cycloalkyl-alkyl, aryl, arylalkyl, heterocyclyl and heterocyclylalkyl;

and X is —SO₂— into the corresponding compound of formula (I) wherein X is —O—, by reacting the sulfonyl group with a compound of formula R1-OH (XIV) wherein R1 is an optionally substituted group selected from amino, straight or branched (C₁-C₆) alkyl, (C₃-C₇) cycloalkyl, cycloalkyl-alkyl, aryl, arylalkyl, heterocyclyl and heterocyclylalkyl:

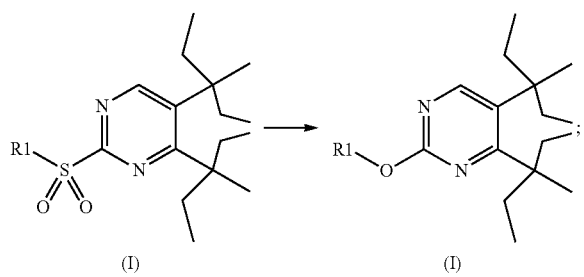

Conv. f) converting a compound of formula (I) wherein R1 is an optionally substituted group selected from straight or branched (C₁-C₆) alkyl, (C₃-C₇) cycloalkyl, cycloalkyl-alkyl, aryl, arylalkyl, heterocyclyl and heterocyclylalkyl; and X is —SO₂— into the corresponding compound of formula (I) wherein X is —NR'—, wherein R' is as defined above, by reacting the sulfonyl group with an amine of formula R1-NHR' (XV) wherein R1 is an optionally substituted group selected from amino, straight or branched (C₁-C₆) alkyl, (C₃-C₇) cycloalkyl, cycloalkyl-alkyl, aryl, arylalkyl, heterocyclyl and heterocyclylalkyl:

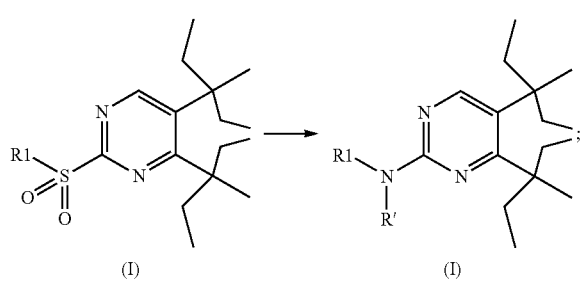

Conv. g) converting a compound of formula (I), wherein R1 is an optionally substituted group selected from straight or branched (C₁-C₆) alkyl, (C₃-C₇) cycloalkyl, cycloalkyl-alkyl, aryl, arylalkyl, heterocyclyl and heterocyclylalkyl and X is —SO$_2$—, into the corresponding compound of formula (I) wherein X is —S— by reaction with a thiol of formula R1-SH (XVIII) wherein R1 is an optionally substituted group selected from straight or branched (C$_1$-C$_6$) alkyl, (C$_3$-C$_7$) cycloalkyl, cycloalkyl-alkyl, aryl, arylalkyl, heterocyclyl and heterocyclylalkyl:

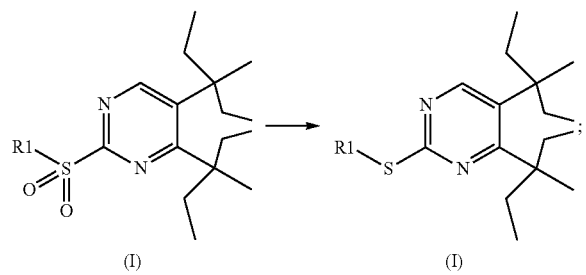

Conv. h) converting a compound of formula (I) wherein R1 is methyl and X is —S—, into the corresponding compound of formula (I) wherein R1 is an optionally substituted aryl and X is a single bond, by reacting it with an arylboronic acid of formula R1-B(OH)$_2$ (XVI), wherein R1 is an optionally substituted aryl, in the presence of a palladium catalyst:

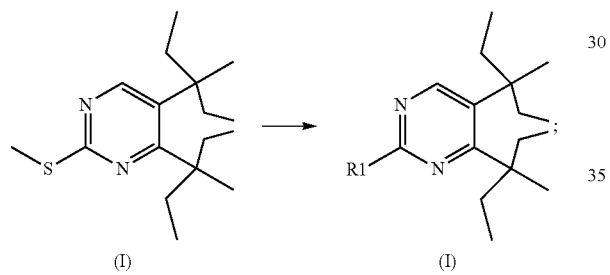

Conv. i) converting a compound of formula (I) wherein R2 is a suitable protecting group such as t-butyl, trityl, p-methoxybenzyl, m-methoxybenzyl or benzyl, into the corresponding compound of formula (I) wherein R2 is hydrogen, by cleavage of the protecting group according to conventional methods in acidic or basic conditions. Preferably the cleavage is carried out by mixing with hydrochloric acid or trifluoroacetic acid in the presence of a suitable solvent as dichloromethane (DCM) and the like:

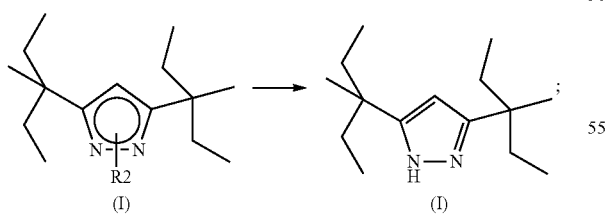

Conv. j) converting a compound of formula (I) wherein R2 is hydrogen, into the corresponding compound of formula (I) wherein R2 is as defined above but not hydrogen or aryl, through reaction with a compound of formula (Va):

R2''-Y'  (Va)

wherein R2'' is as R2 but not hydrogen or aryl and Y' is OH or a group that, optionally upon activation, may work as a suitable leaving group such as iodo, bromo, chloro or a sulfonate group (e.g. —OSO$_2$CF$_3$, —OSO$_2$CH$_3$ or —OSO$_2$PhMe):

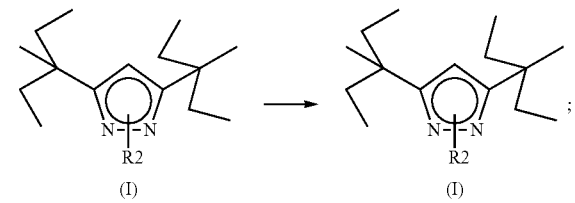

Conv. k) converting a compound of formula (I) wherein R2 is hydrogen, into a compound of formula (I) wherein R2 is as defined above but not hydrogen, through reaction with a compound of formula R2'''—B(OH)$_2$ (XVIa) as defined above:

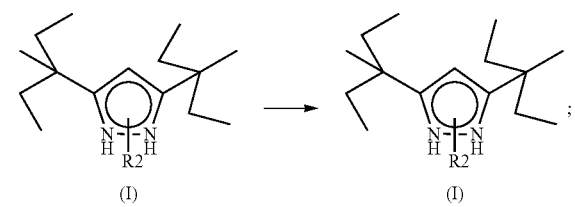

Conv. l) converting a compound of formula (I) wherein X is as defined in formula (I) but not —SO$_2$ or —OSO$_2$—, and R1 is an aryl, i.e. phenyl, substituted by bromine, into the corresponding compound of formula (I) wherein R1 is an aryl, i.e. phenyl, substituted by NR''R''', by treatment with an amine of formula R''R'''NH (XII) as defined above:

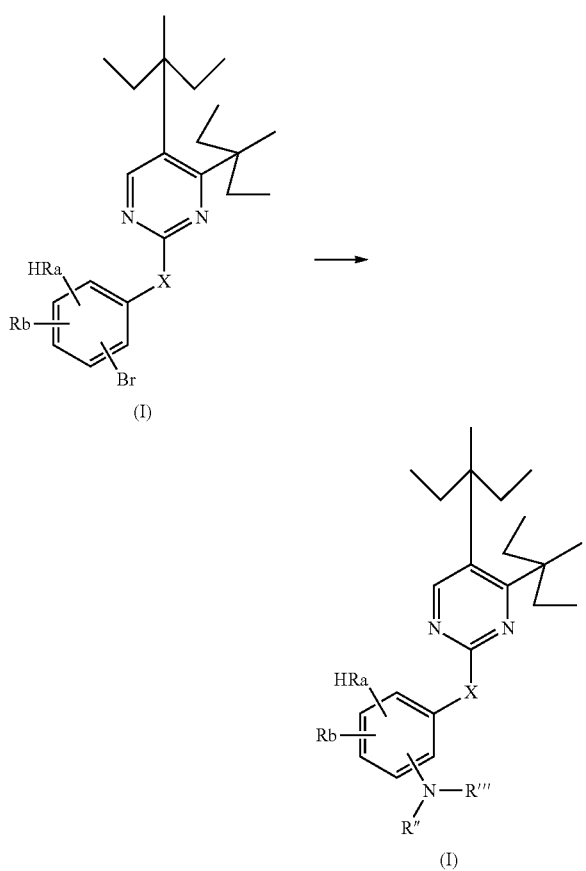

wherein Ra and Rb are independently halogen but not bromine, hydrogen, nitro, cyano, (C$_1$-C$_6$) alkyl, polyfluorinated alkyl, polyfluorinated alkoxy, alkenyl, alkynyl, hydroxyalkyl, aryl, arylalkyl, heterocyclyl, (C₃-C₇) cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

Conv. m) converting a compound of formula (I) wherein X is —NH— and R1 is hydrogen, into the corresponding compound of formula (I) wherein R1 is an aryl, i.e. phenyl, substituted by Ra, Rb, Rc:

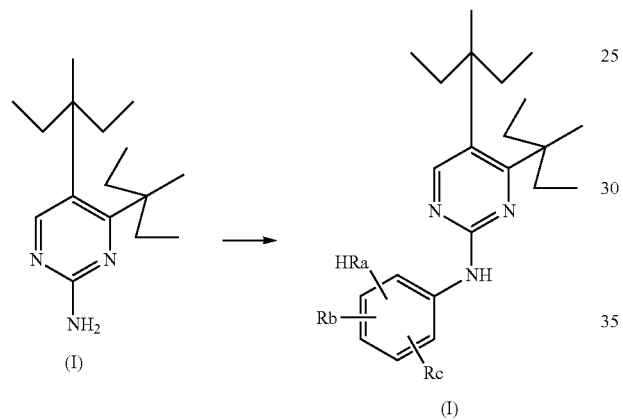

wherein Ra, Rb and Rc are independently hydrogen, nitro, cyano, (C₁-C₆) alkyl, polyfluorinated alkyl, polyfluorinated alkoxy, alkenyl, alkynyl, hydroxyalkyl, aryl, arylalkyl, heterocyclyl, (C₃-C₇) cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate, by treatment with an iodo derivative of formula (XVII):

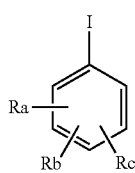

wherein Ra, Rb and Rc are as defined above, in the presence of palladium; Conv. n) converting a compound of formula (I) wherein R1 is hydrogen and X is —O— into the corresponding compound of formula (I) wherein R1 is trifluoromethyl and X is —OSO₂— by reaction with a triflating agent:

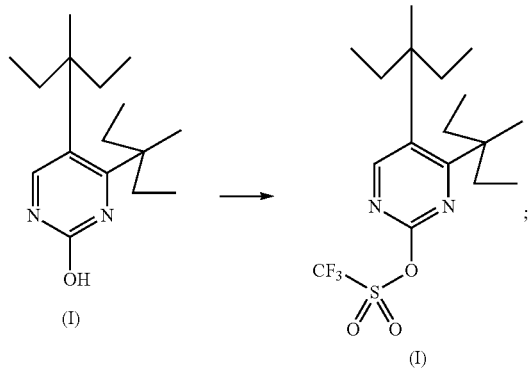

Conv. o) converting a compound of formula (I) wherein R1 is trifluoromethyl and X is —OSO₂— into the corresponding compound of formula (I) wherein X is —O— by reaction with a compound of formula R1-OH (XIV) wherein R1 is an optionally substituted group selected from straight or branched (C₁-C₆) alkyl, (C₃-C₇) cycloalkyl, cycloalkylalkyl, aryl, arylalkyl, heterocyclyl and heterocyclylalkyl:

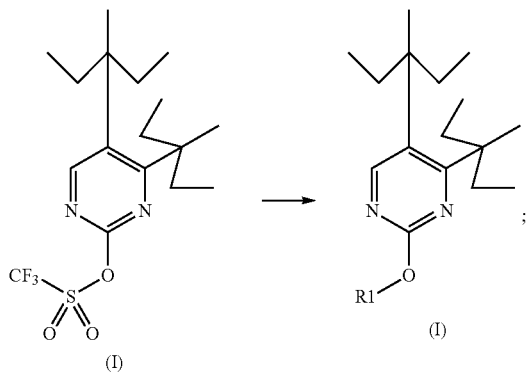

Conv. p) converting a compound of formula (I) wherein R1 is trifluoromethyl and X is —OSO₂— into the corresponding compound of formula (I) wherein X is —NR'— by reaction with a compound of formula R1-NHR' (XV) wherein R1 is as defined in formula (I) but not halogen and R' is as defined above:

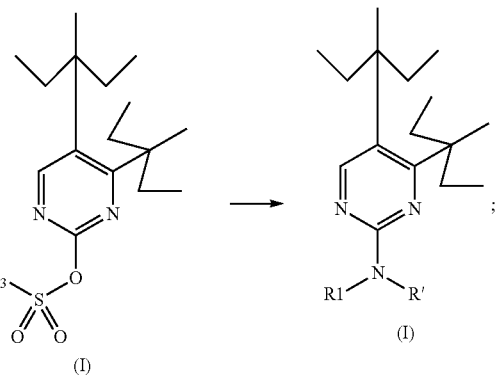

Conv. q) converting a compound of formula (I) wherein R1 is trifluoromethyl and X is —OSO₂— into the corresponding compound of formula (I) wherein X is —S— by reaction with a thiol of formula R1-SH (XVIII) wherein R1 is an optionally substituted group selected from straight or branched ($C_1$-$C_6$) alkyl, ($C_3$-$C_7$) cycloalkyl, cycloalkylalkyl, aryl, arylalkyl, heterocyclyl and heterocyclylalkyl:

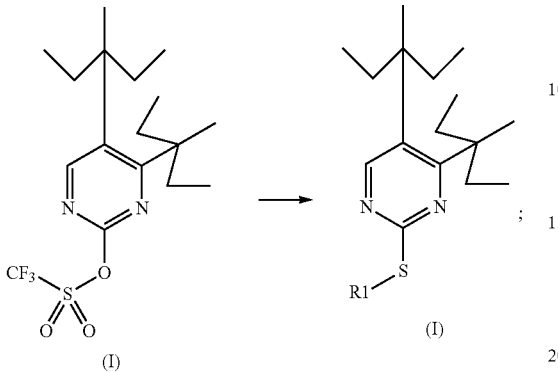

Conv. r) converting a compound of formula (I) wherein R1 is trifluoromethyl and X is —$OSO_2$— into the corresponding compound of formula (I) wherein X is a single bond by reaction with a compound of formula R1-Q (XIX) wherein R1 is an optionally substituted group selected from straight or branched ($C_1$-$C_6$) alkyl, ($C_3$-$C_7$) cycloalkyl, cycloalkylalkyl, aryl, arylalkyl, heterocyclyl and heterocyclylalkyl; and Q is a suitable group such as —$B(OH)_2$, —$B(OAlk)_2$, —$Sn(Alk)_4$, ZnHal, or MgHal, which can undergo palladium mediated carbon-carbon bond formation:

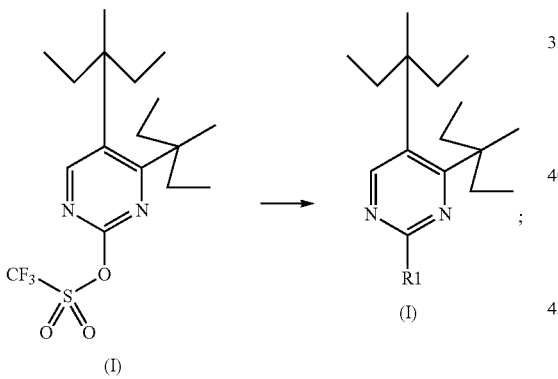

Conv. s) converting a compound of formula (I) wherein R3 is a $CONH_2$ group into the corresponding compound of formula (I) wherein R3 is CN, by reaction with a dehydrating agent:

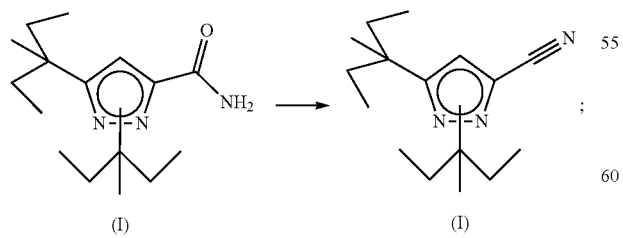

Conv. t) converting a compound of formula (I) wherein R4 is hydrogen into the corresponding compound of formula (I) wherein R4 is halogen, by reacting with an halogenating reagent:

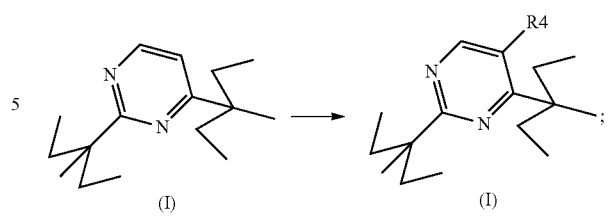

Conv. u) converting a compound of formula (I) wherein R4 is a group such as bromine or iodine, into the corresponding compound of formula (I) wherein R4 is CN, by palladium-catalyzed cyanation of aryl halides:

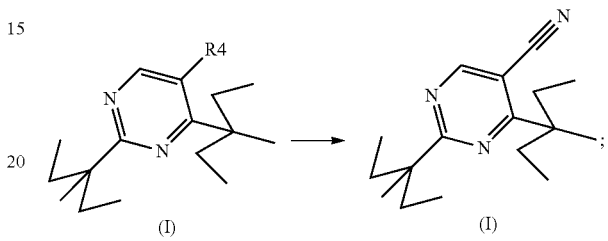

Conv. v) converting a compound of formula (I) wherein R1 is hydrogen and X is —NH— into the corresponding compound of formula (I) wherein R1 is iodine and X is a single bond, by reaction with iso-amylnitrite and diiodomethane or cesium iodide, in the presence of iodine and CuI:

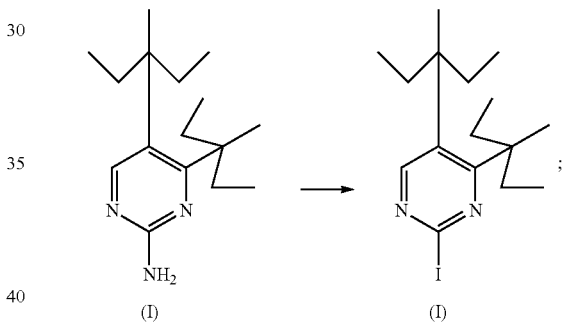

Conv. w) converting a compound of formula (I) wherein R1 is halogen and X is a single bond into the corresponding compound of formula (I) wherein X is —NH— and R1 is an optionally substituted aryl, by reaction with an optionally substituted arylamine of formula R1-NHR' (XV) wherein R1 is an optionally substituted aryl and R' is as defined above in the presence of palladium diacetate (Pd($OAc)_2$) and 2,2'-bis(diphenylphosphino)-1,1'-binaphthyl (BINAP):

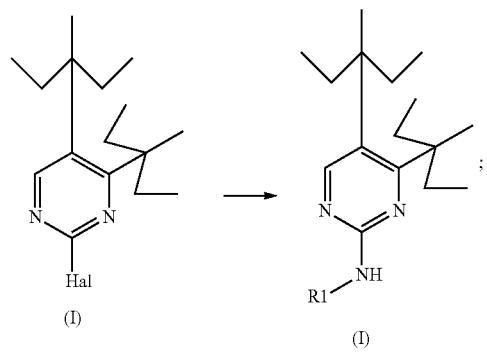

Conv. x) converting a compound of formula (I) wherein R1 is halogen and X is a single bond into the corresponding compound of formula (I) wherein X is single bond by reaction with a compound of formula (XIX):

R1-Q (XIX)

wherein R1 is or an optionally substituted group selected from straight or branched ($C_1$-$C_6$) alkyl, ($C_3$-$C_7$) cycloalkyl, cycloalkyl-alkyl, aryl, arylalkyl, heterocyclyl and heterocyclylalkyl and Q is a suitable group such as —B(OH)$_2$, —B(OAlk)$_2$, —Sn(Alk)$_4$, ZnHal, or MgHal, under palladium mediated carbon-carbon bond formation:

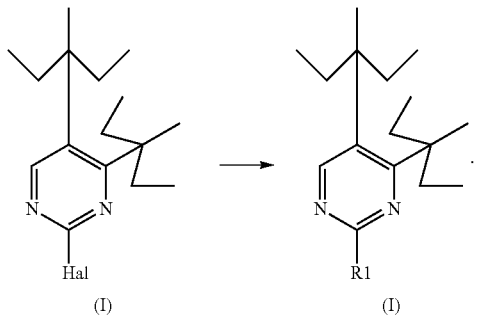

According to step 1 of the process, an α-carbonyl alkyne of formula (II) is reacted with an α-diazocarbonyl compound of formula (III). The 1,3-dipolar cycloaddition of diazocompounds and alkynes can be performed in a variety of ways and experimental conditions, according to conventional methods, which are widely known in the literature. The said reaction can be accomplished in a suitable solvent such as toluene, 1,4-dioxane, at a temperature ranging from room temperature (r.t.) to reflux for 2 to about 24 hours (h). Alternatively, the reaction can be performed in aqueous media such as water, in the presence of a Lewis acid catalyst such as InCl$_5$ (indium chloride) at r.t. for a time ranging from 4 to 24 h. Preferably, the above reaction is carried out with 3-butyn-2-one and ethyl α-diazoacetate in water at r.t. so to obtain a compound of formula (IVa) (Chem. Com., 2004, p. 394-395).

According to step 1a of the process, an α-carbonyl alkyne of formula (IIa) is reacted with an α-diazocarbonyl compound of formula (IIIa). The 1,3-dipolar cycloaddition of diazocompounds and alkynes can be performed as described under step 1 above.

According to step 2 of the process, a compound of formula (IVa) is dissolved in a suitable solvent for instance acetonitrile (CH$_3$CN), tetrahydrofuran (THF), N,N-dimethylformamide (DMF) or the like, and a suitable base such as sodium hydride, cesium carbonate or potassium carbonate is added therein. The compound of general formula (V) is then added and the mixture stirred for a time from about 2 h to about 15 h, at a temperature ranging from about 20° C. to about 80° C. Preferably, the reaction is carried out in the presence of K$_2$CO$_3$ in DMF so as to obtain a compound of formula (IVb) wherein R2" is as R2 but not hydrogen or aryl.

According to step 4b of the process, a compound of formula (IVb) is reacted as described under step 4a below.

According to step 3 of the process, the compound of formula (IVa) is reacted with a compound of formula (XVIa), in the presence of copper acetate and a base such as pyridine or the like, in a suitable solvent, for instance DCM, THF, dioxane or DMF, at a temperature ranging from r.t. to 100° C., and for a time ranging from 1 to about 48 h. Preferably, the reaction is carried out in the presence of pyridine in DCM at r.t. under an air atmosphere, so as to obtain a compound of formula (IVc) wherein R2'" is as R2 but not hydrogen.

According to step 4c of the process, a compound of formula (IVc) is reacted as described under step 4a below.

According to step 4a of the process, a compound of formula (IVa) wherein R3 is COOR5, is first hydrolyzed into the corresponding carboxylic acid derivative wherein R3 is COOH or their corresponding salts through basic or acidic hydrolysis conditions, widely known in the art. Preferably, the reaction is carried out with aqueous alkaline solutions such as aqueous lithium, sodium or potassium hydroxide in the presence of a suitable solvent such as a lower alcohol, THF, DMF or mixtures thereof; preferably the reaction is carried out with potassium hydroxide in EtOH, at a temperature ranging from about r.t. to about 80° C. According to the operative conditions being employed, the carboxylic acid derivative could be obtained either in its acidic form or, alternatively, as a salt. Then, the amidation of the carboxylic acid derivative to give the compound of formula (IVd) is carried out in the presence of ammonium chloride or a suitable primary or secondary amine of formula R"R'"NH (XII), under basic conditions, preferably with diisopropylethylamine (DIPEA) or triethylamine (TEA), in a suitable solvent such as DCM, DMF, THF, 1,4-dioxane, or dimethylacetamide (DMA), in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-Benzotriazole-1-yl)-1,1,3,3-tetramethyluronium hexafluorophosphate (HBTU). The said reaction is optionally carried out in the presence of a suitable catalyst such as the 4-dimethylaminopyridine, or in the presence of a further coupling reagent such as N-hydroxybenzotriazole.

Alternatively, the direct transformation of a compound of formula (IVa) wherein R3 is COOR5, into a compound of formula (IVd), can be performed according to methods well-known in the art to convert carboxyester groups (—COOEt) into carboxamides (—CONH$_2$), N-substituted carboxamides (—CONHR"), N,N-disubstituted carboxamides (—CONR"R'"). Preferably the reaction is carried out with ammonia in MeOH, at a temperature ranging from about 50° C. to about 100° C. Analogous operative conditions are applied in the preparation of N-substituted carboxamides or N,N-disubstituted carboxamides wherein a suitable primary or secondary amine are used in place of ammonia or ammonium hydroxide. Alternatively the same conversion may be obtained by reaction with ammonium chloride or a suitable primary or secondary amine of formula R"R'"NH (XII) in the presence of a base such as NaN(TMS)$_2$ or LiN(TMS)$_2$ in a suitable solvent, for instance Et$_2$O, THF or 1,4-dioxane, at a temperature ranging from −10° C. to 40° C., and for a time ranging from about 10 minutes (min) to about 12 h, so to obtain a compound of formula (IVd) wherein R3 is an amino group of formula —CONR"R'" or —CON(OR'")R". Preferably, the reaction is carried out in presence of LiN(TMS)$_2$ in THF at 0° C.

According to step 5 of the process, the synthesis of the enaminone derivative of formula (VI) is accomplished using a N,N-dimethylformamide-dialkylacetale, such as, for instance dimethylformamide-di-tert-butylacetale, dimethylformamide-diethylacetale and the like in a suitable solvent such as DMF, DMA, toluene, or the like at a temperature ranging from r.t. to 150° C., and for a time ranging from 30 min to about 24 h.

According to step 6 of the process, the compound of formula (VI) is reacted with a derivative of formula (VII) so to obtain a compound of formula (I) through pyrimidine ring formation in presence eventually of a base such as AcOK, $K_2CO_3$ or $Na_2CO_3$ in a suitable solvent such as, for instance, DMF, EtOH or toluene, at a temperature ranging from r.t. to reflux, and for a time ranging from about 1 to about 48 h. Preferably, the reaction is carried out in DMF at 120° C., for 18 h.

According to step 7 of the process, the compound of formula (VIII) is reacted with a derivative of formula (IX) to give a compound of formula (X). This reaction can be accomplished in a variety of ways and experimental conditions, according to conventional methods, which are widely known in the literature. Preferably the reaction is carried out in presence of an organic base such as lithium bis(trimethylsilyl) amide, sodium bis(trimethylsilyl)amide, sodium tert-butoxide or potassium tert-butoxide in a suitable solvent such as, for instance, THF or $Et_2O$, at a temperature ranging from −45° C. to r.t. and for a time varying from about 1 h to about 6 h.

According to step 8 of the process, the reaction of a compound of formula (X) with an hydrazine of formula (XI) or a salt thereof, can be carried out in a variety of ways, according to conventional methods, which are widely known in the literature. Preferably it is carried out using a compound of formula (XI) as hydrochloride and in presence of a base such as TEA or DIPEA, or an organic or inorganic salt such as sodium acetate, potassium acetate or sodium carbonate, in a suitable solvent such as, for instance, MeOH, EtOH, THF, pyridine or AcOH, at a temperature ranging from 80° C. to 130° C. and for a time varying from 2 h to overnight.

According to step 9 of the process, the compound of formula (XX) is reacted with an α-diazocarbonyl compound of formula (III). The 1,3 dipolar cycloaddition of diazocompounds and alkynes can be performed in a variety of ways and experimental conditions, according to conventional methods, which are widely known in the literature. The said reaction can be accomplished in a suitable solvent such as THF, toluene, 1,4 dioxane, at a temperature ranging from r.t. to reflux for 2 to about 24 h.

According to conversion (conv. a) of the process, a compound of formula (I) wherein R3 is COOR5 wherein R5 is an optionally substituted alkyl may be converted into the corresponding carboxylic acid derivative of formula (I) wherein R3 is COOH or a salt thereof, through basic or acidic hydrolysis conditions, widely known in the art. Preferably, the reaction is carried out with aqueous alkaline solutions such as aqueous lithium, sodium or potassium hydroxide in the presence of a suitable solvent such as a lower alcohol, THF, DMF or mixtures thereof; preferably the reaction is carried out with potassium hydroxide in THF/MeOH/water mixture, at a temperature ranging from about r.t. to about 80° C. According to the operative conditions being employed, the compound of formula (I) could be obtained either in its acidic form or, alternatively, as a salt.

According to conversion (conv. b) of the process, the amidation of a carboxylic acid of formula (I) wherein R3 is COOH to give the corresponding compound of formula (I) wherein R3 is (—CONR"R'") or (—CONR"OR'"), is carried out in the presence of ammonium chloride or a suitable primary or secondary amine of formula R"R'"NH (XII) or a substituted hydroxylamine derivative of formula R"NHOR'" (XIII), under basic conditions, preferably with DIPEA or TEA, in a suitable solvent such as DCM, DMF, THF, 1,4-dioxane, or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-benzotriazole-1-yl)-1,1,3,3-tetramethyluronium hexafluorophosphate (HBTU). The said reaction is optionally carried out in the presence of a suitable catalyst such as the 4-dimethylaminopyridine, or in the presence of a further coupling reagent such as N-hydroxybenzotriazole (HOBt). Alternatively, this same reaction is also carried out, for example through a mixed anhydride method, by using an alkyl chloroformate such as ethyl, iso-propyl, benzyl chloroformate, in the presence of a tertiary amine such as TEA, DIPEA, or pyridine, in a suitable solvent such as, for instance, toluene, DCM, THF, DMF and the like, at r.t.

According to (conv. c) of the process, the compound of formula (I) wherein R3 is COOR5 is transformed into the compound of formula (I) wherein R3 is (—CONR"R'") or (—CONR"OR'"), according to methods well-known in the art to convert carboxyester groups (—COOEt) into carboxamides (—$CONH_2$), N-substituted carboxamides (—CONHR'), N,N-disubstituted carboxamides (—CONR'R"). Preferably the reaction is carried out with ammonia in MeOH, at a temperature ranging from about 50° C. to about 120° C. Analogous operative conditions are applied in the preparation of N-substituted carboxamides or N,N-disubstituted carboxamides wherein a suitable primary or secondary amine are used in place of ammonia or ammonium hydroxide.

Alternatively the same conversion may be obtained by reacting the compound of formula (I) with ammonium chloride or a suitable primary or secondary amine of formula R"R'"NH (XII) or a substituted hydroxylamine derivative of formula R"NHOR'" (XIII), in the presence of a base such as NaN$(TMS)_2$ or LiN$(TMS)_2$ in a suitable solvent, for instance $Et_2O$, THF or dioxane, at a temperature ranging from −10° C. to 40° C., and for a time ranging from about 10 min to about 12 h, so to obtain another compound of formula (I) wherein R3 is an amido group of formula —CONR"R'" or —CON(OR'")R". Preferably, the reaction is carried out in the presence of LiN$(TMS)_2$ in THF at 0° C.

Alternatively, synthesis of amides from coupling esters with a range of primary amines of formula R"R'"NH (XII) can be conveniently achieved in the presence of DABAL-$Me_3$ [bis(trimethylaluminum)-1,4-diazabicyclo[2.2.2]octane adduct]. These reactions may be carried out in THF at a temperature ranging from r.t. to 40° C., and for a time ranging from about 10 min to about 12 h, so to obtain another compound of formula (I) wherein R3 is an amido group of formula —CONR"R'".

According to (conv. d) of the process, the oxidation of a compound of formula (I) wherein X is —S— into a compound of formula (I) wherein X is —S(O)$_2$— can be obtained by reaction with an oxidant agent well-known to those skilled in the art, such as for instance, oxone in a suitable solvent such as THF, 1,4-dioxane, acetone, optionally in the presence of water as co-solvent or m-chloroperbenzoic acid in the presence of a suitable solvent preferably DCM at r.t. and for a time ranging from about 1 to about 4 h.

According to (conv. e) of the process, a compound of formula (I) wherein R1 is or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl (I) and X is —O— may be easily obtained by reacting the corresponding sulfonyl derivative with a derivative of formula R1-OH (XIV). The reaction may be carried out in the presence of a base such as potassium or sodium carbonate, sodium or lithium hydroxide or the like, in a suitable solvent such as $CH_3CN$, DMF or dimethylsulfoxide (DMSO). By working at a temperature ranging from r.t. to about 100° C., and for a time ranging from about 1 to about 3 h.

According to (conv. f) of the process, a compound of formula (I) wherein R1 is an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; and X is —NR'—, wherein R' is as defined above, may be easily obtained by reacting the corresponding sulfonyl derivative with a derivative of formula R1-NHR' (XV). The said reaction is accomplished with an excess of the same amine or, alternatively, in a suitable solvent such as for instance $CH_3CN$, DMF, DMSO, and by working at a temperature ranging from r.t. to about 100° C., form 2 h to 24 h.

According to (conv. g) of the process, a compound of formula (I) wherein R1 is an optionally substituted group selected from straight or branched ($C_1$-$C_6$) alkyl, ($C_3$-$C_7$) cycloalkyl, cycloalkyl-alkyl, aryl, arylalkyl, heterocyclyl and heterocyclylalkyl; and X is —S—, may be easily obtained by reaction with a thiol of formula R1-SH (XVIII), wherein R1 is as defined above, in a suitable solvent such as THF, DMF, DCM, MeOH, DME or $CH_3CN$, at a temperature ranging from r.t. to 100° C., in a time ranging from 1 to 4 h.

According to conversion (conv. h) of the process, the transformation of the compound of formula (I), wherein R1 is Me and X is —S—, into the corresponding compound of formula (I), wherein R1 is an optionally substituted aryl and X is a single bond, is accomplished by reaction with a suitable organometal reagent, such as for instance an organoboronic acid of formula R1-$B(OH)_2$ (XVI). The reaction is a Pd-catalyzed Cu-mediated desulfitative C—C cross coupling, generally known as "Liebeskind-Srogl reaction". The said reaction is accomplished in the presence of a suitable palladium source such as, for instance, tetrakis triphenylphosphino palladium [$Pd(PPh_3)_4$] or the like, a copper$^{(I)}$-carboxylate as metal cofactor such as copper thiophen-2-carboxylate, in a suitable solvent such as THF, 1,4-dioxane, DMF, at reflux temperature, for a time ranging from 30 min to 6 h.

According to conversion (conv. i) of the process, the compound of formula (I) wherein R2 is a group selected from t-butyl, trityl, p-methoxybenzyl, m-methoxybenzyl and benzyl, may be converted into the corresponding compound of formula (I) wherein R2 is hydrogen atom by reaction in acidic conditions, for instance with AcOH, TFA or HCl or in basic conditions, for instance NaOH and in the presence of a suitable solvent such as MeOH, DCM or dioxane, at a temperature ranging from r.t. to reflux and for a time ranging from 1 to about 12 h.

According to conversion (conv. j) of the process, the conversion of a compound of formula (I) wherein R2 is hydrogen into the corresponding compound of formula (I), wherein R2 is as defined above but not hydrogen or aryl, can be accomplished using a compound of formula R2"-Y' (Va), wherein Y' is OH, in which case the Mitsunobu conditions can be employed, or wherein Y is a group that optionally upon activation may work as a leaving group, such as a halogen atom, or sulfonate group (e.g. —$OSO_2CF_3$, —$OSO_2CH_3$ or —$OSO_2PhMe$).

Therefore, in the former instance, when a Mitsunobu protocol is employed, the reaction can be accomplished using a dialkylazodicarboxylate, such as diethylazodicarboxylate (DEAD), diisopropylazodicarboxylate (DIAD) or the like, in the presence of a trialkyl or triaryl phosphine, preferably triphenyl phosphine in a suitable solvent such as THF, 1,4-dioxane, DME, $CH_3CN$.

Instead, when Y is a halogen or a group such as tosylate, mesylate or triflate or the like the conversion can be accomplished using a suitable base such as, for instance, NaH, $K_2CO_3$, $Cs_2CO_3$, DBU, KO-t-Bu and the like, in a suitable solvent such as THF, $CH_3CN$, DMF, DMA and the like. Said reactions can be carried out at temperatures ranging from 0° C. to reflux and for a time ranging from 30 min to about 48 h.

Interestingly, from these reactions a mixture of regioisomeric compounds is obtained: the resulting compounds of formula (Ia) and (Ib) can be conveniently separated into the single isomers and purified by known methods such as silica gel chromatography, preparative HPLC or crystallization.

According to conversion (conv. k) of the process, the conversion of a compound of formula (I) wherein R2 is hydrogen into the corresponding compound of formula (I) wherein R2 is as defined above but not hydrogen can be accomplished using a compound of formula R2'''—$B(OH)_2$ (XVIa). The reaction is a Cu-mediated N-arylation generally classified as Chan-Lam reaction (Tetrahedron Lett., 1998, 39, 2933-2936; Tetrahedron Lett., 1998, 39, 2941-2944). The said reaction is accomplished in the presence of a suitable copper source, such as for instance, copper$^{(II)}$ acetate, in the presence of 4 Å molecular sieves, using a suitable base such as TEA, pyridine, and a suitable solvent such as DCM, THF, and DMF, for a time ranging from 4 to 48 h. From this reaction a mixture of regioisomeric compounds is obtained and the resulting compounds of formula (Ia) and (Ib) can be conveniently separated into the single isomers and purified by known methods, such as silica gel chromatography, preparative HPLC or crystallization.

According to conversion (conv. l) of the process, replacement of bromine with —NR"R'" moiety can be achieved reacting the starting material with an amine of formula (XII) as defined above, in a suitable solvent such as THF or dioxane, and in the presence of catalytic amounts of $Pd_2(dba)_3$, 2-dicyclohexylphosphino-2'-(N,N-dimethylamino)-biphenyl and a base such as $LiN(TMS)_2$ at a temperature ranging from r.t. to reflux and for a time ranging from 1 to about 24 h.

According to conversion (conv. m) of the process, the compound of formula (I) as defined above is reacted with compounds of formula (XVII) as defined above according to conventional methods. As an example the reaction can be carried out in a suitable solvent such as DMF, DME, dioxane or $CH_3CN$ and in the presence of an optionally-substituted-aryliodide of formula (XVII) as defined above, catalytic amounts of $Pd_2(dba)_3$, BINAP or 2-(dicyclohexylphosphino)-2',4',6'-triisopropyl-1,1'-biphenyl (X-phos) and a base such as $K_2CO_3$, potassium phosphate or $Cs_2CO_3$, at a temperature ranging from r.t. to 110° C. and for a time ranging from 2 to about 24 h.

According to conversion (conv. n) of the process, a compound with a trifluoromethanesulfonyl group may be obtained by reacting the corresponding compound of formula (I) wherein X is —O— and R1 is hydrogen with a triflating agent such as trifluoromethanesulfonic anhydride, trifluoromethanesulfonylchloride or N-phenyl-bis(trifluoromethanesulfonimide), optionally in the presence of a base such as TEA or DIPEA, in a suitable solvent such as DCM, THF or 1,4-dioxane at a temperature ranging from –78° C. to r.t.

According to conversion (conv. o) of the process, a compound of formula (I), wherein R1 is an optionally substituted group selected from straight or branched ($C_1$-$C_6$) alkyl, ($C_3$-$C_7$) cycloalkyl, cycloalkyl-alkyl, aryl, arylalkyl, heterocyclyl and heterocyclylalkyl; and X is —O—, may be easily obtained by reacting the corresponding triflate derivative with a derivative of formula R1-OH (XIV). The reaction is carried out with an compound of formula (XIV), by operating in a suitable solvent such as 1,4-dioxane, THF, DME, CH$_3$CN, DMF or DMSO, at a temperature ranging from r.t. to about 90° C., optionally in the presence of a base such as K$_2$CO$_3$, potassium tert-butoxide or NaH.

Alternatively the reaction may be carried out in a suitable solvent such as toluene, DMF, DME or CH$_3$CN, in the presence of Pd(OAc)$_2$, (±)-BINAP and a base such as potassium phosphate or K$_2$CO$_3$ or Cs$_2$CO$_3$ at a temperature ranging from r.t. to 100° C.

According to conversion (conv. p) of the process, a compound of formula (I) wherein R1 is an optionally substituted group selected from straight or branched (C$_1$-C$_6$) alkyl, (C$_3$-C$_7$) cycloalkyl, cycloalkyl-alkyl, aryl, arylalkyl, heterocyclyl and heterocyclylalkyl; and X is —NR'— can be obtained reacting the corresponding trifluoromethanesulfonyl compound with an amine of formula R1-NHR' (XV). The reaction is typically obtained by operating in a suitable solvent such as dioxane, THF, DME, CH$_3$CN, DMF or DMSO, at a temperature ranging from r.t. to 150° C., optionally in the presence of a base such as K$_2$CO$_3$ or TEA.

Alternatively the reaction may be carried out in a suitable solvent such as toluene, DMF, DME or CH$_3$CN, in the presence of Pd(OAc)$_2$, (±)-BINAP and a base such as potassium phosphate or K$_2$CO$_3$ or Cs$_2$CO$_3$ at a temperature ranging from r.t. to 100° C.

According to conversion (conv. q) of the process, a compound of formula (I) wherein R1 is an optionally substituted group selected from straight or branched (C$_1$-C$_6$) alkyl, (C$_3$-C$_7$) cycloalkyl, cycloalkyl-alkyl, aryl, arylalkyl, heterocyclyl and heterocyclylalkyl; and X is —S—, can be obtained from the corresponding trifluoromethanesulfonyl compound. The conversion is carried out by reaction with a thiol of formula R1-SH (XVIII) in a suitable solvent such as THF, DMF, DCM, MeOH, DME or CH$_3$CN, at a temperature ranging from r.t. to 100° C.

According to conversion (conv. r) of the process, a compound of formula (I) wherein R1 is an optionally substituted group selected from straight or branched (C$_1$-C$_6$) alkyl, (C$_3$-C$_7$) cycloalkyl, cycloalkyl-alkyl, aryl, arylalkyl, heterocyclyl and heterocyclylalkyl; can be obtained by reaction of the corresponding trifluoromethanesulfonyl with a derivative of formula R1-Q (XIX) in a suitable solvent such as DMF, DCM, MeOH, DME or CH$_3$CN, in the presence of Pd$_2$(dba)$_3$, PdCl$_2$(dppf) or Pd(PPh$_3$)$_4$, optionally in the presence of cesium fluoride or cesium carbonate, at a temperature ranging from r.t. to 100° C.

According to conversion (conv. s) of the process, a compound of formula (I) wherein R3 is CONH$_2$ is converted into the corresponding compound of formula (I) wherein R3 is CN, by reacting with a dehydrating agent such as POCl$_3$, in a suitable solvent such as toluene at a temperature ranging from r.t. to reflux for 2 to about 6 h. Alternatively, the same conversion is performed by using a catalytic amount of palladium$^{(II)}$ acetate in CH$_3$CN (Org. Lett. 2005, 7, 5237-39), from r.t. to reflux for about 2 to 6 h.

According to conversion (conv. t) of the process, a compound of formula (I) wherein R4 is hydrogen can be transformed into the corresponding compound of formula (I) wherein R4 is bromine or iodine. The said reaction is performed with a halogenating reagent such as NBS and NIS, in a suitable solvent such as DCM or DMF, from −10° C. to r.t. within 2 to about 18 h. Preferably, the reaction is carried out under neutral conditions in the presence of iodine and silver trifluoroacetate, in DCM at a temperature ranging from 0° C. to 18° C. and for a time ranging from 5 h to overnight.

According to conversion (conv. u) of the process, a compound of formula (I) wherein R4 is bromine or iodine can be converted into the corresponding compound of formula (I) wherein R4 is CN, following the conditions reported for palladium-catalyzed cyanation of aryl halides. The said reaction is performed by using ZnCN or potassium hexacyanoferrate$^{(II)}$ as a source of cyanide in the presence of palladium$^{(II)}$ acetate as catalyst, sodium carbonate, potassium carbonate or cesium carbonate as base, in a suitable solvent such as DMF, N-methylpyrrolidone, or DMA, from 80° C. to reflux, for a time ranging from 4 to about 24 h (J. Org. Chem. 2005, 70, 1508-1510, Org. Lett., 2011, 13 (4), pp 648-651).

According to conversion (conv. v) of the process, a compound of formula (I) wherein R1 is iodine and X is a single bond may be prepared by the corresponding compound of formula (I) wherein R1 is hydrogen and X is —NH—; the reaction is carried out using iso-amylnitrite and diiodomethane or cesium iodide, in the presence of iodine and CuI in a suitable solvent such as THF, Et$_2$O or DME, at a temperature ranging from r.t. to about 70° C., and for a time of about 8 h to about 48 h.

According to conversion (conv. w) of the process, a compound of formula (I) wherein R1 is an optionally substituted aryl and X is —NH— may be obtained reacting the corresponding halogen derivative with a compound of formula R1-NHR' (XV), in a suitable solvent such as DMF, DME or CH$_3$CN and in the presence of catalytic amounts of Pd(OAc)$_2$, BINAP or Xantphos and a base such as K$_2$CO$_3$, potassium phosphate or Cs$_2$CO$_3$, at a temperature ranging from r.t. to 110° C. and for a time ranging from about 2 to about 24 h.

According to conversion (conv. x) of the process, a compound of formula (I) wherein R1 is an optionally substituted group selected from straight or branched (C$_1$-C$_6$) alkyl, (C$_3$-C$_7$) cycloalkyl, cycloalkyl-alkyl, aryl, arylalkyl, heterocyclyl and heterocyclylalkyl; and X is a single bond, may be obtained exploiting any of the cross-coupling reactions suitable for the formation of carbon-carbon bonds. Said reactions, which are well known in the art, imply coupling with a suitable organometal reagent such as for instance organoboron (Suzuki reaction), organotin (Stille reaction), organomagnesium (Kumada reaction), or organozinc (Negishi reaction) and the like. Preferred reaction is the Suzuki reaction where the appropriate aryl or heteroharylboronic derivative is used in the presence of a palladium based catalyst such as PdCl$_2$(dppf)$_2$.CH$_2$Cl$_2$ or Pd$_2$(dba)$_3$ or Pd(PPh$_3$)$_4$, in a suitable solvent such as DMF, DCM, MeOH, CH$_3$CN, or in a mixture of solvents, such as DME and water, optionally in the presence of a base such as sodium, cesium carbonate or cesium fluoride, at a temperature ranging from r.t. to 100° C.

Needless to say, also any of the intermediates of the above described processes could be converted into a different intermediate, if wanted and necessary, by operating in an analogous way as in any one of the conversion reaction here above described.

From all of the above, it is clear to the skilled person that any compound of formula (I) bearing a functional group which can be further derivatized to another functional group, by working according to methods well known in the art thus leading to other compounds of formula (I), is intended to be comprised within the scope of the present invention. It is known to the skilled person that conversion of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (NY), 1999.

According to any variant of the process for preparing the compounds of formula (I), the starting materials and any other reactants are known or easily prepared according to known methods.

The compound of formula (VIII) can be prepared as described in EP1785418A1 and WO2005/14572A1.

The compounds of formula (II), (IIa), (III), (IIIa), (VII), (IX), (XI), (XII), (XIII), (XIV), (XV), (XVI), (XVII), (XVIII), (XIX), are either commercially available or can be prepared with known methods.

The compounds of formula (V), (Va) and (XVIa) are either commercially available or can be prepared with known methods or, in particular compounds of formula (XVIa), can be prepared as described in the experimental part below (Preparation K).

Compounds of formula (XX) can be prepared with known methods as described in J. Med. Chem., 2004, vol 47 p. 4716-4730; Org. Lett., 2006, 8 (2), pp 269-272; or as described in the experimental part (Preparation L).

From all of the above, it is clear to the skilled person that when preparing the compounds of formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I), is within the scope of the present invention.

Conventional techniques for racemate resolution include, for instance, partitioned crystallization of diastereoisomeric salt derivatives or preparative chiral HPLC.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight and conditions of the patient and upon administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form of tablets, capsules, sugar or film coated tablets, liquid solutions or suspensions; rectally, in the form of suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manners, for example, by means of mixing, granulating, tabletting, sugar-coating, or film-coating processes.

The liquid dispersions for oral administration may be, for instance, syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

With the aim at better illustrating the present invention, without posing any limitation to it, a number of examples will be given in the experimental section.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein, as well as throughout the description, have the following meaning:

| ABBREVIATIONS | |
|---|---|
| AcOEt | ethyl acetate |
| AcOH | acetic acid |
| AcONa | sodium acetate |
| AcOK | potassium acetate |
| BINAP | 2,2'-bis(diphenylphosphino)-1,1'-binaphthyl |
| $CH_3CN$ | acetonitrile |
| $Cs_2CO_3$ | cesium carbonate |
| CuTC | copper(I) thiophencarboxylate |
| CuI | copper(I) iodide |
| DCC | N,N'-dicyclohexylcarbodiimide |
| DCM | dichloromethane |
| DIPEA | N,N-diisopropyethylamine |
| DMA | N,N-dimethylacetamide |
| DME | 1,2-dimethoxyethane |
| DMF | N,N-dimethylformamide |
| DMSO | dimethyl sulfoxide |
| EDCl | N-ethyl-N',N'-diisopropyl carbodiimide hydrochloride |
| $Et_2O$ | diethyl ether |
| EtOH | ethanol |
| HCl | hydrochloric acid |
| HOBt | 1H-benzotriazol-1-ol |
| $InCl_3$ | indium chloride |
| $K_2CO_3$ | potassium carbonate |
| $K_3PO_4$ | potassium phosphate |
| $KH_2PO_4$ | potassium dihydrogen phosphate |
| KOH | potassium hydroxide |
| $LiN(TMS)_2$ | lithium bis(trimethylsilyl)amide |
| LiOH | litium hydroxide |
| mCPBA | m-chloroperbenzoic acid |
| MeOH | methanol |
| $Na_2CO_3$ | sodium carbonate |
| $Na_2SO_4$ | sodium sulfate |
| NaH | sodium hydride |
| $NaH_2PO_4$ | sodium dihydrogen phosphate |
| $NaHCO_3$ | sodium hydrogen carbonate |
| NaOH | sodium hydroxide |
| $Pd(OAc)_2$ | palladium(II) acetate |
| $Pd(PPh_3)_4$ | tetrakis (triphenylphosphine) palladium |
| $Pd_2(dba)_3$ | tris(dibenzylideneacetone)dipalladium(0) |
| $PdCl_2(dppf)$ | [1,1'-bis(diphenylphosphino)ferrocene]palladium(II) chloride |
| PyBOP | (benzotriazol-1-yloxy)tripyrrolidinophosphonium hexafluorophosphate |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |
| Xantphos | 4,5-bis(diphenylphosphino)-9,9-dimethylxanthene |
| h | hour/s |
| min | minute/s |
| r.t. | room temperature |
| Rt | retention time |

General Purification and Analytical Methods

The synthetic preparation of some compounds of formula (I) of the invention is described in the following examples.

The compounds of the present invention, as prepared according to the following examples, were also characterized by $^1H$ NMR and/or by HPLC/MS analytical data; HPLC/MS data were collected following any one of methods 1, 2, 3 and 4.

HPLC/MS Analytic Method 1

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 μm Waters Acquity UPLC (2.1×50 mm) column. Mobile phase A was formic acid 0.1% pH=3.3 buffer with $CH_3CN$ (98:2), and mobile phase B was $H_2O/CH_3CN$ (5:95); the gradient was from 5 to 95% B in 2 min then hold 95% B 0.1 min. The injection volume was 2 μL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 2

HPLC-MS analyses were performed on a Finnigan MAT mod. LCQ ion trap mass spectrometer, equipped with an electrospray (ESI) ion source; the mass spectrometer is directly connected to a HPLC SSP4000 (Thermo Separation) equipped with an autosampler Lc Pal (CTC Analytics) and an UV6000LP PDA detector.

HPLC was carried out at 40° C. at a flow rate of 1.0 mL/min using a Phenomenex Gemini C18, 3 μm, 50×4.6 mm column. Mobile phase A was acetate buffer 5 mM pH 4.5:$CH_3CN$ 95:5 (v:v), and mobile phase B was acetate buffer 5 mM pH 4.5: $CH_3CN$ 5:95 (v:v); the gradient was from 0 to 100% B in 7 min then hold 100% B for 2 min before re-equilibration. Total LC time was 10 min. The injection volume was 10 μL.

MS conditions: the LCQ mass spectrometer operates with an electrospray ionization (ESI) interface in positive and negative ion mode. ESI sprayier voltage 4.0 kV, heated capillary temperature 255° C., sheath gas nitrogen with a pressure of 5.0 Bar. A full scan detection mode (from 50 to 1000 amu) was used.

MS/MS experiments were performed on the most intense ion of each scan automatically by Xcalibur software. A 45% collision energy was used for the fragmentation of the precursor ions.

HPLC/MS Analytic Method 3

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 30° C. at a flow rate of 1.0 mL/min using a C18, 3 μm Phenomenex (4.6×50 mm) column. Mobile phase A was ammonium acetate 5 mM pH=5.2 buffer with $CH_3CN$ (95:5), and mobile phase B was $H_2O/CH_3CN$ (5:95); the gradient was from 10 to 90% B in 8 min then ramp to 100% B in 1.0 min. The injection volume was 10 μL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 1.0 mL/min using a RP18 Waters X Terra (3.0×20 mm) column. Mobile phase A was ammonium hydroxide 0.05% pH=10 buffer with CH₃CN (95:5), and mobile phase B was H₂O/CH₃CN (5:95); the gradient was from 10 to 90% B in 4 min then hold 90% B 1 min. The injection volume was 10 μL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of formula (I) of the invention, as prepared according to the following examples, were purified by preparative HPLC.

The operative conditions are defined below:
HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 μm (19×250 mm) column. Mobile phase A was ammonium hydroxide 0.05% pH=10 buffer with CH₃CN (95:5), and mobile phase B was CH₃CN; the gradient was from 10 to 90% B in 15 min then hold 90% B 3 min. The injection volume was 10 μL.

The mass spectrometer was operated in positive and in negative ion mode, the capillary voltage was set up at 2.5 KV; the source temperature was 120° C.; cone was 10 V; full scan, mass range from 100 to 800 amu was set up.
HPLC/MS Preparative Method 2

The HPLC equipment consisted of a Waters 2790 HPLC system equipped with 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 μm (19×250 mm) column. Mobile phase A was 0.1% TFA in water/CH₃CN (95:5), and mobile phase B was CH₃CN; the gradient was from 10 to 90% B in 15 min then hold 90% B 3 min. The injection volume was 10 μL.

The mass spectrometer was operated in positive and in negative ion mode, the capillary voltage was set-up at 2.5 KV; the source temperature was 120° C.; cone was 10V; full scan, mass range from 100 to 800 amu was set up.
MS Exact Exact mass data ESI(+) were obtained on a Waters Q-T of Ultima directly connected with micro HPLC 1100 Agilent as previously described (M. Colombo, F. Riccardi-Sirtori, V. Rizzo, Rapid Commun. Mass Spectrom. 2004, 18, 511-517).
NMR ¹H-NMR spectra were recorded at a constant temperature of 28° C. on a Varian INOVA 400 spectrometer operating at 400.50 MHz and equipped with a 5 mm z-axis PFG Indirect Detection Probe (¹H{¹⁵N-³¹P}). Alternatively, a Varian INOVA 599.88 MHz equipped with a 5 mm z-axis PFG Indirect Detection Probe ¹H, ¹⁹F, was also used.

Chemical shifts were referenced with respect to the residual solvent signals (DMSO-d₆: 2.50 ppm for ¹H, where not otherwise specified). Data are reported as follows: chemical shift (δ), multiplicity (s=singlet, d=doublet, t=triplet, q=quartet, br. s=broad singlet, td=triplet of doublets, dd=doublet of doublets, ddd=doublet of doublets of doublets, m=multiplet, spt=septet), coupling constants (J, Hz), and number of protons.

EXAMPLES

Preparation A

Ethyl 5-acetyl-1H-pyrazole-3-carboxylate [(IVa) R2'=H, R3=COOEt]

Step 1

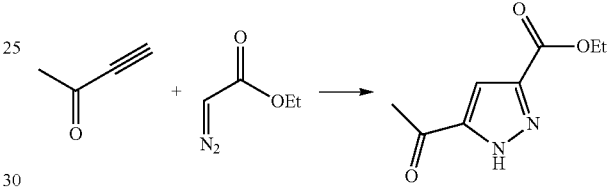

To a solution of InCl₃ (0.652 g, 2.94 mmol) in H₂O (30 mL) was added ethyl diazoacetate (1.7 mL, 16.16 mmol) and but-3-yn-2-one (1.0 g, 14.68 mmol). The reaction mixture was capped and stirred at r.t. for 4 h and extracted with Et₂O. The organic phase was dried on Na₂SO₄ and concentrated to dryness. The crude was purified by chromatography on a silica gel column (eluent: DCM/EtOH: 30/1) to afford 2.08 g (78% yield) as a white solid.

¹H NMR (401 MHz, DMSO-d₆) δ ppm 14.58 (br. s., 1H), 14.42 (br. s., 1H), 7.45 (d, J=1.83 Hz, 1H), 7.16 (d, J=1.71 Hz, 1H), 4.25-4.39 (m, 2H), 2.52 (d, J=0.73 Hz, 3H), 1.31 (dt, J=5.25, 7.02 Hz, 3H)

HRMS (ESI) calcd for C₈H₁₁N₂O₃ [M+H]⁺ 183.0764. found 183.0771.
Preparation B

5-Acetyl-N-(2,6-diethylphenyl)-1H-pyrazole-3-carboxamide [(IVd) R2'=H, R''=H, R'''=2,6-diethylphenyl]

Step 4a
Step 4a/1
Preparation of 5-acetyl-1H-pyrazole-3-carboxylic acid

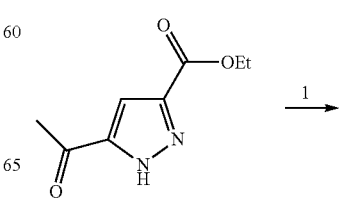

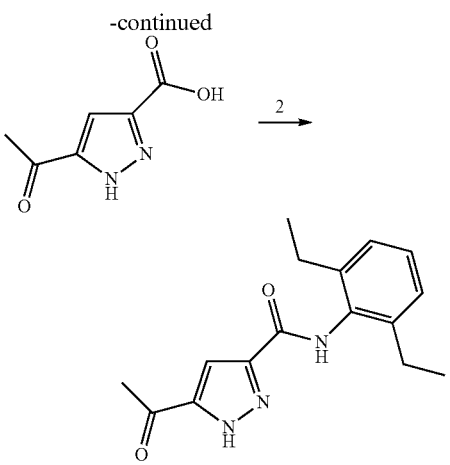

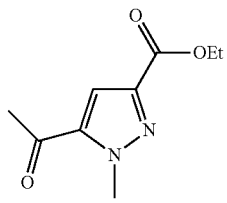

Ethyl 5-acetyl-1H-pyrazole-3-carboxylate (0.050 g, 0.274 mmol) was dissolved in EtOH (5 mL) and treated with a 2 M solution of NaOH (0.5 mL, 1 eq.) at reflux temperature for 3 h. Solvent was evaporated to dryness and the residue dissolved in H$_2$O. After treatment with 2M HCl the resulting precipitate was extracted with DCM. The organic phase was dried on Na$_2$SO$_4$ and concentrated to dryness to give the title compound (37 mg, 87% yield) as a white solid.

$^1$H NMR (400 MHz, DMSO-d$_6$) δ ppm 14.51-14.22 (m, 1H), 13.73-12.73 (m, 1H), 7.02-7.43 (m, 1 H), 2.51 (s, 3 H)

HRMS (ESI) calcd for C$_6$H$_7$N$_2$O$_3$[M+H]$^+$ 155.0451. found 155.0452.

Step 4a/2

A suspension of 5-acetyl-1H-pyrazole-3-carboxylic acid (0.035 g, 0.227 mmol) in anhydrous DMF (3 mL) was treated with HOBt (0.060 g, 0.443 mmol), EDCI (0.087 g, 0.454 mmol), 2,6-diethylaniline (0.090 mL, 0.575 mmol) and DIPEA (0.060 mL, 0.345 mmol). The reaction was stirred at 70° C. overnight. The reaction was diluted with water, extracted with AcOEt (2×20 mL). The organic fractions were combined, dried over Na$_2$SO$_4$, filtered and concentrated in vacuo. Purification by flash chromatography on silica gel (eluant: AcOEt/hexane 2/8) provided 0.020 g (30% yield) of the title compound.

$^1$H NMR (400 MHz, DMSO-d$_6$) δ ppm 14.32 (br. s., 1 H), 9.58-10.07 (m, 1 H), 7.42-7.56 (m, 1 H), 7.20-7.29 (m, 1 H), 7.09-7.19 (m, 2 H), 2.51-2.57 (m, 7 H), 0.94-1.18 (m, 6 H)

HRMS (ESI) calcd for C$_{16}$H$_{20}$N$_3$O$_2$ [M+H]$^+$ 286.1550. found 286.1551.

Preparation C

Ethyl 3-acetyl-1-methyl-1H-pyrazole-5-carboxylate [(IVb) R2″=Me, R3=COOEt] and ethyl 5-acetyl-1-methyl-1H-pyrazole-3-carboxylate [(IVb) R2″=Me, R3=COOEt]

Step 2

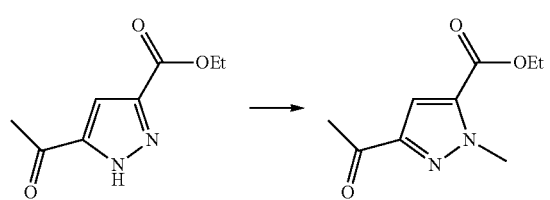

To a solution of ethyl 5-acetyl-1H-pyrazole-3-carboxylate (0.050 g, 0.274 mmol) in DMF (3 mL), Cs$_2$CO$_3$ (0.134 g, 0.412 mmol) and methyl iodide (0.022 mL, 0.357 mmol) were added. The reaction was continued at r.t. overnight then AcOEt (20 mL) was added and the organic phase washed with water (20 mL). The aqueous fraction was extracted with AcOEt (20 mL). The organic fractions were combined, dried over Na$_2$SO$_4$, filtered, and concentrated in vacuo. Purification by flash chromatography on silica gel (eluant: AcOEt/hexane 2/8) provided 37 mg (68% yield) of ethyl 3-acetyl-1-methyl-1H-pyrazole-5-carboxylate.

$^1$H NMR (400 MHz, DMSO-d$_6$) δ ppm 7.21 (s, 1 H), 4.32 (q, J=7.14 Hz, 2 H), 4.17 (s, 3 H), 2.50 (s, 3 H), 1.32 (t, J=7.14 Hz, 3 H)

HRMS (ESI) calcd for C$_9$H$_{13}$N$_2$O$_3$ [M+H]$^+$ 197.0921. found 197.0928;

and 5 mg (9% yield) of ethyl 5-acetyl-1-methyl-1H-pyrazole-3-carboxylate:

$^1$H NMR (400 MHz, DMSO-d$_6$) δ ppm 7.59 (s, 1 H), 4.30 (q, J=7.08 Hz, 2 H), 4.10 (s, 3 H), 2.54 (s, 3 H), 1.30 (t, J=7.08 Hz, 3 H)

HRMS (ESI) calcd for C$_9$H$_{13}$N$_2$O$_3$ [M+H]$^+$ 197.0921. found 197.0929.

According to this same methodology, but employing suitable substituted derivatives, the following compounds were prepared:

ethyl 5-acetyl-1-(3-methoxybenzyl)-1H-pyrazole-3-carboxylate (26% yield)

[(IVb) R2″=3-methoxybenzyl, R3=COOEt]

LC/MS (254 nm) HPLC method 2: Rt 5.46 min $^1$H NMR (500 MHz, DMSO-d$_6$) δ ppm 7.69 (s, 1 H), 7.23 (t, J=7.8 Hz, 1 H), 6.84 (dd, J=8.4, 2.6 Hz, 1 H), 6.69 (s, 1 H), 6.64 (d, J=7.7 Hz, 1 H), 5.72 (s, 2 H), 4.31 (q, J=7.1 Hz, 2 H), 3.71 (s, 3 H), 2.55 (s, 3 H), 1.30 ppm (t, J=7.0 Hz, 3 H)

HRMS (ESI) calcd for C$_{16}$H$_{19}$N$_2$O$_4$ [M+H]$^+$ 303.1340. found 303.1344.

Ethyl 3-Acetyl-1-(3-methoxy-benzyl)-1H-pyrazole-5-carboxylate (63% yield)

[(IVb) R2″=3-methoxybenzyl, R3=COOEt]

LC/MS (254 nm) HPLC method 2: Rt 5.85 min $^1$H NMR (500 MHz, DMSO-d$_6$) δ ppm 7.30 (s, 1 H), 7.25 (t, J=7.8 Hz, 1 H), 6.86 (dd, J=8.2, 2.5 Hz, 1 H), 6.75 (s, 1 H), 6.70 (d, J=7.7 Hz, 1 H), 5.77 (s, 2 H), 4.29 (q, J=7.1 Hz, 2 H), 3.71 (s, 3 H), 2.50 (s, 3 H), 1.26 (t, J=7.0 Hz, 3 H)

HRMS (ESI) calcd for C$_{16}$H$_{19}$N$_2$O$_4$ [M+H]$^+$ 303.1340. found 303.1342.

Preparation D 5-acetyl-1-(3-methoxybenzyl)-1H-pyrazole-3-carboxamide [(IVe) R2"=3-methoxybenzyl, R"=R'"=H] and 3-acetyl-1-(3-methoxybenzyl)-1H-pyrazole-5-carboxamide [(IVe) R2"=3-methoxybenzyl, R"=R'"=H]

Step 2a

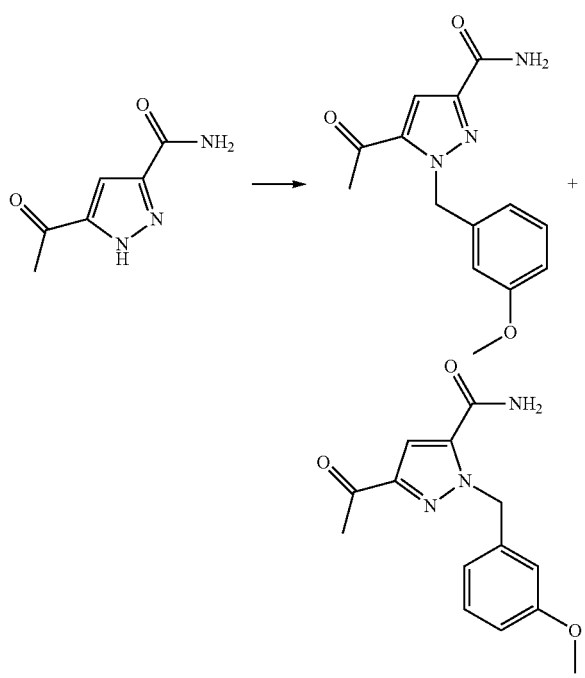

To a solution of 5-acetyl-1H-pyrazole-3-carboxamide (400 mg, 2.61 mmol) and cesium carbonate (1.0 g, 3 mmol) in 5 mL DMF at r.t., 1-chloromethyl-3-methoxy-benzene (430 μl, 4.3 mmol, 1.078 g/mL) was added. The mixture was stirred for 2 h. The volatiles were removed under vacuum, the residue was diluted with AcOEt and washed with brine. The organic phase was dried with sodium sulfate, filtered, and concentrated. The crude material was purified by silica gel column chromatography eluting with DCM and MeOH (98:2) to give both isomers.

5-Acetyl-1-(3-methoxy-benzyl)-1H-pyrazole-3-carboxylic acid amide (46% yield)

LC/MS (254 nm) HPLC method 2: Rt 3.93 min
$^1$H NMR (500 MHz, DMSO-$d_6$) δ ppm 7.73 (br. s., 1 H), 7.56 (s, 1 H), 7.43 (br. s., 1 H), 7.22 (t, J=8.0 Hz, 1 H), 6.84 (dd, J=8.1, 2.3 Hz, 1 H), 6.69 (d, J=1.9 Hz, 1 H), 6.59-6.68 (m, 1 H), 5.67 (s, 2 H), 3.71 (s, 3 H), 2.53 (s, 3 H)
HRMS (ESI) calcd for $C_{14}H_{16}N_3O_3$ [M+H]$^+$ 274.1186, found 274.1193.

3-acetyl-1-(3-methoxybenzyl)-1H-pyrazole-5-carboxamide (35% yield)

LC/MS (254 nm) HPLC method 2: Rt 4.06 min
$^1$H NMR (500 MHz, DMSO-$d_6$) δ ppm 8.13 (s, 1 H), 7.69 (br. s., 1 H), 7.39 (s, 1 H), 7.23 (t, J=8.0 Hz, 1 H), 6.84 (dd, J=8.2, 2.5 Hz, 1 H), 6.74 (d, J=1.9 Hz, 1 H), 6.71 (d, J=7.7 Hz, 1 H), 5.81 (s, 2 H), 3.71 (s, 3 H), 2.48 (s, 3 H)
HRMS (ESI) calcd for $C_{14}H_{16}N_3O_3$ [M+H]$^+$ 274.1186, found 274.1180.

According to this same methodology, but employing suitable substituted derivatives, the following compounds were prepared:

3-acetyl-N-(2,6-diethylphenyl)-1-methyl-1H-pyrazole-5-carboxamide [(IVe) R2"=Me, R"=2,6-diethylphenyl, R'"=H]

$^1$H NMR (400 MHz, DMSO-$d_6$) δ ppm 9.90 (s, 1 H), 7.51 (s, 1 H), 7.28-7.21 (m, 1H), 7.19-7.13 (m, 2H), 4.16 (s, 3 H), 2.54 (q, J=7.57 Hz, 4 H), 2.52 (s, 3 H), 1.11 (t, J=7.57 Hz, 6 H)
HRMS (ESI) calcd for $C_{17}H_{22}N_3O_2$ [M+H]$^+$ 300.1707, found 300.1708.

5-acetyl-N-(2,6-diethylphenyl)-1-methyl-1H-pyrazole-3-carboxamide [(IVe) R2"=Me, R"=2,6-diethylphenyl, R'"=H]

$^1$H NMR (400 MHz, DMSO-$d_6$) δ ppm 9.72 (s, 1 H), 7.59 (s, 1H), 7.28-7.17 (m, 1H), 7.17-7.06 (m, 2H), 4.15 (s, 3 H), 2.56 (s, 3 H), 2.51-2.55 (m, 4 H), 1.09 (t, J=7.57 Hz, 6 H)
HRMS (ESI) calcd for $C_{17}H_{22}N_3O_2$ [M+H]$^+$ 300.1707, found 300.1709.

5-acetyl-N-(2,6-diethylphenyl)-1-(4-methoxybenzyl)-1H-pyrazole-3-carboxamide [(IVe) R2"=4-methoxybenzyl, R"=2,6-diethylphenyl, R'"=H]

$^1$H NMR (400 MHz, DMSO-$d_6$) δ ppm 9.76 (s, 1H), 7.66 (s, 1H), 7.18-7.27 (m, 3H), 7.10-7.17 (m, 2H), 6.87-6.92 (m, 2H), 5.69 (s, 2H), 3.72 (s, 3H), 2.55 (s, 3H), 2.51-2.55 (m, 4H), 1.10 (t, J=7.51 Hz, 6H)
HRMS (ESI) calcd for $C_{24}H_{28}N_3O_3$ [M+H]$^+$ 406.2125, found 406.2124.

3-acetyl-N-(2,6-diethylphenyl)-1-(4-methoxybenzyl)-1H-pyrazole-5-carboxamide [(IVe) R2"=4-methoxybenzyl, R"=2,6-diethylphenyl, R'"=H]

$^1$H NMR (400 MHz, DMSO-$d_6$) δ ppm 9.91 (s, 1H), 7.49 (s, 1H), 7.19-7.26 (m, 1H), 7.10-7.18 (m, 4H), 6.86-6.91 (m, 2H), 5.75 (s, 2H), 3.72 (s, 3H), 2.54 (s, 3H), 2.42 (q, J=7.57 Hz, 4H), 1.04 (t, J=7.57 Hz, 6H)
HRMS (ESI) calcd for $C_{24}H_{28}N_3O_3$ [M+H]$^+$ 406.2125, found 406.2137.

Preparation E

3-Acetyl-N-(2,6-diethylphenyl)-1-methyl-1H-pyrazole-5-carboxamide [(IVe) R2"=Me, R"=2,6-diethylphenyl, R'"=H]]

Step 4b

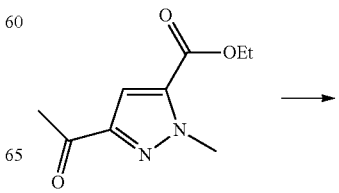

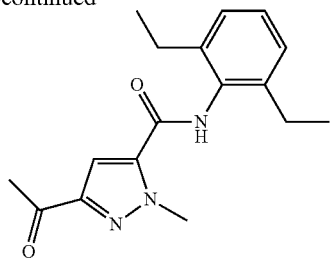

To a solution of 2,6-diethylaniline (0.272 mL, 1.653 mmol) in 3 mL of anhydrous THF under argon, 1M solution of NaN(TMS)$_2$ in THF (1.90 mL, 1.90 mmol) at 0° C. were added dropwise. The mixture was stirred at 0° C. for 0.5 h then ethyl 3-acetyl-1-methyl-1H-pyrazole-5-carboxylate (0.162 g, 0.827 mmol) in 2.5 mL of anhydrous THF at 0° C. were added dropwise. Ice bath was removed and the mixture was stirred at r.t. for 1 h. H$_2$O (20 mL) was added and the mixture was extracted with AcOEt (2×30 mL). The organic layer was dried over anhydrous Na$_2$SO$_4$ and the solvent evaporated to dryness. The crude solid was purified by flash chromatography on silica gel (eluant: AcOEt/hexane 5/95) to afford 0.097 g (40% yield) of the title compound.

$^1$H NMR (400 MHz, DMSO-d$_6$) δ ppm 9.90 (s, 1 H), 7.51 (s, 1 H), 7.21-7.28 (m, 1 H), 7.13-7.19 (m, 2 H), 4.16 (s, 3 H), 2.54 (q, J=7.57 Hz, 4 H), 2.52 (s, 3 H), 1.11 (t, J=7.57 Hz, 6 H)

HRMS (ESI) calcd for C$_{17}$H$_{22}$N$_3$O$_2$ [M+H]$^+$ 300.1707. found 300.1708.

According to this same methodology, but employing suitable substituted derivatives, the following compounds were prepared:

5-acetyl-N-(2,6-diethylphenyl)-1-methyl-1H-pyrazole-3-carboxamide [(IVe) R2"=Me, R"=2,6-diethylphenyl, R'"=H]

$^1$H NMR (400 MHz, DMSO-d$_6$) δ ppm 9.72 (s, 1 H), 7.59 (s, 1 H), 7.17-7.28 (m, 1 H), 7.06-7.17 (m, 2 H), 4.15 (s, 3 H), 2.56 (s, 3 H), 2.51-2.55 (m, 4 H), 1.09 (t, J=7.57 Hz, 6 H)

HRMS (ESI) calcd for C$_{17}$H$_{22}$N$_3$O$_2$ [M+H]$^+$ 300.1707. found 300.1709.

5-acetyl-N-(2,6-diethylphenyl)-1H-pyrazole-3-carboxamide [(IVd) R2'=H, R"=2,6-diethylphenyl, R'"=H]

$^1$H NMR (400 MHz, DMSO-d$_6$) δ ppm 14.32 (br. s., 1 H), 9.58-10.07 (m, 1 H), 7.42-7.56 (m, 1 H), 7.20-7.29 (m, 1 H), 7.09-7.19 (m, 2 H), 2.51-2.57 (m, 7 H), 0.94-1.18 (m, 6 H)

HRMS (ESI) calcd for C$_{16}$H$_{20}$N$_3$O$_2$ [M+H]$^+$ 286.1550. found 286.1551.

Preparation F

Ethyl 5-[(2E)-3-(dimethylamino)prop-2-enoyl]-1-(3-methoxybenzyl)-1H-pyrazole-3-carboxylate [(VI) R2=3-methoxybenzyl, R3=COOEt]

Step 5

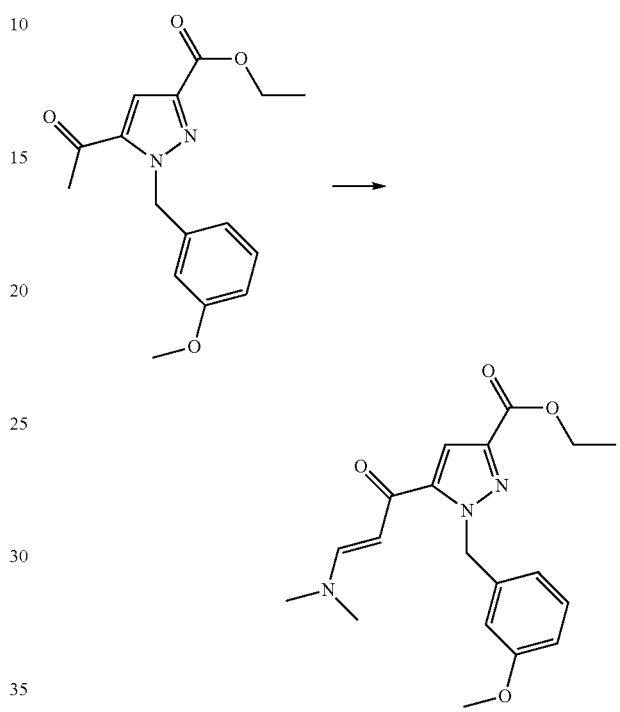

To a solution of ethyl 5-acetyl-1-(3-methoxy-benzyl)-1H-pyrazole-3-carboxylate (300 mg, 1 mmol) in 2 mL toluene, 240 mg (2 mmol) of N,N-dimethylformamide dimethyl acetal were added. The mixture was stirred for 18 h at 140° C. The volatiles were removed under vacuum to afford the title compound in quantitative yield.

LC/MS (254 nm) HPLC method 2: Rt 5.00 min $^1$H NMR (500 MHz, DMSO-d$_6$) δ ppm 7.72 (d, J=12.4 Hz, 1 H), 7.48 (d, J=10.4 Hz, 1 H), 7.15-7.25 (m, 1 H), 6.77-6.85 (m, 1 H), 6.69 (d, J=1.9 Hz, 1 H), 6.66 (d, J=7.7 Hz, 1 H), 5.80-5.87 (m, 2 H), 5.78 (d, J=12.1 Hz, 1 H), 4.28 (q, J=7.0 Hz, 2 H), 3.69 (s, 3 H), 3.14 (s, 3 H), 2.92 (s, 3 H), 1.29 (t, J=7.1 Hz, 3 H)

HRMS (ESI) calcd for C$_{19}$H$_{24}$N$_3$O$_4$ [M+H]$^+$ 358.1762. found 358.1772.

According to the same method, the other isomer was prepared:

ethyl 5-[(2E)-3-(dimethylamino)prop-2-enoyl]-1-(3-methoxybenzyl)-1H-pyrazole-5-carboxylate [(VI) R2=3-methoxybenzyl, R3=COOEt]

LC/MS (254 nm) HPLC method 2: Rt 5.11 min $^1$H NMR (400 MHz, DMSO-d$_6$) δ ppm 7.74 (d, J=12.4 Hz, 1 H), 7.16-7.29 (m, 2 H), 6.85 (dd, J=8.2, 2.5 Hz, 1 H), 6.70 (s, 1 H), 6.64 (d, J=7.4 Hz, 1 H), 5.83 (d, J=12.1 Hz, 1 H), 5.73 (s, 2 H), 4.27 (q, J=7.0 Hz, 2 H), 3.71 (s, 3 H), 3.07-3.18 (m, 3 H), 2.81-2.89 (m, 3 H), 1.20-1.33 (m, 3 H)

HRMS (ESI) calcd for C$_{19}$H$_{24}$N$_3$O$_4$ [M+H]$^+$ 358.1762. found 358.1773.

Preparation G

N-(2,6-diethylphenyl)-5-[(2E)-3-(dimethylamino)prop-2-enoyl]-1-methyl-1H-pyrazole-3-carboxamide [(VI) R2=Me, R3=CONHR", R"=2,6-diethylphenyl]

Step 5

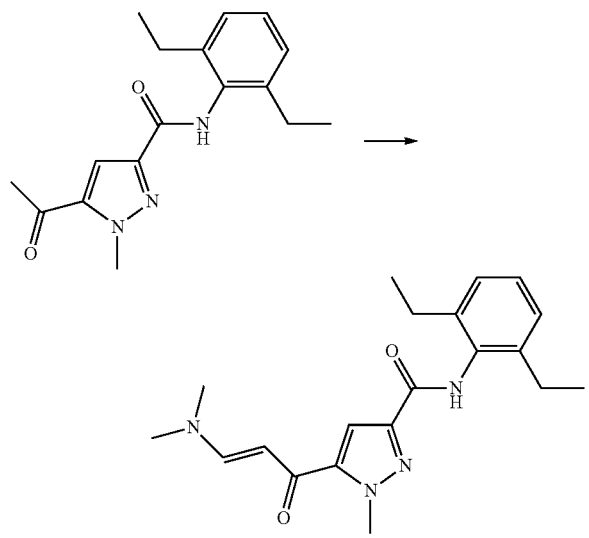

To a solution of 5-acetyl-N-(2,6-diethylphenyl)-1-methyl-1H-pyrazole-3-carboxamide (0.013 g, 0.043 mmol) in DMF (1.5 mL), N,N-dimethylformamide di-tertbutyl acetal (0.0.63 mL, 0.650 mmol) was added. The mixture was stirred at 80° C. for 2 h. The reaction was diluted with water, extracted with AcOEt (2×20 mL). The organic fractions were combined, dried over $Na_2SO_4$, filtered, and concentrated in vacuo and the residue used without any further purification. (0.017 g, 78% yield).

$^1$H NMR (400 MHz, DMSO-$d_6$) δ ppm 9.58 (s, 1 H), 7.71 (d, J=12.33 Hz, 1 H), 7.36 (s, 1 H), 7.21 (t, J=7.60 Hz, 1 H), 7.12 (d, J=7.60 Hz, 2 H), 5.75 (d, J=12.33 Hz, 1 H), 4.18 (s, 3 H), 3.16 (s, 3 H), 2.92 (s, 3 H), 2.52 (q, J=7.57 Hz, 4 H), 1.09 (t, J=7.57 Hz, 6 H)

HRMS (ESI) calcd for $C_{20}H_{27}N_4O_2$ [M+H]$^+$ 355.2129. found 355.2133.

According to this same methodology, but employing suitable substituted derivatives, the following compounds were prepared:

N-(2,6-diethylphenyl)-3-[(2E)-3-(dimethylamino)prop-2-enoyl]-1-methyl-1H-pyrazole-5-carboxamide [(VI) R2=Me, R3=CONHR", R"=2,6-diethylphenyl]

$^1$H NMR (400 MHz, DMSO-$d_6$) δ ppm 9.81 (s, 1 H), 7.75 (d, J=12.45 Hz, 1 H), 7.43 (s, 1 H), 7.19-7.30 (m, 1 H), 7.07-7.18 (m, 2 H), 5.86 (d, J=12.45 Hz, 1 H), 4.11 (s, 3 H), 3.15 (br. s., 3 H), 2.89 (br. s., 3 H), 2.54 (q, J=7.57 Hz, 4 H), 1.12 (t, J=7.57 Hz, 6 H)

HRMS (ESI) calcd for $C_{20}H_{27}N_4O_2$ [M+H]$^+$ 355.2129. found 355.2134.

N-(2,6-diethylphenyl)-5-[(2E)-3-(dimethylamino)prop-2-enoyl]-1-(4-methoxybenzyl)-1H-pyrazole-3-carboxamide [(VI) R2=4-methoxybenzyl, R3=CONHR", R"=2,6-diethylphenyl]

$^1$H NMR (400 MHz, DMSO-$d_6$) δ ppm 9.59 (s, 1 H), 7.73 (d, J=12.25 Hz, 1 H), 7.43 (s, 1 H), 7.17-7.27 (m, 3 H), 7.08-7.17 (m, 2 H), 6.82-6.92 (m, 2 H), 5.80 (s, 2 H), 5.75 (d, J=12.25 Hz, 2 H), 3.71 (s, 3 H),) 3.15 (s, 3 H), 2.91 (s, 3 H), 2.53 (q, J=7.57 Hz, 4 H), 1.09 (t, J=7.57 Hz, 6 H)

HRMS (ESI) calcd for $C_{27}H_{33}N_4O_3$ [M+H]$^+$ 461.2547. found 461.2558.

N-(2,6-diethylphenyl)-3-[(2E)-3-(dimethylamino)prop-2-enoyl]-1-(4-methoxybenzyl)-1H-pyrazole-5-carboxamide [(VI) R2=4-methoxybenzyl, R3=CONHR", R"=2,6-diethylphenyl]

$^1$H NMR (400 MHz, DMSO-$d_6$) δ ppm 9.82 (s, 1 H), 7.77 (d, J=12.08 Hz, 1 H), 7.42 (s, 1 H), 7.20-7.25 (m, 1 H), 7.09-7.14 (m, 4 H), 6.84-6.89 (m, 2 H), 5.87 (d, J=12.08 Hz, 1 H), 5.71 (s, 2 H), 3.71 (s, 3 H), 3.15 (br. s., 3 H), 2.89 (br. s., 3 H), 2.43 (q, J=7.57 Hz, 4 H), 1.04 (t, J=7.57 Hz, 6 H)

HRMS (ESI) calcd for $C_{27}H_{33}N_4O_3$ [M+H]$^+$ 461.2547. found 461.2540.

ethyl 5-[(2E)-3-(dimethylamino)prop-2-enoyl]-1H-pyrazole-3-carboxylate [(VI) R2=H, R3=COOEt]

HRMS (ESI) calcd for $C_{11}H_{16}N_3O_3$ [M+H]$^+$ 238.2605. found 238.2609.

Example 1

5-{2-[(4-bromo-2-methoxyphenyl)amino]pyrimidin-4-yl}-N-(2,6-diethylphenyl)-1-methyl-1H-pyrazole-3-carboxamide [(Ia) R1=4-bromo-2-methoxyphenyl, X=—NH—, R2=Me, R3=CONHR", R"=2,6-diethylphenyl, R4=H] cpd 4

Step 6

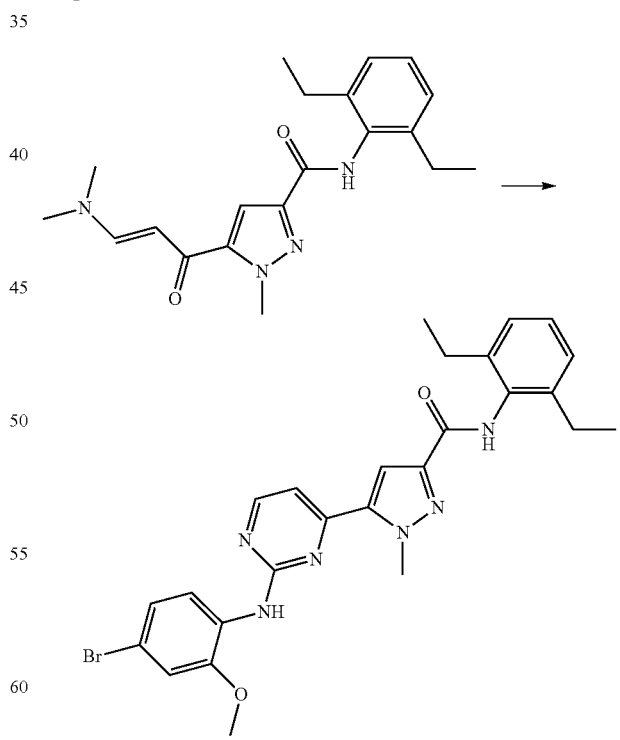

To a solution of N-(2,6-diethylphenyl)-5-[(2E)-3-(dimethylamino)prop-2-enoyl]-1-methyl-1H-pyrazole-3-carboxamide (0.175 g, 0.498 mmol) in DMF (8 mL), N-(4-Bromo-2-methoxy-phenyl)-guanidine (0.182 g, 0.756 mmol)

was added. The mixture was stirred at 120° C. for 5 h. The resulting mixture was cooled at r.t. and concentrated to dryness. The crude solid was purified by flash chromatography on silica gel (eluant: AcOEt/hexane 4/6) to afford 0.235 g (87% yield) of the title compound as a red solid.

$^1$H NMR (400 MHz, DMSO-d$_6$) δ ppm 9.64 (s, 1 H), 8.55 (d, J=5.20 Hz, 1 H), 8.51 (s, 1 H), 7.92 (d, J=8.54 Hz, 1 H), 7.46 (s, 1 H), 7.34 (d, J=5.20 Hz, 1 H), 7.25 (d, J=2.20 Hz, 1 H), 7.19-7.24 (m, 1 H), 7.17 (dd, J=8.54, 2.20 Hz, 1 H), 7.10-7.15 (m, 2 H), 4.24 (s, 3 H), 3.87 (s, 3 H), 2.55 (q, J=7.57 Hz, 4 H), 1.10 (t, J=7.57 Hz, 6 H)

HRMS (ESI) calcd for C$_{26}$H$_{28}$BrN$_6$O$_2$[M+H]$^+$ 535.1452. found 535.1459.

According to this same methodology, but employing suitable substituted derivatives, the following compounds were prepared:

ethyl 5-{2-[(4-bromo-2-methoxyphenyl)amino]pyrimidin-4-yl}-1H-pyrazole-3-carboxylate [(I) R1=4-bromo-2-methoxyphenyl, X=—NH—, R2=H, R3=COOEt, R4=H]

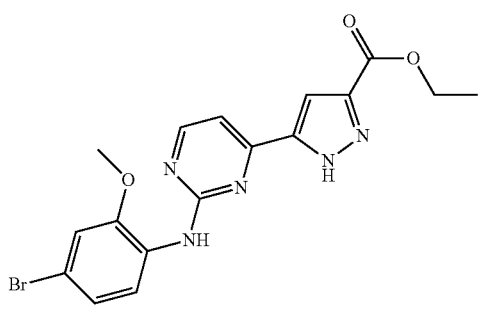 [SMILES: CCOC(=O)c1cc(-c2ccnc(Nc3ccc(Br)cc3OC)n2)[nH]n1]

$^1$H NMR (400 MHz, DMSO-d$_6$) δ ppm 14.28-14.51 (m, 1 H), 8.49-8.64 (m, 1 H), 8.19-8.33 (m, 1 H), 8.04-8.18 (m, 1 H), 7.36-7.54 (m, 2 H), 7.24 (s, 1 H), 7.12-7.22 (m, 1 H), 4.23-4.45 (m, 2 H), 3.90 (s, 3H), 1.25-1.44 (m, 3 H)

HRMS (ESI) calcd for C$_{17}$H$_{17}$BrN$_5$O$_3$[M+H]$^+$ 418.0510. found 418.0520.

5-{2-[(4-bromo-2-methoxyphenyl)amino]pyrimidin-4-yl}-N-(2,6-diethylphenyl)-1-(4-methoxybenzyl)-1H-pyrazole-3-carboxamide [(Ia) R1=4-bromo-2-methoxyphenyl, X=—NH—, R2=4-methoxybenzyl, R3=CONHR", R"=2,6-diethylphenyl, R4=H] cpd 6

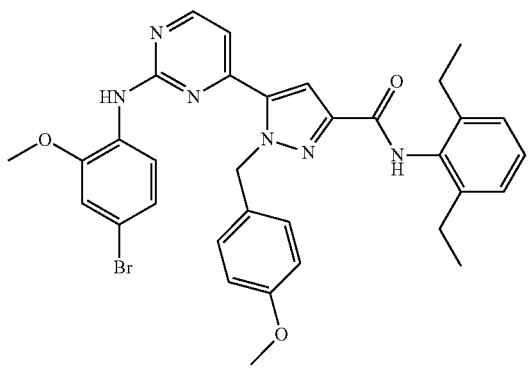 [SMILES: CCc1cccc(CC)c1NC(=O)c1cc(-c2ccnc(Nc3ccc(Br)cc3OC)n2)n(Cc2ccc(OC)cc2)n1]

$^1$H NMR (400 MHz, DMSO-d$_6$) δ ppm 9.67 (s, 1 H), 8.56 (s, 1 H), 8.50 (d, J=5.20 Hz, 1 H), 7.76 (d, J=8.54 Hz, 1 H), 7.54 (s, 1 H), 7.29 (d, J=5.20 Hz, 1 H), 7.22 (d, J=2.20 Hz, 1 H), 7.18-7.25 (m, 1 H), 7.11-7.16 (m, 2 H), 7.06 (dd, J=8.54, 2.20 Hz, 1 H), 6.95-7.03 (m, 2 H), 6.79-6.75 (m, 2 H), 5.92 (s, 2 H), 3.86 (s, 3 H), 3.69 (s, 3 H), 2.54 (q, J=7.51 Hz, 4 H), 1.10 (t, J=7.51 Hz, 6 H)

HRMS (ESI) calcd for C$_{33}$H$_{34}$BrN$_6$O$_3$[M+H]$^+$ 641.1871. found 641.1857.

N-(2,6-diethylphenyl)-5-{2-[(2-methoxyphenyl)amino]pyrimidin-4-yl}-1-methyl-1H-pyrazole-3-carboxamide [(Ia) R1=2-methoxyphenyl, X=—NH—, R2=Me, R3=CONHR", R"=2,6-diethylphenyl, R4=H] cpd 7

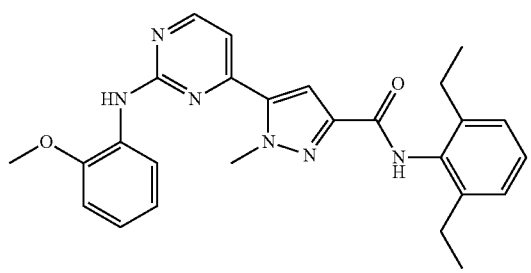 [SMILES: CCc1cccc(CC)c1NC(=O)c1cc(-c2ccnc(Nc3ccccc3OC)n2)n(C)n1]

$^1$H NMR (400 MHz, DMSO-d$_6$) δ ppm 9.64 (s, 1 H), 8.53 (d, J=5.20 Hz, 1 H), 8.46 (s, 1 H), 7.92 (dd, J=7.81, 1.46 Hz, 1 H), 7.45 (s, 1 H), 7.30 (d, J=5.20 Hz, 1 H), 7.19-7.24 (m, 1 H), 7.04-7.15 (m, 4 H), 6.93-7.02 (m, 1 H), 4.22 (s, 3 H), 3.84 (s, 3 H), 2.53 (q, J=7.57 Hz, 4 H), 1.10 (t, J=7.57 Hz, 6 H)

HRMS (ESI) calcd for C$_{26}$H$_{29}$N$_6$O$_2$ [M+H]$^+$ 457.2347. found 457.2358.

N-(2,6-diethylphenyl)-1-(4-methoxybenzyl)-5-{2-[(2-methoxyphenyl)amino]pyrimidin-4-yl}-1H-pyrazole-3-carboxamide [(Ia) R1=2-methoxyphenyl, X=—NH—, R2=4-methoxybenzyl, R3=CONHR", R"=2,6-diethylphenyl, R4=H] cpd 10

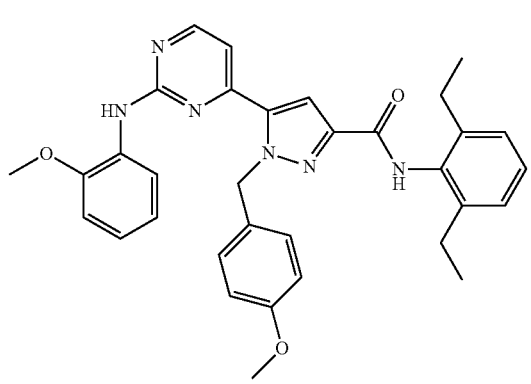 [SMILES: CCc1cccc(CC)c1NC(=O)c1cc(-c2ccnc(Nc3ccccc3OC)n2)n(Cc2ccc(OC)cc2)n1]

$^1$H NMR (400 MHz, DMSO-d$_6$) δ ppm 9.67 (s, 1 H), 8.50 (s, 1 H), 8.48 (d, J=5.13 Hz, 1 H), 7.81 (d, J=8.42 Hz, 1 H), 7.53 (s, 1 H), 7.25 (d, J=5.13 Hz, 1 H), 7.18-7.24 (m, 1 H), 7.11-7.16 (m, 2 H), 7.04-7.11 (m, 2 H), 6.95-7.01 (m, 2 H), 6.87-6.94 (m, 1 H), 6.77-6.83 (m, 2 H), 5.92 (s, 2 H), 3.84 (s, 3 H), 3.68 (s, 3 H), 2.55 (q, J=7.57 Hz, 4 H), 1.11 (t, J=7.57 Hz, 6 H)

HRMS (ESI) calcd for $C_{33}H_{35}N_6O_3$ [M+H]$^+$ 563.2765. found 563.2752.

3-{2-[(4-bromo-2-methoxyphenyl)amino]pyrimidin-4-yl}-N-(2,6-diethylphenyl)-1-(4-methoxybenzyl)-1H-pyrazole-5-carboxamide [(Ib) R1=4-bromo-2-methoxyphenyl, R2=4-methoxybenzyl, X=—NH—, R3=CONHR", R"=2,6-diethylphenyl, R4=H] cpd 5

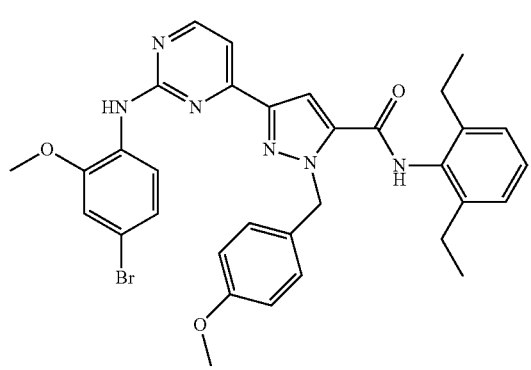 [SMILES: CCc1cccc(CC)c1NC(=O)c1cc(-c2ccnc(Nc3ccc(Br)cc3OC)n2)nn1Cc1ccc(OC)cc1]

$^1$H NMR (400 MHz, DMSO-d$_6$) δ ppm 9.98 (s, 1 H), 8.55 (d, J=5.13 Hz, 1 H), 8.28 (d, J=8.67 Hz, 1 H), 8.12 (s, 1 H), 7.68 (s, 1 H), 7.41 (d, J=5.13 Hz, 1 H), 7.22-7.28 (m, 2 H), 7.10-7.21 (m, 5 H), 6.84-6.92 (m, 2 H), 5.75 (s, 2 H), 3.90 (s, 3 H), 3.72 (s, 3 H), 2.47 (q, J=7.57 Hz, 4 H), 1.08 (t, J=7.57 Hz, 6 H)

HRMS (ESI) calcd for $C_{33}H_{34}BrN_6O_3$[M+H]$^+$ 641.1871. found 641.1896.

N-(2,6-diethylphenyl)-1-(4-methoxybenzyl)-3-{2-[(2-methoxyphenyl)amino]pyrimidin-4-yl}-1H-pyrazole-5-carboxamide [(Ib) R1=2-methoxyphenyl, X=—NH—, R2=4-methoxybenzyl, R3=CONHR", R"=2,6-diethylphenyl, R4=H] cpd 12

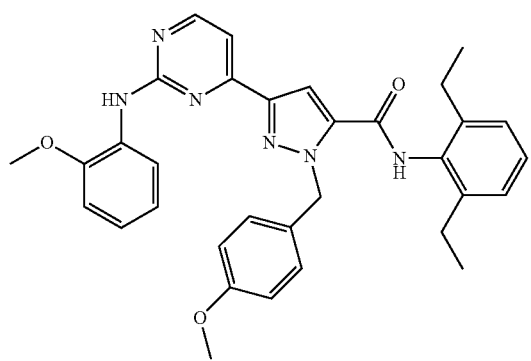 [SMILES: CCc1cccc(CC)c1NC(=O)c1cc(-c2ccnc(Nc3ccccc3OC)n2)nn1Cc1ccc(OC)cc1]

$^1$H NMR (400 MHz, DMSO-d$_6$) δ ppm 10.01 (s, 1 H), 8.54 (d, J=5.13 Hz, 1 H), 8.35 (dd, J=7.93, 1.46 Hz, 1 H), 8.05 (s, 1 H), 7.71 (s, 1 H), 7.38 (d, J=5.13 Hz, 1 H), 7.21-7.27 (m, 1 H), 7.13-7.21 (m, 4 H), 6.93-7.09 (m, 3 H), 6.83-6.91 (m, 2 H), 5.76 (s, 2 H), 3.88 (s, 3 H), 3.72 (s, 3 H), 2.47 (q, J=7.51 Hz, 4 H), 1.08 (t, J=7.51 Hz, 6 H)

HRMS (ESI) calcd for $C_{33}H_{35}N_6O_3$ [M+H]$^+$ 563.2765. found 563.2770.

3-{2-[(4-bromo-2-methoxyphenyl)amino]pyrimidin-4-yl}-N-(2,6-diethylphenyl)-1-methyl-1H-pyrazole-5-carboxamide [(Ib) R1=4-bromo-2-methoxyphenyl, X=—NH—, R2=Me, R3=CONHR", R"=2,6-diethylphenyl, R4=H] cpd 1

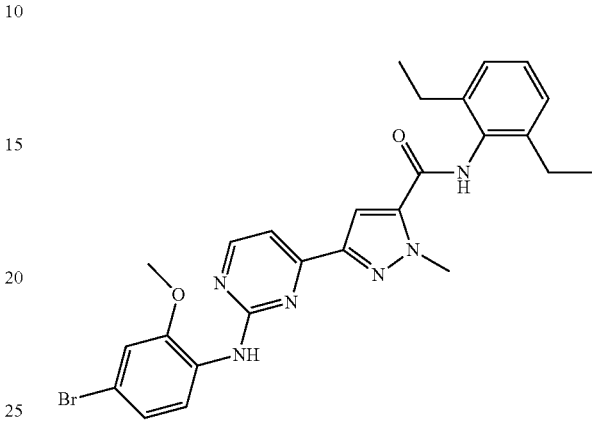

$^1$H NMR (400 MHz, DMSO-d$_6$) δ ppm 9.98 (s, 1 H), 8.54 (d, J=5.13 Hz, 1 H), 8.28 (d, J=8.67 Hz, 1 H), 8.10 (s, 1 H), 7.71 (s, 1 H), 7.38 (d, J=5.13 Hz, 1 H), 7.22-7.29 (m, 2 H), 7.11-7.21 (m, 3 H), 4.17 (s, 3 H), 3.91 (s, 3 H), 2.58 (q, J=7.57 Hz, 4 H), 1.15 (t, J=7.57 Hz, 6 H)

HRMS (ESI) calcd for $C_{26}H_{28}BrN_6O_2$[M+H]$^+$ 535.1452. found 535.1453.

N-(2,6-diethylphenyl)-3-(2-{[2-methoxy-4-(4-methylpiperazin-1-yl)phenyl]amino}pyrimidin-4-yl)-1-methyl-1H-pyrazole-5-carboxamide [(Ib) R1=2-methoxy(4-methylpiperazin-yl)phenyl, X=—NH—, R2=Me, R3=CONHR", R"=2,6-diethylphenyl, R4=H] cpd 2

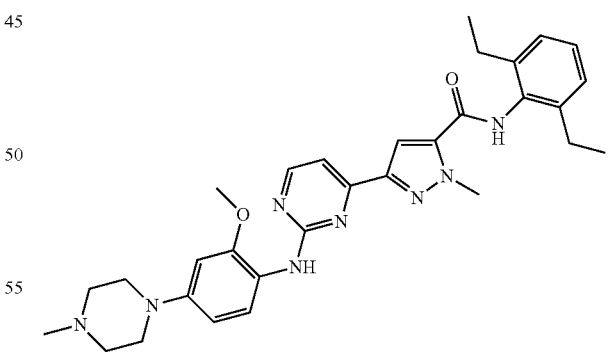

$^1$H NMR (400 MHz, DMSO-d$_6$) δ ppm 10.00 (s, 1 H), 8.44 (d, J=5.13 Hz, 1 H), 7.93 (d, J=8.67 Hz, 1 H), 7.91 (s, 1H), 7.66 (s, 1 H), 7.23-7.30 (m, 2 H), 7.15-7.20 (m, 2 H), 6.66 (d, J=2.56 Hz, 1 H), 6.51 (dd, J=8.67, 2.56 Hz, 1H), 4.16 (s, 3 H), 3.84 (s, 3 H), 3.08-3.16 (m, 4 H), 2.58 (q, J=7.57 Hz, 4 H), 2.45-2.52 (m, 4 H), 2.24 (s, 3 H), 1.15 (t, J=7.57 Hz, 6 H)

HRMS (ESI) calcd for $C_{31}H_{39}N_8O_2$ [M+H]$^+$ 555.3190. found 555.3185.

Example 2

N-(2,6-diethylphenyl)-5-(2-{[2-methoxy-4-(4-methylpiperazin-1-yl)phenyl]amino}pyrimidin-4-yl)-1-methyl-1H-pyrazole-3-carboxamide [(Ia) R1=2-methoxy(4-methylpiperazin-yl)phenyl, X=—NH—, R2=Me, R3=CONHR", R"=2,6-diethylphenyl, R4=H] cpd 3 conv. 1

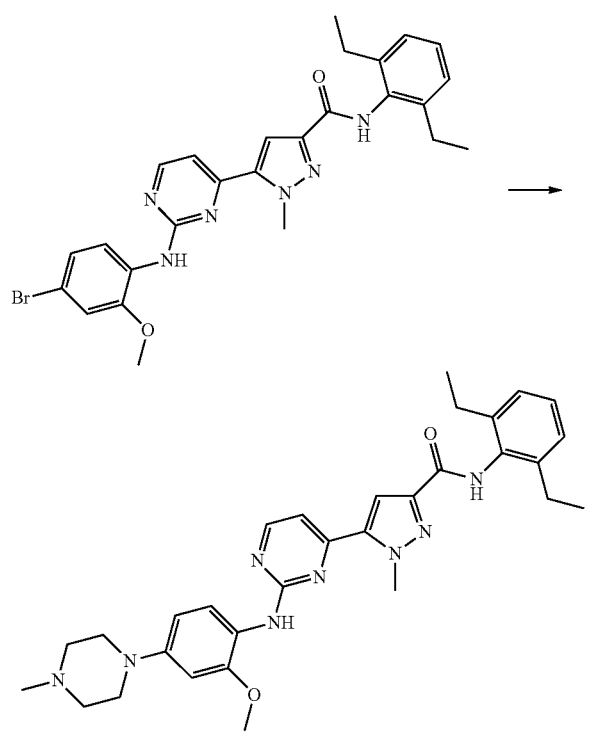

Pd$_2$(dba)$_3$ (0.002 g, 0.002 mmol), 2-dicyclohexylphosphino-2'-(N,N-dimethylamino)-biphenyl (0.002 g, 0.005 mmol), 5-{2-[(4-bromo-2-methoxyphenyl)amino]pyrimidin-4-yl}-N-(2,6-diethylphenyl)-1-methyl-1H-pyrazole-3-carboxamide (0.115 g, 0.215 mmol) in THF (5 mL) were charged in a round-bottomed flask flushed with argon. The flask was evacuated and backfilled with argon. LiN(TMS)$_2$ solution (1M in THF, 1.29 mL) and N-methylpiperazine (0.036 mL, 0.322 mmol) were added and the reaction mixture was heated at 85° C. for 2 h. The reaction mixture was then allowed to cool to r.t. and concentrated. The crude solid was purified by flash chromatography on silica gel (eluant: DCM/MeOH 95/5) to afford 0.107 g (90% yield) of the title compound as a yellow solid.

$^1$H NMR (400 MHz, DMSO-d$_6$) δ ppm 9.60 (s, 1 H), 8.44 (d, J=5.13 Hz, 1 H), 8.34 (s, 1 H), 7.51 (d, J=8.67 Hz, 1 H), 7.40 (s, 1 H), 7.19-7.25 (m, 1 H), 7.18 (d, J=5.13 Hz, 1 H), 7.09-7.15 (m, 2 H), 6.64 (d, J=2.45 Hz, 1 H), 6.51 (dd, J=8.67, 2.45 Hz, 1 H), 4.17 (s, 3 H), 3.79 (s, 3 H), 3.09-3.19 (m, 4 H), 2.53 (q, J=7.57 Hz, 4 H), 2.43-2.48 (m, 4 H), 2.24 (s, 3 H), 1.09 (t, J=7.57 Hz, 6 H)

HRMS (ESI) calcd for C$_{31}$H$_{39}$N$_8$O$_2$ [M+H]$^+$ 555.3191. found 555.3180.

According to this same methodology, but employing suitable substituted derivatives, the following compounds were prepared:

N-(2,6-diethylphenyl)-5-[2-({4-[4-(2-hydroxyethyl)piperazin-1-yl]-2-methoxyphenyl}amino)pyrimidin-4-yl]-1-methyl-1H-pyrazole-3-carboxamide [(Ia) R1=4-(2-hydroxyethyl)piperazin-yl)-2-methoxyphenyl, X=—NH—, R2=Me, R3=CONHR", R"=2,6-diethylphenyl, R4=H] cpd 8

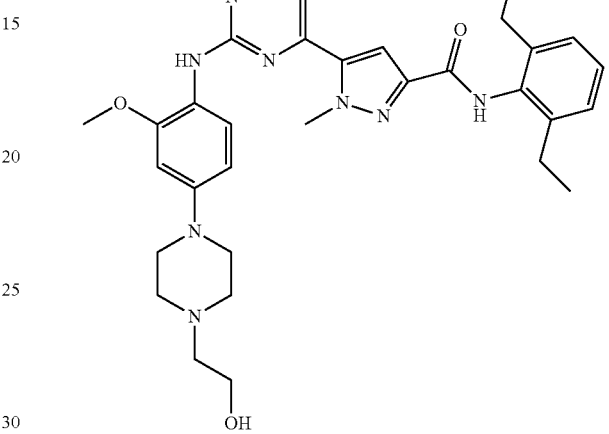

$^1$H NMR (400 MHz, DMSO-d$_6$) δ ppm 9.60 (s, 1 H), 8.44 (d, J=5.15 Hz, 1 H), 8.34 (s, 1 H), 7.47-7.53 (m, 1 H), 7.40 (s, 1 H), 7.19-7.24 (m, 1 H), 7.18 (d, J=5.15 Hz, 1 H), 7.09-7.15 (m, 2 H), 6.63 (d, J=2.56 Hz, 1 H), 6.51 (dd, J=8.79, 2.56 Hz, 1 H), 4.35-4.45 (m, 1 H), 4.17 (s, 3 H), 3.79 (s, 3 H), 3.55 (q, J=6.02 Hz, 2 H), 3.08-3.19 (m, 4 H), 2.55-2.63 (m, 4 H), 2.53 (q, J=7.57 Hz, 4 H), 2.40-2.48 (m, 2 H), 1.09 (t, J=7.57 Hz, 6 H)

HRMS (ESI) calcd for C$_{32}$H$_{41}$N$_8$O$_3$ [M+H]$^+$ 585.3296. found 585.3302.

N-(2,6-diethylphenyl)-1-(4-methoxybenzyl)-5-(2-{[2-methoxy-4-(4-methylpiperazin-1-yl)phenyl]amino}pyrimidin-4-yl)-1H-pyrazole-3-carboxamide [(Ia) R1=2-methoxy(4-methylpiperazin-yl)phenyl, X=—NH—, R2=4-methoxybenzyl, R3=CONHR", R"=2,6-diethylphenyl, R4=H] cpd 9

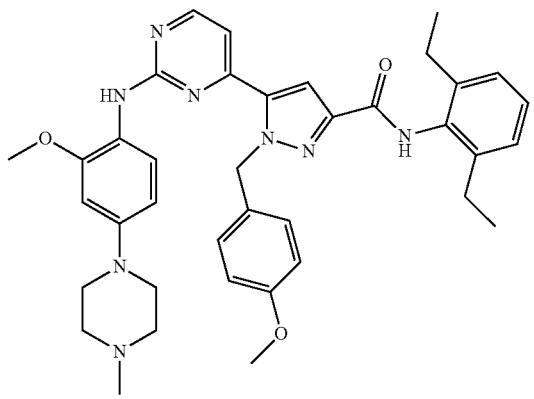 [SMILES: CCc1cccc(CC)c1NC(=O)c1cc(-c2ccnc(Nc3ccc(N4CCN(C)CC4)cc3OC)n2)n(Cc2ccc(OC)cc2)n1]

¹H NMR (400 MHz, DMSO-d₆) δ ppm 9.62 (s, 1 H), 8.41 (d, J=5.00 Hz, 2 H), 8.40 (s, 1 H), 7.48 (s, 1 H), 7.39 (d, J=8.80 Hz, 1 H), 7.18-7.25 (m, 1 H), 7.14 (d, J=5.00 Hz, 1 H), 7.10-7.14 (m, 2 H), 6.92-7.02 (m, 2 H), 6.74-6.82 (m, 2 H), 6.60 (d, J=2.44 Hz, 1 H), 6.41 (dd, J=8.80, 2.44 Hz, 1 H), 5.87 (s, 2 H), 3.77 (s, 3 H), 3.69 (s, 3 H), 3.03-3.18 (m, 4 H), 2.53 (q, J=7.51 Hz, 4 H), 2.41-2.48 (m, 4 H), 2.23 (s, 3 H), 1.10 (t, J=7.51 Hz, 6 H)

HRMS (ESI) calcd for $C_{38}H_{45}N_8O_3$ [M+H]⁺ 661.3609. found 661.3611.

N-(2,6-diethylphenyl)-3-(2-{[2-methoxy-4-(4-methylpiperazin-1-yl)phenyl]amino}pyrimidin-4-yl)-1-methyl-1H-pyrazole-5-carboxamide [(Ib) R1=2-methoxy(4-methylpiperazin-yl)phenyl, X=—NH—, R2=Me, R3=CONHR", R"=2,6-diethylphenyl, R4=H] cpd 2

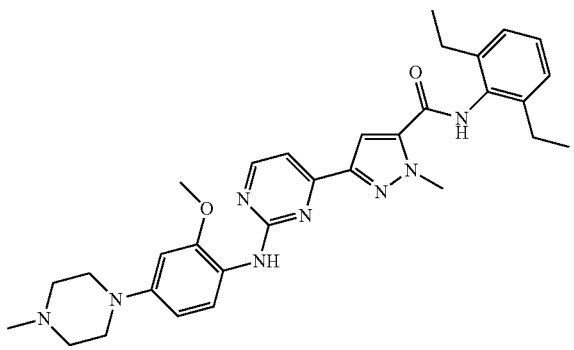 [SMILES: CCc1cccc(CC)c1NC(=O)c1cc(-c2ccnc(Nc3ccc(N4CCN(C)CC4)cc3OC)n2)nn1C]

¹H NMR (400 MHz, DMSO-d₆) δ ppm 10.00 (s, 1 H), 8.44 (d, J=5.13 Hz, 1 H), 7.93 (d, J=8.67 Hz, 1 H), 7.91 (s, 1 H), 7.66 (s, 1 H), 7.23-7.30 (m, 2 H), 7.15-7.20 (m, 2 H), 6.66 (d, J=2.56 Hz, 1 H), 6.51 (dd, J=8.67, 2.56 Hz, 1 H), 4.16 (s, 3 H), 3.84 (s, 3 H), 3.08-3.16 (m, 4 H), 2.58 (q, J=7.57 Hz, 4 H), 2.45-2.52 (m, 4 H), 2.24 (s, 3 H), 1.15 (t, J=7.57 Hz, 6 H)

HRMS (ESI) calcd for $C_{31}H_{39}N_8O_2$ [M+H]⁺ 555.3190. found 555.3185.

N-(2,6-diethylphenyl)-3-[2-({4-[4-(2-hydroxyethyl)piperazin-1-yl]-2-methoxyphenyl}amino)pyrimidin-4-yl]-1-(4-methoxybenzyl)-1H-pyrazole-5-carboxamide [(Ib) R1=4-(2-hydroxyethyl)piperazin-yl)-2-methoxyphenyl, X=—NH—, R2=4-methoxybenzyl, R3=CONHR", R"=2,6-diethylphenyl, R4=H]

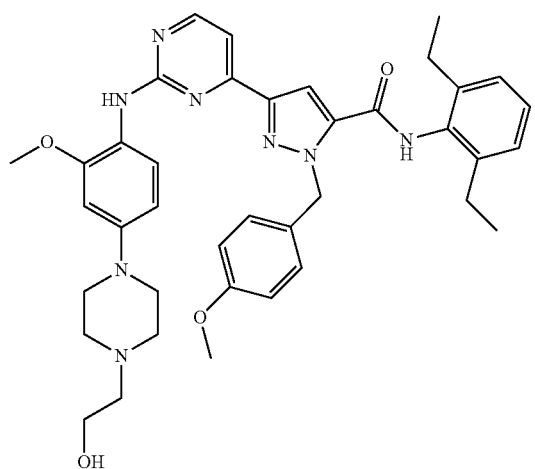 [SMILES: CCc1cccc(CC)c1NC(=O)c1cc(-c2ccnc(Nc3ccc(N4CCN(CCO)CC4)cc3OC)n2)nn1Cc1ccc(OC)cc1]

HRMS (ESI) calcd for $C_{39}H_{46}N_8O_4$ [M+H]⁺ 690.8527. found 690.8539

Example 3

N-(2,6-diethylphenyl)-5-(2-{[2-methoxy-4-(4-methylpiperazin-1-yl)phenyl]amino}pyrimidin-4-yl)-1H-pyrazole-3-carboxamide [(I) R1=2-methoxy(4-methylpiperazin-yl)phenyl, X=—NH—, R2 and R4=H, R3=CONHR", R"=2,6-diethylphenyl] cpd 11 conv. i

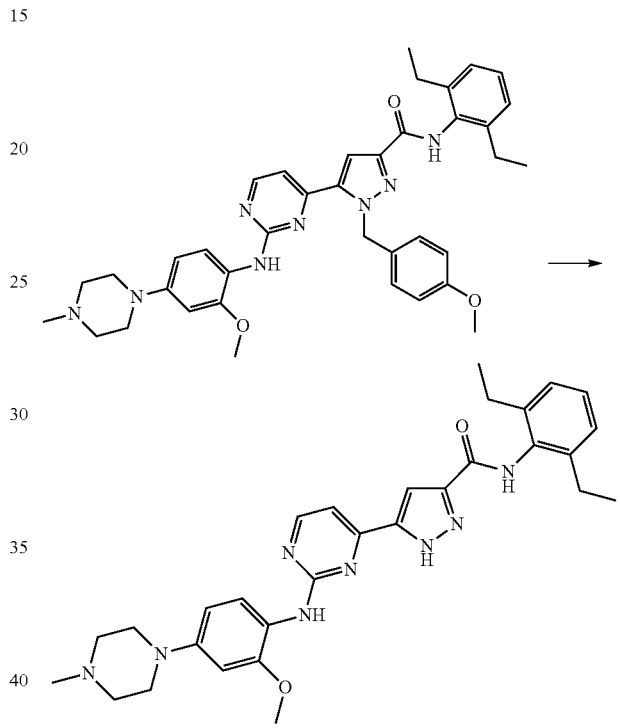

N-(2,6-diethylphenyl)-1-(4-methoxybenzyl)-5-(2-{[2-methoxy-4-(4-methylpiperazin-1-yl)phenyl] amino}pyrimidin-4-yl)-1 H-pyrazole-3-carboxamide (0.054 g, 0.082 mmol) was dissolved in TFA (2 mL). The mixture was stirred at 70° C. for 3 h. The organic solvent was evaporated to dryness and the residue was dissolved in DCM (50 mL) and washed with NaHCO₃. The organic layer was dried over anhydrous Na₂SO₄ and the solvent evaporated to dryness. The crude solid was purified by flash chromatography on silica gel (eluant: DCM/MeOH:95/5) to afford 0.034 g (77% yield) of the title compound.

¹H NMR (400 MHz, DMSO-d₆) δ ppm 14.14 (br. s., 1 H), 9.93 (br. s., 1 H), 8.46 (br. s., 1 H), 7.97 (d, J=8.79 Hz, 1 H), 7.87 (br. s., 1 H), 7.49 (br. s., 1H), 7.29 (d, J=5.00 Hz, 1 H), 7.20-7.28 (m, 1 H), 7.12-7.20 (m, 2 H), 6.66 (d, J=2.56 Hz, 1 H), 6.52 (dd, J=8.79, 2.56 Hz, 1 H), 3.85 (s, 3 H), 3.08-3.16 (m, 4 H), 2.56 (q, J=7.57 Hz, 4 H), 2.42-2.49 (m, 4 H), 2.23 (s, 3 H), 1.12 (t, J=7.57 Hz, 6 H)

HRMS (ESI) calcd for $C_{30}H_{37}N_8O_2$ [M+H]⁺ 541.3034. found 541.3038.

According to this same methodology, but employing suitable substituted derivatives, the following compounds were prepared:

N-(2,6-diethylphenyl)-5-[2-({4-[4-(2-hydroxyethyl)piperazin-1-yl]-2-methoxyphenyl}amino)pyrimidin-4-yl]-1H-pyrazole-3-carboxamide [(I) R1=4-(2-hydroxyethyl)piperazin-yl)-2-methoxyphenyl, X=—NH—, R2 and R4=H, R3=CONHR", R"=2,6-diethylphenyl] cpd 13

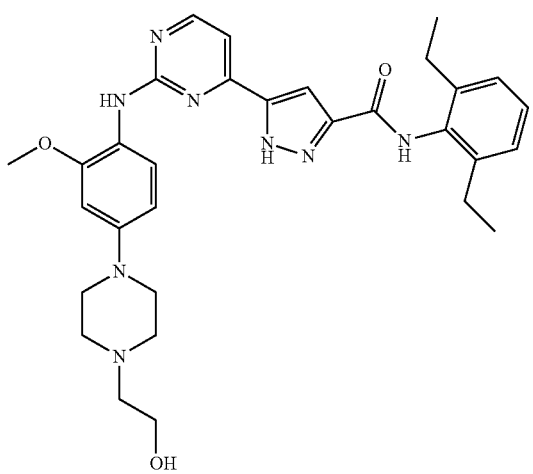 [SMILES: CCc1cccc(CC)c1NC(=O)c1cc(-c2ccnc(Nc3ccc(N4CCN(CCO)CC4)cc3OC)n2)[nH]n1]

¹H NMR (400 MHz, DMSO-d₆) δ ppm 14.14 (s, 1 H), 9.49-10.08 (m, 1 H), 8.39-8.59 (m, 2 H), 7.97 (d, J=8.91 Hz, 1 H), 7.60-7.91 (m, 1 H), 7.29 (d, J=5.13 Hz, 1 H), 7.21-7.28 (m, 1 H), 7.11-7.21 (m, 2 H), 6.66 (d, J=2.44 Hz, 1 H), 6.52 (dd, J=8.73, 2.44 Hz, 1 H), 4.37-4.44 (m, 1 H), 3.85 (s, 3 H), 3.54 (q, J=5.92 Hz, 2 H), 3.06-3.15 (m, 4 H), 2.52-2.61 (m, 8 H), 2.44 (t, J=5.92 Hz, 2 H), 1.12 (t, J=7.57 Hz, 6 H)

HRMS (ESI) calcd for $C_{31}H_{39}N_8O_3$ [M+H]⁺ 571.3140. found 571.3151.

N-(2,6-diethylphenyl)-5-{2-[(2-methoxyphenyl)amino]pyrimidin-4-yl}-1H-pyrazole-3-carboxamide [(I) R1=2-methoxyphenyl, X=—NH—, R2 and R4=H, R3=CONHR", R"=2,6-diethyphenyl] cpd 14

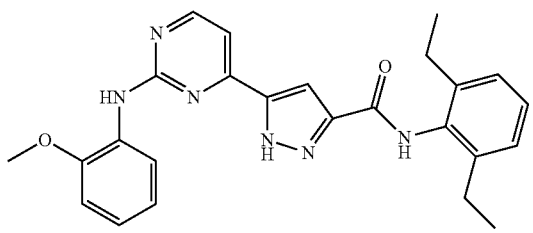 [SMILES: CCc1cccc(CC)c1NC(=O)c1cc(-c2ccnc(Nc3ccccc3OC)n2)[nH]n1]

¹H NMR (400 MHz, DMSO-d₆) δ ppm 14.17-14.23 (m, 1 H), 9.65-9.96 (m, 1 H), 8.51-8.62 (m, 1 H), 8.38 (dd, J=6.90, 1.83 Hz, 1 H), 7.98-8.06 (m, 1 H), 7.73-7.78 (m, 1 H), 7.38-7.43 (m, 1 H), 7.10-7.30 (m, 3 H), 6.95-7.10 (m, 3 H), 4.22 (s, 3 H), 3.89 (s, 3 H), 2.523-2.62 (m, 4 H), 1.07-1.18 (m, 6 H)

HRMS (ESI) calcd for $C_{25}H_{27}N_6O_2$ [M+H]⁺ 443.2190. found 443.2191.

Example 4

3-{2-[(4-bromo-2-methoxyphenyl)amino]pyrimidin-4-yl}-1-methyl-1H-pyrazole-5-carboxylic acid [(Ib) R1=4-bromo-2-methoxyphenyl, X=—NH—, R2=Me, R3=COOH, R4=H]

conv. a

Ethyl 3-{2-[(4-bromo-2-methoxyphenyl)amino]pyrimidin-4-yl}-1-methyl-1H-pyrazole-5-carboxylate (15 mg, 0.034 mmol) was suspended in anhydrous EtOH (2 mL) and treated with a 2 M solution of NaOH (50 μL, 0.1 eq.) at reflux for 1 h. Solvent was evaporated to dryness and the residue dissolved in H₂O. After treatment with AcOH and the resulting precipitate was collected by filtration to give the title compound (6 mg, 50% yield) as a white solid.

¹H NMR (400 MHz, DMSO-d₆) δ ppm 8.51 (d, J=5.13 Hz, 1 H), 8.19 (d, J=8.54 Hz, 1 H), 8.15 (s, 1 H), 7.37 (s, 1 H), 7.35 (d, J=5.13 Hz, 1 H), 7.23 (d, J=2.20 Hz, 1 H), 7.16-7.20 (m, 1 H), 4.18 (s, 3 H), 3.89 (s, 3 H)

HRMS (ESI) calcd for $C_{16}H_{15}BrN_5O_3$[M+H]⁺ 404.0353. found 404.0360.

Example 5

3-{2-[(4-bromo-2-methoxyphenyl)amino]pyrimidin-4-yl}-N-(2,6-diethylphenyl)-1-methyl-1H-pyrazole-5-carboxamide [(Ib) R1=4-bromo-2-methoxyphenyl, X=—NH—, R2=Me, R3=CONHR", R"=2,6-diethylphenyl, R4=H] cpd 1 conv. c

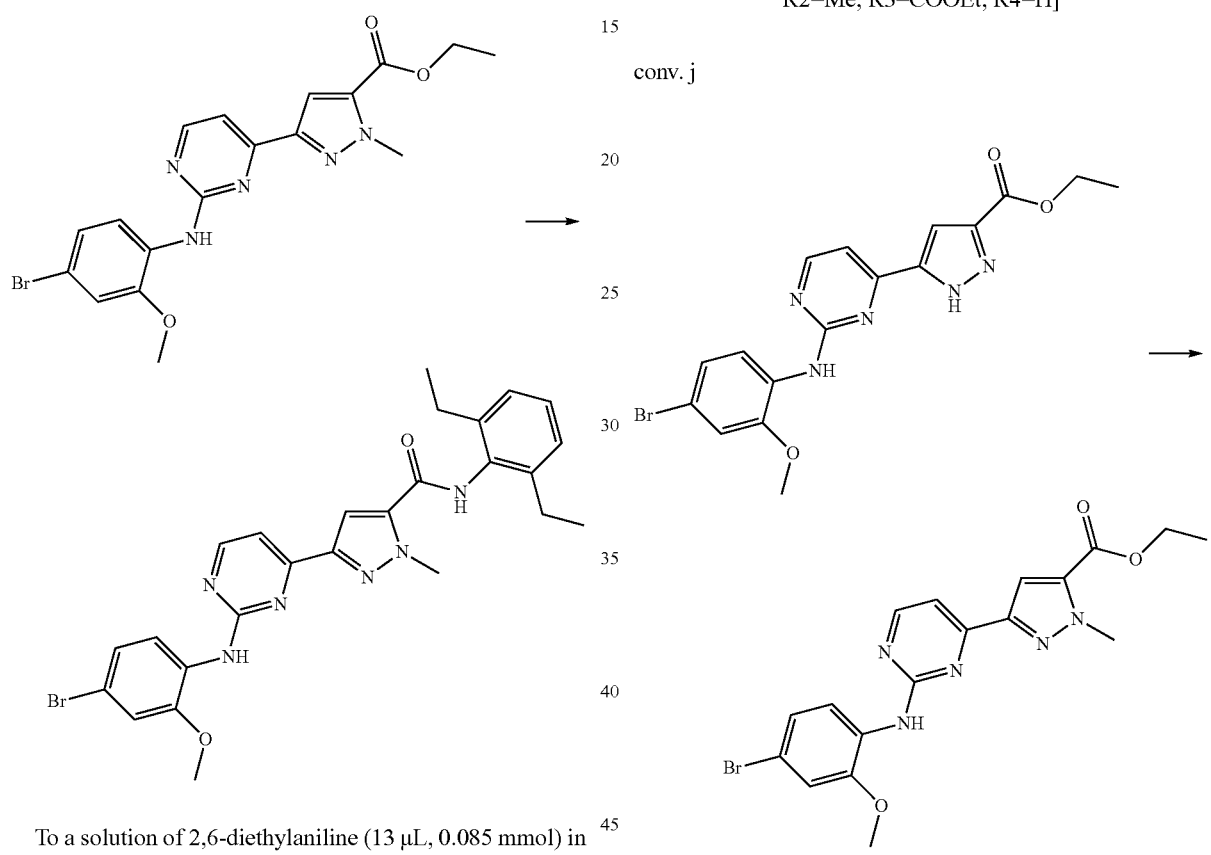

To a solution of 2,6-diethylaniline (13 μL, 0.085 mmol) in anhydrous THF (1 mL) under argon, 1M THF solution of NaN(TMS)$_2$ (70 μL, 0.070 mmol) at 0° C. was added dropwise. The mixture was stirred at 0° C. for 10 min then ethyl 3-{2-[(4-bromo-2-methoxyphenyl)amino]pyrimidin-4-yl}-1-methyl-1H-pyrazole-5-carboxylate (15 mg, 0.034 mmol) in anhydrous THF (1 mL) at 0° C. was added dropwise. Ice bath was removed and the mixture was stirred at r.t. for 1 h. H$_2$O (10 mL) was added and the mixture was extracted with DCM. The organic layer was dried over anhydrous Na$_2$SO$_4$ and the solvent evaporated to dryness. The crude solid was purified by flash chromatography on silica gel (eluant: AcOEt/cyclohexane 2/8) to afford 12 mg (70% yield) of the title compound.

$^1$H NMR (400 MHz, DMSO-d$_6$) δ ppm 9.98 (s, 1 H), 8.54 (d, J=5.13 Hz, 1 H), 8.28 (d, J=8.67 Hz, 1 H), 8.10 (s, 1 H), 7.71 (s, 1 H), 7.38 (d, J=5.13 Hz, 1 H), 7.11-7.29 (m, 2 H), 7.11-7.21 (m, 3 H), 4.17 (s, 3 H), 3.91 (s, 3 H), 2.58 (q, J=7.57 Hz, 4 H), 1.15 (t, J=7.57 Hz, 6 H)

HRMS (ESI) calcd for C$_{26}$H$_{28}$BrN$_6$O$_2$[M+H]$^+$ 535.1452. found 535.1453.

Example 6

Ethyl 3-{2-[(4-bromo-2-methoxyphenyl)amino]pyrimidin-4-yl}-1-methyl-1H-pyrazole-5-carboxylate [(Ib) R1=4-bromo-2-methoxyphenyl, X=—NH—, R2=Me, R3=COOEt, R4=H]

conv. j

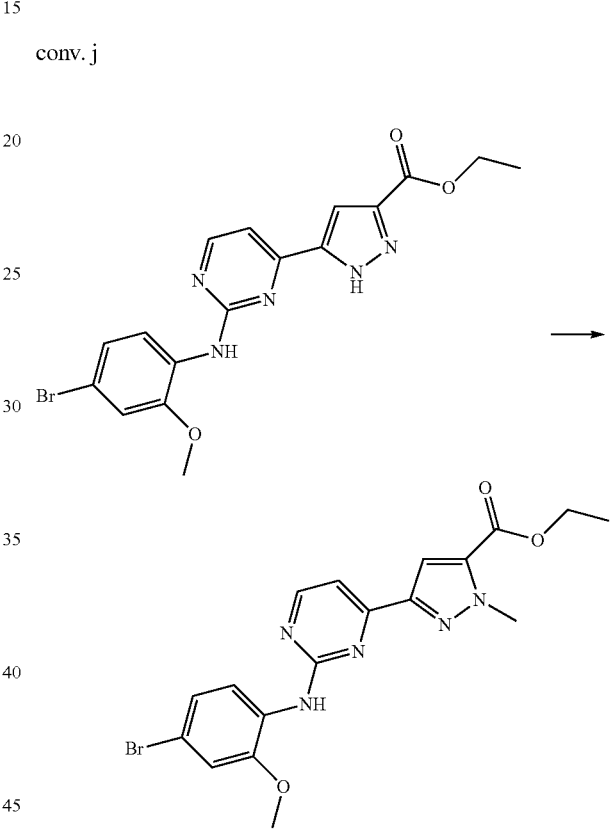

To a solution of ethyl 5-{2-[(4-bromo-2-methoxyphenyl)amino]pyrimidin-4-yl}-1H-pyrazole-3-carboxylate (20 mg, 0.048 mmol) in DMF (2 mL), Cs$_2$CO$_3$ (27 mg, 0.0726 mmol) and methyl iodide (3 μL, 0.048 mmol) were added. The reaction was stirred at r.t. for 1 h, solvent was removed under vacuo. The crude solid was purified by flash chromatography on silica gel (eluant: DCM/EtOH 97/3) providing 18 mg (87% yield) of the title compound as a white solid.

$^1$H NMR (400 MHz, DMSO-d$_6$) δ ppm 8.52 (d, J=5.05 Hz, 1 H), 8.19 (d, J=8.54 Hz, 1 H), 8.17 (s, 1 H), 7.42 (s, 1 H), 7.36 (d, J=5.05 Hz, 1 H), 7.24 (d, J=2.20 Hz, 1 H), 7.17 (dd, J=8.54, 2.20 Hz, 1 H), 4.35 (q, J=7.08 Hz, 2 H), 4.19 (s, 3 H), 3.90 (s, 3 H) 1.35 (t, J=7.08 Hz, 3 H)

HRMS (ESI) calcd for C$_{18}$H$_{19}$BrN$_5$O$_3$[M+H]$^+$ 432.0666. found 432.0667.

Example 7

Ethyl 1-(3-methoxybenzyl)-3-[2-(methylsulfanyl)pyrimidin-4-yl]-1H-pyrazole-5-carboxylate [(Ib) R1=Me, X=—S—, R2=3-methoxybenzyl, R3=COOEt, R4=H]

step 6

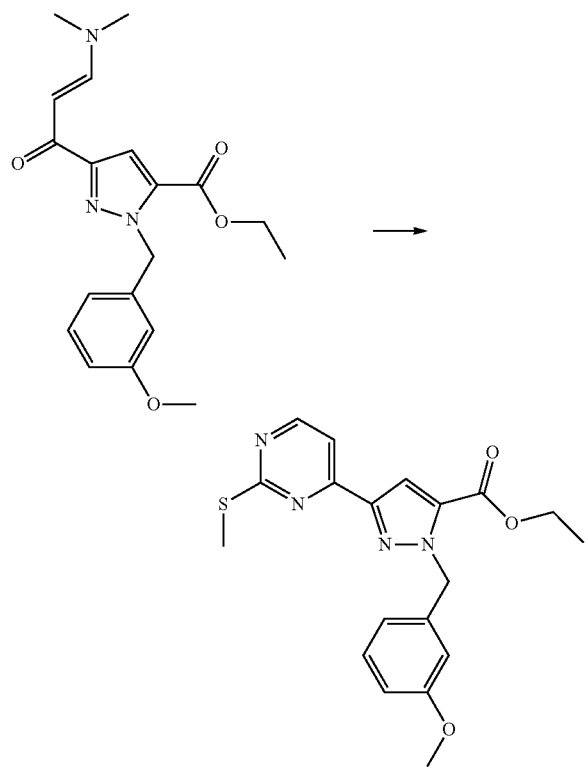

To a solution of 100 mg (0.28 mmol) of ethyl 3-[(2E)-3-(dimethylamino)prop-2-enoyl]-1-(3-methoxybenzyl)-1H-pyrazole-5-carboxylate in 2 mL of EtOH, 50 mg (0.5 mmol) of anhydrous potassium acetate and 120 mg (0.42 mmol) of methylisothiourea sulfate were added. The reaction was stirred at 130° C. for 4 h. The mixture was diluted with AcOEt, washed with $H_2O$, dried over $Na_2SO_4$, filtered and evaporated. The crude was purified through preparative HPLC (15%).

LC/MS (254 nm) HPLC method 2: Rt 6.98 min $^1$H NMR (600 MHz, DMSO-$d_6$) δ ppm 8.67 (d, J=5.1 Hz, 1 H), 7.66 (d, J=5.1 Hz, 1 H), 7.53 (s, 1 H), 7.25 (t, J=8.0 Hz, 1 H), 6.86 (d, J=8.2 Hz, 1 H), 6.75 (d, J=8.1 Hz, 1 H), 6.70 (br. s., 1 H), 5.79 (s, 2 H), 4.29 (t, J=6.9 Hz, 2 H), 3.71 (s, 3 H), 2.57 (s, 3 H), 1.26 (t, J=6.8 Hz, 3 H)

HRMS (ESI) calcd for $C_{19}H_{21}N_4O_3S$ [M+H]$^+$ 385.1329. found 385.1313.

Example 8

Ethyl 1-(3-methoxybenzyl)-3-(2-methylpyrimidin-4-yl)-1H-pyrazole-5-carboxylate [(Ib) R1=Me, X=single bond, R2=3-methoxybenzyl, R3=COOEt, R4=H]

step 6

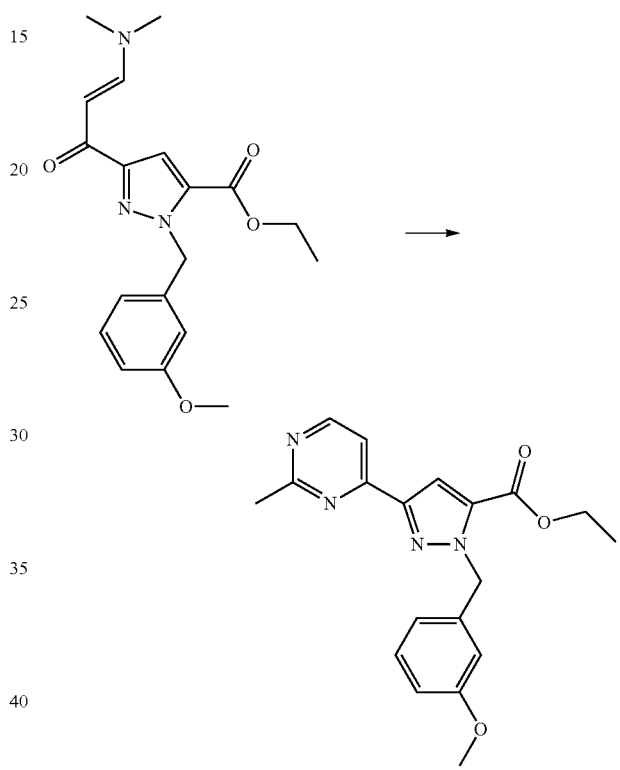

To a solution of 50 mg (0.14 mmol) of ethyl 3-[(2E)-3-(dimethylamino)prop-2-enoyl]-1-(3-methoxybenzyl)-1H-pyrazole-5-carboxylate in 1 mL of EtOH, 40 mg (0.48 mmol) of anhydrous potassium ethoxide and 30 mg (0.28 mmol) of acetamidine hydrochloride were added. The reaction was stirred at 130° C. for 6 h. The mixture was diluted with AcOEt, washed with $H_2O$, dried over $Na_2SO_4$, filtered and evaporated. The crude was purified through preparative HPLC (26%).

LC/MS (254 nm) HPLC method 2: Rt 5.97 min $^1$H NMR (600 MHz, DMSO-$d_6$) δ ppm 8.73 (d, J=5.1 Hz, 1 H), 7.79 (d, J=5.1 Hz, 1 H), 7.53 (s, 1 H), 7.25 (t, J=8.0 Hz, 1 H), 6.86 (dd, J=8.1, 2.4 Hz, 1 H), 6.76 (s, 1 H), 6.72 (d, J=7.7 Hz, 1 H), 5.79 (s, 2 H), 4.31 (q, J=7.1 Hz, 2 H), 3.71 (s, 3 H), 2.66 (s, 3 H), 1.30 (t, J=7.1 Hz, 3 H)

HRMS (ESI) calcd for $C_{19}H_{21}N_4O_3$ [M+H]$^+$ 353.1608. found 353.1614.

Example 9

1-(3-methoxybenzyl)-3-(2-methylpyrimidin-4-yl)-1H-pyrazole-5-carboxamide [(Ib) R1=Me, X=single bond, R2=3-methoxybenzyl, R3=CONH$_2$, R4=H] cpd 24 conv. c

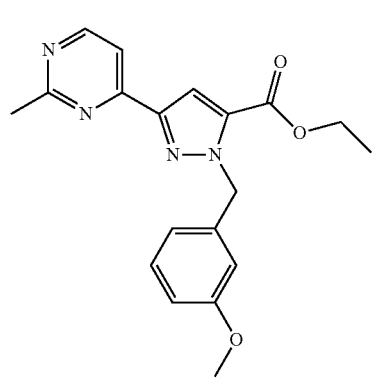

To a solution of 13 mg (37 μmol) of ethyl 1-(3-methoxybenzyl)-3-(2-methylpyrimidin-4-yl)-1H-pyrazole-5-carboxylate in 1 mL of EtOH, 500 μL (0.48 mmol) of concentrated ammonium hydroxide were added. The reaction was stirred at 120° C. for 4 h. The solvent was removed to obtain the desired compound in quantitative yield.

LC/MS (254 nm) HPLC method 2: Rt 3.97 min $^1$H NMR (600 MHz, DMSO-d$_6$) δ ppm 8.70 (d, J=5.3 Hz, 1 H), 8.17 (br. s., 1 H), 7.73 (d, J=5.3 Hz, 1 H), 7.65 (s, 1H), 7.63 (br. s., 1 H), 7.23 (t, J=8.0 Hz, 1 H), 6.83 (dd, J=8.2, 2.1 Hz, 1 H), 6.70-6.76 (m, 2 H), 5.83 (s, 2 H), 3.70 (s, 3 H), 2.65 (s, 3 H)

HRMS (ESI) calcd for C$_{17}$H$_{18}$N$_5$O$_2$ [M+H]$^+$ 324.1455. found 324.1461.

Example 10

Ethyl 3-(2-hydroxypyrimidin-4-yl)-1-(3-methoxybenzyl)-1H-pyrazole-5-carboxylate [(Ib) R1=H, X=—O—, R2=3-methoxybenzyl, R3=COOEt, R4=H]

step 6

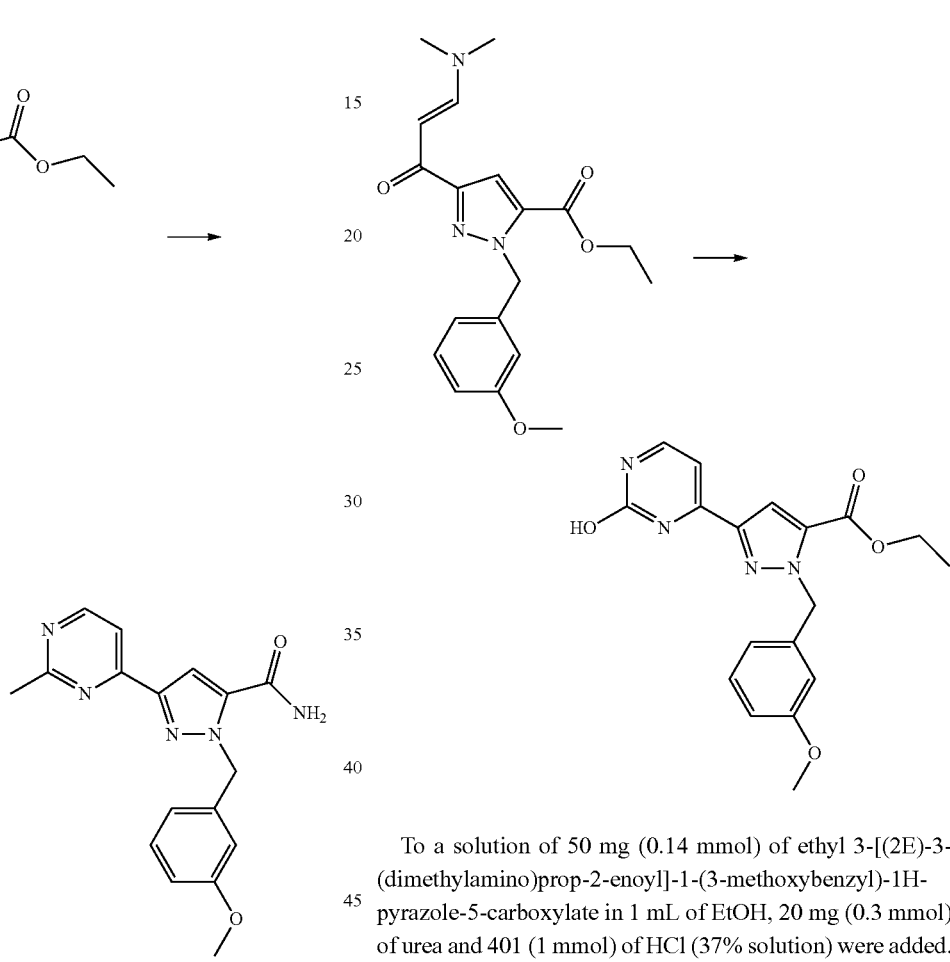

To a solution of 50 mg (0.14 mmol) of ethyl 3-[(2E)-3-(dimethylamino)prop-2-enoyl]-1-(3-methoxybenzyl)-1H-pyrazole-5-carboxylate in 1 mL of EtOH, 20 mg (0.3 mmol) of urea and 401 (1 mmol) of HCl (37% solution) were added. The reaction was stirred at 120° C. for 2 h. The solvent was removed, the residue was dissolved in DCM and the solid filtered off. The organic solution was evaporated and the crude was washed with AcOEt to give the title product (70%).

LC/MS (254 nm) HPLC method 2: Rt 4.43 min $^1$H NMR (600 MHz, DMSO-d$_6$) δ ppm 8.06 (d, J=6.0 Hz, 1 H), 7.51 (s, 1 H), 7.23-7.27 (m, 1 H), 6.95 (d, J=6.2 Hz, 1 H), 6.86 (dd, J=8.3, 2.1 Hz, 1 H), 6.77 (s, 1 H), 6.72 (d, J=7.5 Hz, 1 H), 5.74-5.80 (m, 2 H), 4.31 (q, J=7.1 Hz, 2 H), 3.67-3.73 (m, 3 H), 1.25-1.33 (m, 3 H).

HRMS (ESI) calcd for C$_{18}$H$_{19}$N$_4$O$_4$ [M+H]$^+$ 355.1401. found 355.1394.

According to the same method, but employing 3-[(2E)-3-(dimethylamino)prop-2-enoyl]-1-(3-methoxybenzyl)-1H-pyrazole-5-carboxamide, the following compound was prepared:

3-(2-hydroxy-pyrimidin-4-yl)-1-(3-methoxy-benzyl)-1H-pyrazole-5-carboxamide [(Ib) R1=H, X=—O—, R2=3-methoxybenzyl, R3=CONH₂, R4=H] cpd 23

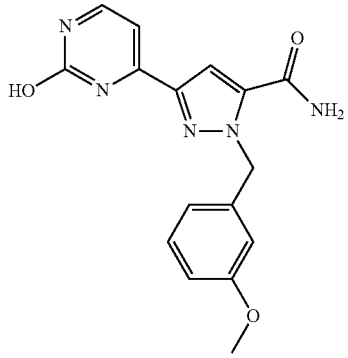 [SMILES: COc1cccc(Cn2nc(-c3ccnc(O)n3)cc2C(N)=O)c1]

LC/MS (254 nm) HPLC method 2: Rt 3.28 min

¹H NMR (600 MHz, DMSO-d₆) δ ppm 8.53 (s, 1 H), 8.16 (s, 1 H), 7.93 (d, J=6.1 Hz, 1 H), 7.66 (br. s., 1 H), 7.56 (s, 1 H), 7.23 (t, J=7.9 Hz, 1 H), 6.78-6.88 (m, 2 H), 6.67-6.76 (m, 2 H), 5.81 (s, 2 H), 3.70 (s, 3 H)

HRMS (ESI) calcd for $C_{16}H_{16}N_5O_3$ [M+H]⁺ 326.1248. found 326.1252.

Preparation H

Ethyl 3-acetyl-1-(5-chloro-2-methylphenyl)-1H-pyrazole-5-carboxylate [(IVc) R2'''=5-chloro-2-methylphenyl, R3=COOEt] and ethyl 5-acetyl-1-(5-chloro-2-methylphenyl)-1H-pyrazole-3-carboxylate [(IVc) R2'''=5-chloro-2-methylphenyl, R3=COOEt]

step 3

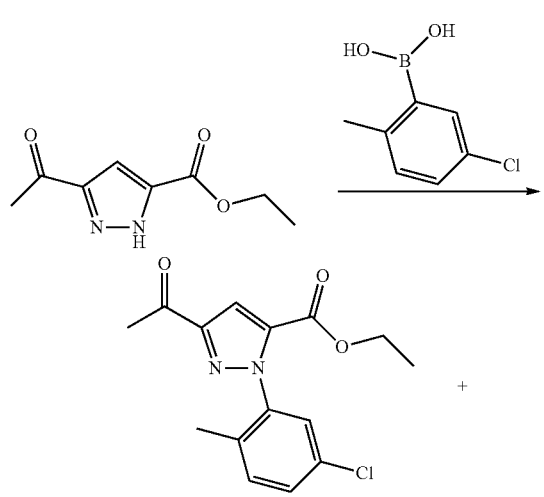

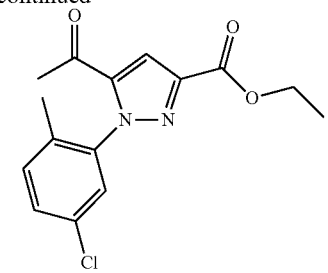

A mixture of ethyl 3-acetyl-1H-pyrazole-5-carboxylate (364 mg, 2.0 mmol), (5-chloro-2-methylphenyl)boronic acid (680 mg, 4.0 mmol), copper(II) acetate (571 mg, 3.0 mmol) and pyridine (0.32 mL, 4 mmol) in DCM (10 mL) was stirred at r.t. under an air atmosphere for 48 h. After removal of the insolubles by filtration, the filtrate was washed with water and saturated brine, dried over anhydrous sodium sulfate, concentrated in vacuo and purified by flash chromatography (hexane/AcOEt, 90/10) to obtain ethyl 3-acetyl-1-(5-chloro-2-methylphenyl)-1H-pyrazole-5-carboxylate as a white solid (269 mg, 43%), ¹H NMR (400 MHz, DMSO-d₆) δ ppm 7.58-7.59 (m, 1 H) 7.54-7.58 (m, 1 H) 7.45 (d, J=8.18 Hz, 1 H) 7.44 (s, 1 H) 4.17 (q, J=7.08 Hz, 2 H) 2.54 (s, 3 H) 1.94 (s, 3 H) 1.12 (t, J=7.08 Hz, 3 H)

HRMS (ESI) calcd for $C_{15}H_{16}ClN_2O_3$[M+H]⁺ 307.0844. found 307.0844;

and ethyl 5-acetyl-1-(5-chloro-2-methylphenyl)-1H-pyrazole-3-carboxylate as an oil (220 mg, 36%)

¹H NMR (400 MHz, DMSO-d₆) δ ppm 7.82 (s, 1H) 7.56 (dd, J=8.18, 2.32 Hz, 1H) 7.44 (d, J=2.32 Hz, 1H) 7.42 (d, J=8.54 Hz, 1H) 4.34 (q, J=7.12 Hz, 2H) 2.54 (s, 3H) 1.87 (s, 3H) 1.32 (t, J=7.08 Hz, 3H)

HRMS (ESI) calcd for $C_{15}H_{16}ClN_2O_3$[M+H]⁺ 307.0844. found 307.0850.

According to the same method, but employing 5-chloro-2-ethylphenyl)boronic acid, the following compounds were prepared:

Ethyl 3-acetyl-1-(5-chloro-2-ethylphenyl)-1H-pyrazole-5-carboxylate [(IVc) R2'''=5-chloro-2-ethylphenyl, R3=COOEt]

¹H NMR (400 MHz, DMSO-d₆) δ ppm 7.57-7.62 (m, 2H) 7.49 (d, J=7.92 Hz, 1H) 7.44 (s, 1H) 4.16 (q, J=7.16 Hz, 1H) 2.53 (s, 1H) 2.23 (q, J=7.45 Hz, 1H) 1.11 (t, J=7.14 Hz, 1H) 0.99 (t, J=7.57 Hz, 1H)

HRMS (ESI) calcd for $C_{16}H_{18}ClN_2O_3$ [M+H]⁺ 321.1001. found 321.1006.

Ethyl 5-acetyl-1-(5-chloro-2-ethylphenyl)-1H-pyrazole-3-carboxylate [(IVc) R2'''=5-chloro-2-ethylphenyl, R3=COOEt]

¹H NMR (400 MHz, DMSO-d₆) δ ppm 7.81 (s, 1H) 7.56 (dd, J=8.36, 2.26 Hz, 1H) 7.45 (d, J=8.42 Hz, 1H) 7.43 (d, J=2.32 Hz, 1H) 4.34 (q, J=7.12 Hz, 2H) 2.53 (s, 3H) 2.17 (q, J=7.69 Hz, 2H) 1.32 (t, J=7.14 Hz, 3H) 0.94 (t, J=7.57 Hz, 3H)

HRMS (ESI) calcd for $C_{16}H_{18}ClN_2O_3$ [M+H]⁺ 321.1001. found 321.1004.

Preparation I

Ethyl 1-(5-chloro-2-methylphenyl)-3-[(2E)-3-(dimethylamino)prop-2-enoyl]-1H-pyrazole-5-carboxylate [(VI), R2=5-chloro-2-methylphenyl, R3=COOEt]

step 5

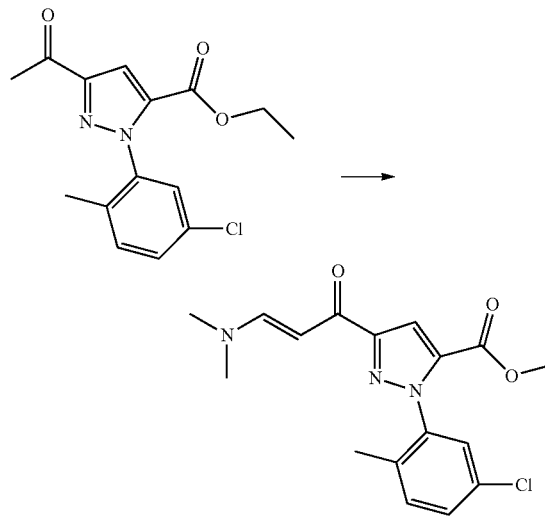

To a suspension of ethyl 3-acetyl-1-(5-chloro-2-methylphenyl)-1H-pyrazole-5-carboxylate (250 mg, 0.81 mmol) in DMF (3 mL), N,N-dimethylformamide diisopropyl acetal (0.512 mL, 2.45 mmol) was added. The mixture was stirred at 90° C. for 3 h. The mixture was evaporated in vacuo and used in the next step without any further purification (280 mg, 95%).

$^1$H NMR (400 MHz, DMSO-d$_6$) δ ppm 7.70-7.86 (m, 1H), 7.48-7.61 (m, 2H), 7.40-7.47 (m, 1H), 7.34 (s, 1H), 5.84 (d, J=12.57 Hz, 1H), 4.16 (q, J=7.08 Hz, 2H), 3.15 (s, 3H), 2.86 (s, 3H), 1.92 (s, 3H), 1.14 (t, J=7.08 Hz, 2H)

HRMS (ESI) calcd for C$_{18}$H$_{21}$ClN$_3$O$_3$[M+H]$^+$ 362.1266. found 362.1260.

According to the same method the following compounds were prepared:

Ethyl 1-(5-chloro-2-methylphenyl)-5-[(2E)-3-(dimethylamino)prop-2-enoyl]-1H-pyrazole-3-carboxylate [(VI), R2=5-chloro-2-methylphenyl, R3=COOEt]

$^1$H NMR (400 MHz, DMSO-d$_6$) δ ppm 7.58 (d, J=12.33 Hz, 1H), 7.54 (s, 1H), 7.43-7.48 (m, 1H), 7.31-7.39 (m, 2H), 5.70 (d, J=12.21 Hz, 1H), 4.32 (q, J=7.16 Hz, 2H), 3.10 (s, 3H), 2.89 (s, 3H), 1.86 (s, 3H), 1.31 (t, J=7.08 Hz, 3H) HRMS (ESI) calcd for C$_{18}$H$_{21}$ClN$_3$O$_3$[M+H]$^+$ 362.1266. found 362.1261.

Ethyl 1-(5-chloro-2-ethylphenyl)-3-[(2E)-3-(dimethylamino)prop-2-enoyl]-1H-pyrazole-5-carboxylate [(VI), R2=5-chloro-2-ethylphenyl, R3=COOEt]

HRMS (ESI) calcd for C$_{19}$H$_{23}$ClN$_3$O$_3$[M+H]$^+$ 376.8493. found 376.8386.

Ethyl 1-(5-chloro-2-ethylphenyl)-5-[(2E)-3-(dimethylamino)prop-2-enoyl]-1H-pyrazole-3-carboxylate [(VI), R2=5-chloro-2-ethylphenyl, R3=COOEt]

HRMS (ESI) calcd for C$_{19}$H$_{23}$ClN$_3$O$_3$[M+H]$^+$ 376.8493. found 376.8389.

Example 11

3-(2-Aminopyrimidin-4-yl)-1-(5-chloro-2-methylphenyl)-1H-pyrazole-5-carboxylic acid [(Ib), R1=NH$_2$, X=single bond, R2=5-chloro-2-methylphenyl, R3=COOH, R4=H]

step 6

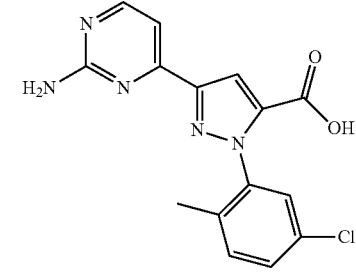

To a mixture of ethyl 1-(5-chloro-2-methylphenyl)-3-[(2E)-3-(dimethylamino)prop-2-enoyl]-1H-pyrazole-5-carboxylate (260 mg, 0.72 mmol) in DMF (4 mL), guanidine carbonate (130 mg, 0.72 mmol) was added. The mixture was heated at 110° C. overnight under efficient stirring. The resulting mixture was concentrated, dissolved in MeOH (0.5 mL) and THF (0.5 mL) and treated with NaOH 1N (0.5 mL). After 1 h the mixture was concentrated, dissolved in water and washed with AcOEt. To the aqueous phase cooled to 5° C., a saturated solution of citric acid was added under stirring. The resulting precipitate was collected by filtration to give the title compound (156 mg, 65%).

$^1$H NMR (400 MHz, DMSO-d$_6$) δ ppm 8.29 (d, J=5.00 Hz, 1H), 7.49-7.55 (m, 2H), 7.46 (s, 1H), 7.40-7.44 (m, 1H), 7.09 (d, J=5.00 Hz, 1H), 6.70 (s, 2H)

HRMS (ESI) calcd for C$_{15}$H$_{13}$ClN$_5$O$_2$[M+H]$^+$ 330.0753. found 330.0749.

According to the same method the following compounds were prepared:

5-(2-Aminopyrimidin-4-yl)-1-(5-chloro-2-methylphenyl)-1H-pyrazole-3-carboxylic acid [(Ia), R1=NH₂, X=single bond, R2=5-chloro-2-methylphenyl, R3=COOH, R4=H]

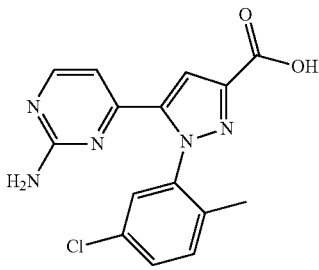 [SMILES: Cc1ccc(Cl)cc1-n1nc(C(=O)O)cc1-c1ccnc(N)n1]

¹H NMR (401 MHz, DMSO-d₆) δ ppm 13.10 (s, 1H), 8.21 (d, J=5.13 Hz, 1H), 7.51-7.56 (m, 1H), 7.48-7.50 (m, 1H), 7.42 (d, J=8.42 Hz, 1H), 7.40 (s, 1H), 6.47 (bs, 2H), 6.44 (d, J=5.13 Hz, 1H), 1.88 (s, 3H)
HRMS (ESI) calcd for $C_{15}H_{13}ClN_5O_2[M+H]^+$ 330.0753. found 330.0748.

3-(2-Aminopyrimidin-4-yl)-1-(5-chloro-2-ethylphenyl)-1H-pyrazole-5-carboxylic acid [(Ib), R1=NH₂, X=single bond, R2=5-chloro-2-ethylphenyl, R3=COOH, R4=H]

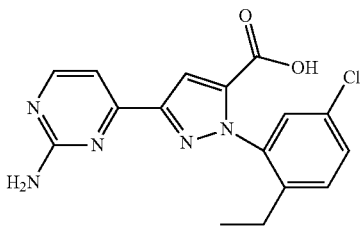 [SMILES: CCc1ccc(Cl)cc1-n1nc(-c2ccnc(N)n2)cc1C(=O)O]

¹H NMR (400 MHz, DMSO-d₆) δ ppm 8.29 (d, J=5.00 Hz, 1H), 7.52-7.57 (m, 2H), 7.44-7.47 (m, 2H), 7.08 (d, J=5.00 Hz, 1H), 6.70 (s, 2H), 2.25 (q, J=7.45 Hz, 2H), 0.98 (t, J=7.57 Hz, 3H)
HRMS (ESI) calcd for $C_{16}H_{15}ClN_5O_2[M+H]^+$ 344.0909. found 344.0911.

5-(2-Aminopyrimidin-4-yl)-1-(5-chloro-2-ethylphenyl)-1H-pyrazole-3-carboxylic acid [(Ia), R1=NH₂, X=single bond, R2=5-chloro-2-ethylphenyl, R3=COOH, R4=H]

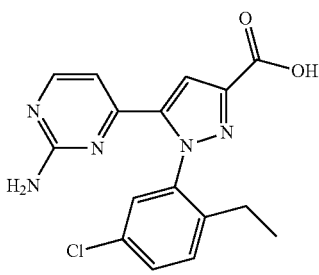 [SMILES: CCc1ccc(Cl)cc1-n1nc(C(=O)O)cc1-c1ccnc(N)n1]

¹H NMR (400 MHz, DMSO-d₆) δ ppm 8.20 (d, J=5.13 Hz, 1H), 7.58 (dd, J=2.26, 8.36 Hz, 1H), 7.48-7.50 (m, 1H), 7.46 (d, J=8.42 Hz, 2H), 7.40 (s, 1H), 6.47 (bs, 2H), 6.40 (d, J=5.13 Hz, 2H), 2.19 (q, J=7.57 Hz, 2H), 0.91 (t, J=7.57 Hz, 3H)
HRMS (ESI) calcd for $C_{16}H_{15}ClN_5O_2[M+H]^+$ 344.0909. found 344.0913.

Example 12

3-(2-Aminopyrimidin-4-yl)-1-(5-chloro-2-methylphenyl)-1H-pyrazole-5-carboxamide [(Ib), R1=NH₂, X=single bond, R2=5-chloro-2-methylphenyl, R3=CONH₂, R4=H] cpd 18 conv. b

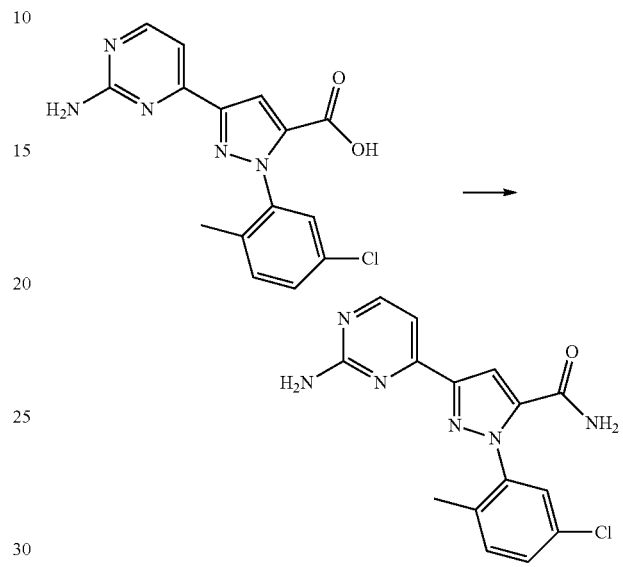

A solution of 3-(2-aminopyrimidin-4-yl)-1-(5-chloro-2-methylphenyl)-1H-pyrazole-5-carboxylic acid (147 mg, 0.45 mmol) in DMF (3 mL) and DIPEA (0.313, 1.8 mmol) was stirred at 0° C. TBTU (217 mg, 0.675 mmol) and NH₄Cl (36 mg, 0.675 mmol) were added and the reaction mixture was stirred for 3 h at r.t. The mixture was then diluted with a saturated solution of sodium hydrogen carbonate, and extracted with AcOEt, dried over anhydrous sodium sulfate, concentrated in vacuo and purified by flash chromatography (DCM/MeOH, 95/5) to obtain the title compound (96 mg, 65%).
¹H NMR (401 MHz, DMSO-d₆) δ ppm 8.28 (d, J=5.13 Hz, 1H), 8.18 (bs, 1H), 7.55 (s, 1H), 7.52 (bs, 1H), 7.45-7.50 (m, 1H), 7.34-7.42 (m, 2H), 7.06 (d, J=5.13 Hz, 1H), 6.63 (s, 2H), 1.94 (s, 3H)
HRMS (ESI) calcd for $C_{15}H_{14}ClN_6O [M+H]^+$ 329.0912. found 329.0911.
According to the same method the following compounds were prepared:

5-(2-aminopyrimidin-4-yl)-1-(5-chloro-2-methylphenyl)-1H-pyrazole-3-carboxamide [(Ia), R1=NH₂, X=single bond, R2=5-chloro-2-methylphenyl, R3=CONH₂, R4=H] cpd 17

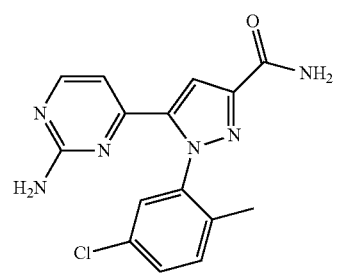 [SMILES: Cc1ccc(Cl)cc1-n1nc(C(N)=O)cc1-c1ccnc(N)n1]

$^1$H NMR (400 MHz, DMSO-d$_6$) δ ppm 8.20 (d, J=5.13 Hz, 1H), 7.74 (s, 1H), 7.50-7.55 (m, 1H), 7.47-7.50 (m, 1H), 7.41 (d, J=8.18 Hz, 1H), 7.39 (bs, 1H), 6.47 (bs, 1H), 6.43 (d, J=5.00 Hz, 1H), 1.90 (s, 3H)

HRMS (ESI) calcd for C$_{15}$H$_{14}$ClN$_6$O [M+H]$^+$ 329.0912. found 329.0913.

3-(2-Aminopyrimidin-4-yl)-1-(5-chloro-2-ethylphenyl)-1H-pyrazole-5-carboxamide [(Ib), R1=NH$_2$, X=single bond, R2=5-chloro-2-ethylphenyl, R3=CONH$_2$, R4=H] cpd 15

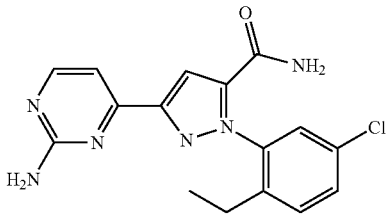

$^1$H NMR (401 MHz, DMSO-d$_6$) δ ppm 8.28 (d, J=5.13 Hz, 1H), 8.18 (bs, 1H), 7.55 (s, 1H), 7.47-7.53 (m, 2H), 7.40-7.44 (m, 1H), 7.39 (d, J=2.20 Hz, 1H), 7.06 (d, J=5.00 Hz, 1H), 6.65 (bs, 2H), 2.25 (q, J=7.61 Hz, 2H), 0.98 (t, J=7.57 Hz, 3H)

HRMS (ESI) calcd for C$_{16}$H$_{16}$ClN$_6$O [M+H]$^+$ 343.1069. found 343.1068.

5-(2-aminopyrimidin-4-yl)-1-(5-chloro-2-ethylphenyl)-1H-pyrazole-3-carboxamide [(Ia), R1=NH$_2$, X=single bond, R2=5-chloro-2-ethylphenyl, R3=CONH$_2$, R4=H] cpd 16

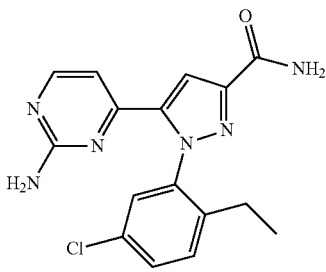 [SMILES: CCc1ccc(Cl)cc1-n1nc(C(N)=O)cc1-c1ccnc(N)n1]

$^1$H NMR (400 MHz, DMSO-d$_6$) δ ppm 8.20 (d, J=5.25 Hz, 1H), 7.73 (s, 1H), 7.51-7.61 (m, 1H), 7.51 (d, J=2.20 Hz, 1H), 7.45 (d, J=8.42 Hz, 1H), 7.39 (s, 1H), 7.37 (s, 1H), 6.56 (bs, 1H), 6.42 (d, J=5.13 Hz, 1H), 2.21 (q, J=7.49 Hz, 2H), 0.92 (t, J=7.57 Hz, 3H)

HRMS (ESI) calcd for C$_{16}$H$_{16}$ClN$_6$O [M+H]$^+$ 343.1069. found 343.1065.

Preparation J

Ethyl 4-[2-(methylsulfanyl)pyrimidin-4-yl]-2,4-dioxobutanoate [(X) R1=Me, X=—S—, R4=H, R3=COOEt]

Step 7

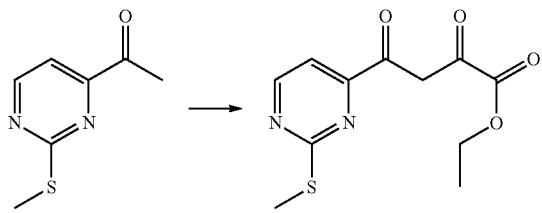 [SMILES: CSc1nccc(C(C)=O)n1 ; CCOC(=O)C(=O)CC(=O)c1ccnc(SC)n1]

In a 250 mL, three-necked, round-bottomed flask equipped with a thermometer, magnetic stirrer, under nitrogen atmosphere, cooled to −7° C. with an ice/NaCl bath, anhydrous THF (10 mL) was loaded and sodium tert-butoxide 1.26 g (13.1 mmol, 2.2 eq.) was added in small portions. The addition was slightly exothermic. The solid dissolved completely within 15 min yielding a white, turbid solution. Diethyl oxalate 2.41 mL (17.83 mmol, 3 eq.) diluted in 10 mL of THF was loaded into the addition funnel and added dropwise to the solution at −7° C. The addition was again slightly exothermic and took about 20 min, meanwhile the solution color changed to light yellow. Once the addition was complete the mixture was stirred at the same temperature for 30 min. and then cooled to −11° C. 1-(2-Methylsulfanyl-pyrimidin-4-yl)-ethanone 1 g (5.94 mmol) was dissolved in 14 mL of THF, loaded into the addition funnel and added dropwise to the cooled mixture. The temperature was kept below −8° C. throughout the addition, which took 20 min. The mixture was stirred for 1 h in the cold and then for 1 further h at r.t. The reaction mass was poured into an ice cooled biphasic mixture made of 50 mL 5% citric acid and 50 mL AcOEt under vigorous stirring. The aqueous layer was separated and extracted again with 50 mL of AcOEt. The combined organic extracts were then concentrated to a dark yellow oil which contained a variable amount of diethyl oxalate. This raw material was used as such in the following step.

LC/MS (254 nm) HPLC method 3: Rt 3.13 min

Example 13

Ethyl 5-[2-(methylsulfanyl)pyrimidin-4-yl]-1H-pyrazole-3-carboxylate [(I) R1=Me, X=—S—, R2 and R4=H, R3=COOEt]

step 8

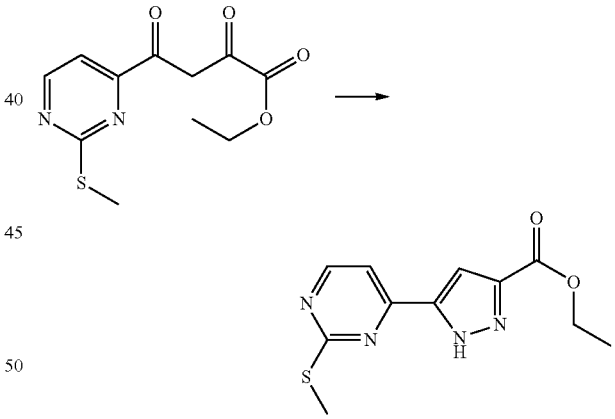

The raw material of preparation J was suspended in 59 mL of abs. EtOH, then hydrazine hydrate 343 μL (7.08 mmol) and AcOH 354 μL (6.2 mmol) were added. The final mixture was stirred at r.t. for 1 h, then concentrated under reduced pressure. The residue was partitioned between H$_2$O and AcOEt, the organic layer was washed with brine, dried over Na$_2$SO$_4$, filtered and concentrated under reduced pressure. The residue was purified by flash chromatography (AcOEt:hexane 1:4) to give the title compound (60% over two steps).

LC/MS (254 nm) HPLC method 3: Rt 4.78 min $^1$H NMR (600 MHz, DMSO-d$_6$) δ ppm 13.94-14.66 (m, 1H), 8.68 (br. s., 1H), 7.69 (d, J=5.13 Hz, 1H), 7.5 (br. s., 1H), 4.24-4.46 (m, J=6.23 Hz, 2H), 2.56-2.63 (m, 3H), 1.33 (t, J=7.14 Hz, 3H)

Example 14

Ethyl 1-tert-butyl-5-[2-(methylsulfanyl)pyrimidin-4-yl]-1H-pyrazole-3-carboxylate [(Ia) R1=Me, X=—S—, R2=t-butyl, R3=COOEt, R4=H]

step 8

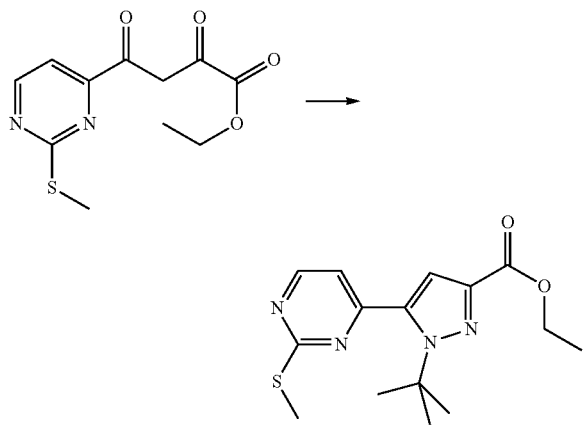

The raw material of preparation J was suspended in 59 mL of abs. EtOH, and tert-butylhydrazine hydrochloride (882.24 mg, 7.08 mmol), sodium acetate (580.56 mg, 7.08 mmol) and AcOH (1.62 mL, 28.32 mmol) were added. The final mixture was stirred at 80° C. for 2 h, then concentrated under reduced pressure. The residue was partitioned between $H_2O$ and AcOEt. The organic layer was washed with brine dried over $Na_2SO_4$, filtered and concentrated under reduced pressure. The residue was purified by flash chromatography (AcOEt:hexane 1:4) to give the title compound (53% over two steps).

LC/MS (254 nm) HPLC method 3: Rt 6.35 min $^1$H NMR (600 MHz, DMSO-$d_6$) δ ppm 8.73 (d, J=4.95 Hz, 1H), 7.41 (d, J=4.95 Hz, 1H), 7.02 (s, 1H), 4.27 (q, J=7.02 Hz, 2H), 2.52 (s, 3H), 1.54 (s, 9H), 1.27 (t, J=7.14 Hz, 3H)

HRMS (ESI) calcd for $C_{15}H_{21}N_4O_2S$ [M+H]$^+$ 321.1380. found 321.1380.

Example 15

5-[2-(methylsulfanyl)pyrimidin-4-yl]-1H-pyrazole-3-carboxylic acid [(I) R1=Me, X=—S—, R2=H, R3=COOH, R4=H]

conv. a

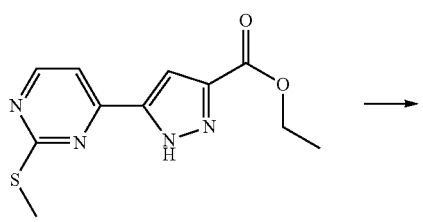

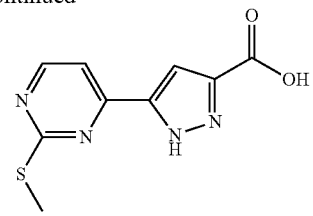

Ethyl 5-[2-(methylsulfanyl)pyrimidin-4-yl]-1H-pyrazole-3-carboxylate (50 mg, 0.19 mmol) was dissolved in 1 mL of THF and LiOH (22.6 mg, 0.95 mmol) dissolved in water (0.5 mL) was added. The biphasic mixture was homogenized with few drops of MeOH. The final mixture was heated by microwave irradiation to 100° C. for 30 min. The pH was adjusted to 5 with 2N HCl, the organic volatiles were removed under reduced pressure and the precipitate was collected by filtration to provide the title compound (90%).

LC/MS (254 nm) HPLC method 3: Rt 1.79 min $^1$H NMR (600 MHz, DMSO-$d_6$) δ ppm 13.81-14.64 (m, 1H), 8.42-8.73 (m, 1H), 7.63-7.71 (m, 1H), 7.46-7.56 (m, 1H), 7.27-7.40 (m, 1H), 2.55-2.60 (m, 3H)

HRMS (ESI) calcd for $C_9H_9N_4O_2S$ [M+H]$^+$ 237.0441. found 237.0441.

Example 16

5-[2-(methylsulfanyl)pyrimidin-4-yl]-1H-pyrazole-3-carboxamide [(I) R1=Me, X=—S—, R2=H, R3=CONH$_2$, R4=H] cpd 19 conv. c

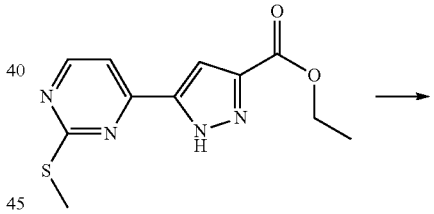

250 mg (0.95 mmol) of ethyl 5-[2-(methylsulfanyl)pyrimidin-4-yl]-1H-pyrazole-3-carboxylate were dissolved in 4 mL of NH$_3$ 7N in MeOH. The solution was heated at 120° by microwave irradiation, with cooling function activated, for 2 h. The precipitate obtained was collected by filtration to provide the title compound (78%).

LC/MS (254 nm) HPLC method 3: Rt 2.88 min.

$^1$H NMR (600 MHz, DMSO-$d_6$) δ ppm 13.65-14.39 (m, 1H), 8.65 (br. s., 1H), 8.07 (br. s., 1H), 7.64 (d, J=5.13 Hz, 1H), 7.55 (br. s., 2H), 2.58 (s, 3H)

HRMS (ESI) calcd for $C_9H_{10}N_5OS$ [M+H]$^+$ 236.0601. found 236.0608.

Example 17 tert-butyl 4-{3-carbamoyl-5-[2-(methylsulfanyl)pyrimidin-4-yl]-1H-pyrazol-1-yl}piperidine-1-carboxylate [(Ia) R1=Me, X=—S—, R2=t-butyl-4-piperidinyl-1-carboxylate, R3=CONH₂, R4=H] and tert-butyl 4-{5-carbamoyl-3-[2-(methylsulfanyl)pyrimidin-4-yl]-1H-pyrazol-1-yl}piperidine-1-carboxylate [(Ib) R1=Me, X=—S—, R2=t-butyl-4-piperidinyl-1-carboxylate, R3=CONH₂, R4=H]

conv. j

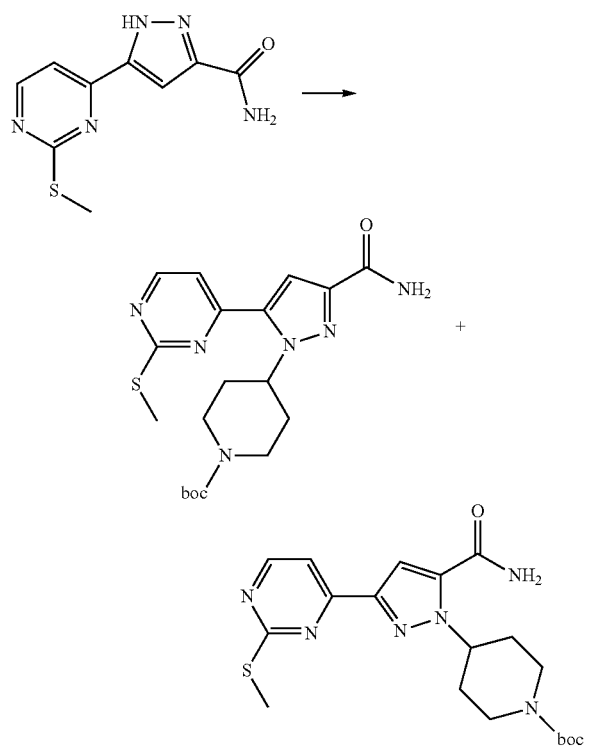

45 mg of 5-[2-(methylsulfanyl)pyrimidin-4-yl]-1H-pyrazole-3-carboxamide and cesium carbonate (123.27 mg, 0.38 mmol) were dissolved in 2 mL of anhydrous DMF, 106.87 mg of t-butyl-4-[(methyl-sulfonyl)oxy]piperidine-1-carboxylate (0.38 mmol) was added and stirred at 80° C. overnight. The mixture was partitioned between H₂O and AcOEt. The organic layer was washed with brine, dried over Na₂SO₄, filtered and concentrated under reduced pressure. The residue was purified by preparative HPLC/MS to provide the two regioisomers, tert-butyl 4-{3-carbamoyl-5-[2-(methylsulfanyl)pyrimidin-4-yl]-1H-pyrazol-1-yl}piperidine-1-carboxylate (32% yield)

¹H NMR (600 MHz, DMSO-d₆) δ ppm 8.70 (d, J=5.13 Hz, 1H), 7.63 (d, J=5.13 Hz, 1H), 7.60 (s, 1H), 7.37 (s, 1H), 7.33 (s, 1H), 5.39-5.56 (m, J=7.33, 7.33 Hz, 1H), 4.11 (d, J=9.71 Hz, 2H), 2.75-2.98 (m, 2H), 2.58 (s, 3H), 1.95-2.05 (m, 4H), 1.42 (s, 9H)

HRMS (ESI) calcd for C₁₉H₂₇N₆O₃S [M+H]⁺ 419.1860. found 419.1859;

and tert-butyl 4-{5-carbamoyl-3-[2-(methylsulfanyl)pyrimidin-4-yl]-1H-pyrazol-1-yl}piperidine-1-carboxylate (44% yield)

¹H NMR (600 MHz, DMSO-d₆) δ ppm 8.64 (d, J=5.31 Hz, 1H), 8.15 (s, 1H), 7.65 (br. s., 1H), 7.62 (d, J=5.13 Hz, 1H), 7.59 (s, 1H), 5.40-5.56 (m, 1H), 4.08 (d, J=9.16 Hz, 2H), 2.76-2.99 (m, 2H), 2.57 (s, 3H), 1.77-2.05 (m, 4H), 1.35-1.53 (m, 9H)

HRMS (ESI) calcd for C₁₉H₂₇N₆O₃S [M+H]⁺ 419.1860. found 419.1870.

Example 18 tert-butyl 4-{5-(ethoxycarbonyl)-3-[2-(methylsulfanyl)pyrimidin-4-yl]-1H-pyrazol-1-yl}piperidine-1-carboxylate [(Ib) R1=Me, X=—S—, R2=t-butyl-4-piperidinyl-1-carboxylate, R3=COOEt, R4=H]

conv. j

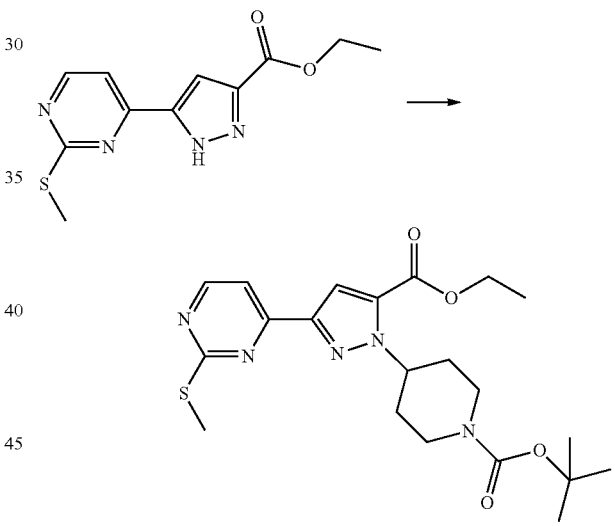

50 mg of ethyl 5-[2-(methylsulfanyl)pyrimidin-4-yl]-1H-pyrazole-3-carboxylate and cesium carbonate 123.27 mg (0.38 mmol) were dissolved in 2 mL of anhydrous DMF, 106.87 mg of t-butyl-4-[(methyl-sulfonyl)oxy]piperidine-1-carboxylate (0.38 mmol) was added and stirred at 80° C. for 3 h. The mixture was partitioned between H₂O and AcOEt. The organic layer was washed with brine dried over Na₂SO₄, filtered and concentrated under reduced pressure. The residue was purified by flash chromatography (AcOEt:hexane 1:9) to give the title compound (70%).

¹H NMR (600 MHz, DMSO-d₆) δ ppm 8.66 (d, J=5.13 Hz, 1H), 7.66 (d, J=5.13 Hz, 1H), 7.46 (s, 1H), 4.99-5.45 (m, 1H), 4.35 (q, J=7.02 Hz, 2H), 4.10 (d, J=8.61 Hz, 2H), 2.79-3.07 (m, 2H), 2.57 (s, 3H), 1.84-2.08 (m, 4H), 1.43 (s, 9H), 1.34 (t, J=7.05 Hz, 3H)

HRMS (ESI) calcd for C₂₁H₃₀N₅O₄S [M+H]⁺ 448.2013. found 448.2028.

Example 19 ethyl 3-[2-(methylsulfanyl)pyrimidin-4-yl]-1-(piperidin-4-yl)-1H-pyrazole-5-carboxylate hydrochloride [(Ib) R1=Me, X=—S—, R2=piperidin-4-yl, R3=COOEt, R4=H]

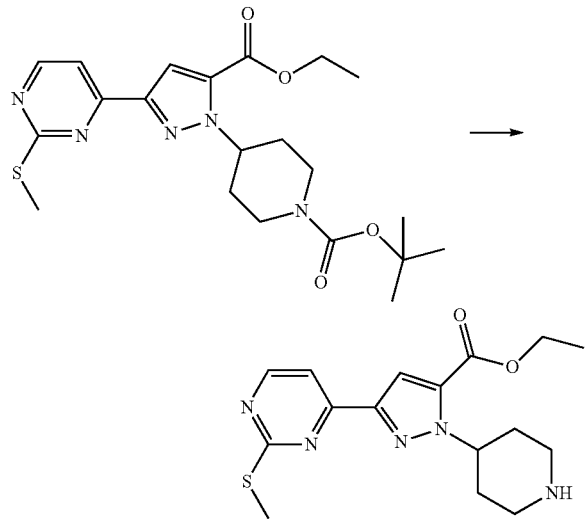

55 mg (0.12 mmol) of tert-butyl 4-{5-(ethoxycarbonyl)-3-[2-(methylsulfanyl)pyrimidin-4-yl]-1H-pyrazol-1-yl}piperidine-1-carboxylate were suspended in 2 mL of HCl 4 N in dioxane and stirred at r.t. overnight. The precipitate was collected by filtration to provide the title compound (90%).

$^1$H NMR (600 MHz, DMSO-$d_6$) δ ppm 8.88 (d, J=8.97 Hz, 1H), 8.70 (d, J=5.31 Hz, 1H), 8.59 (d, J=7.33 Hz, 1H), 7.62 (d, J=5.13 Hz, 1H), 7.32-7.57 (m, 1H), 5.08-5.54 (m, 1H), 4.36 (q, J=7.14 Hz, 2H), 3.45 (d, J=13.00 Hz, 2H), 3.00-3.22 (m, 2H), 2.57 (s, 3H), 2.24-2.35 (m, 2H), 2.14-2.24 (m, 2H), 1.35 (t, J=7.14 Hz, 3H)

HRMS (ESI) calcd for $C_{16}H_{21}N_5O_2S$ [M+H]$^+$ 348.1489. found 348.1496.

Example 20

3-[2-(methylsulfanyl)pyrimidin-4-yl]-1-(piperidin-4-yl)-1H-pyrazole-5-carboxamide hydrochloride [(Ib) R1=Me, X=—S—, R2=piperidin-4-yl, R3=CONH$_2$, R4=H] cpd 22

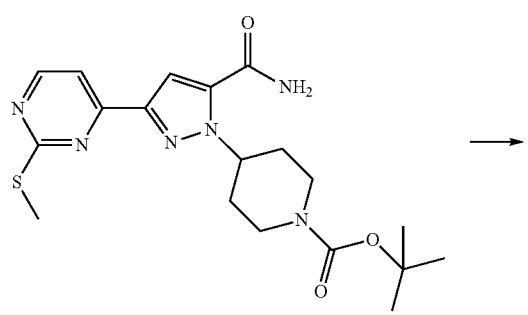

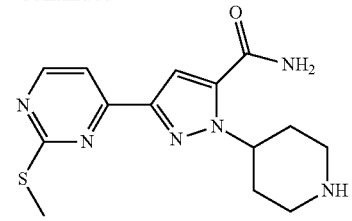

32 mg (0.076 mmol) of tert-butyl 4-{5-carbamoyl-3-[2-(methylsulfanyl)pyrimidin-4-yl]-1H-pyrazol-1-yl}piperidine-1-carboxylate were suspended in 2 mL of HCl 4 N in dioxane and stirred at r.t. overnight. The reaction mixture was dried to provide the title compound (quant.).

$^1$H NMR (600 MHz, DMSO-$d_6$) δ ppm 8.82 (br. s., 1H), 8.68 (d, J=5.13 Hz, 1H), 8.55 (br. s., 1H), 8.19 (s, 1H), 7.70 (s, 1H), 7.63 (s, 1H), 7.57 (d, J=5.13 Hz, 1H), 7.49 (s, 1H), 5.44-5.65 (m, 1H), 3.05-3.15 (m, 2H), 2.56-2.60 (m, 3H), 2.21-2.32 (m, 2H), 2.13-2.20 (m, 2H)

HRMS (ESI) calcd for $C_{14}H_{19}N_6OS$ [M+H]$^+$ 319.1336. found 319.1346.

According to the same method, but employing tert-butyl 4-{3-carbamoyl-5-[2-(methylsulfanyl)pyrimidin-4-yl]-1H-pyrazol-1-yl}piperidine-1-carboxylate, the following compound was prepared:

5-[2-(methylsulfanyl)pyrimidin-4-yl]-1-(piperidin-4-yl)-1H-pyrazole-3-carboxamide hydrochloride [(Ia) R1=Me, X=—S—, R2=piperidin-4-yl, R3=CONH$_2$, R4=H] cpd 21 (quant.)

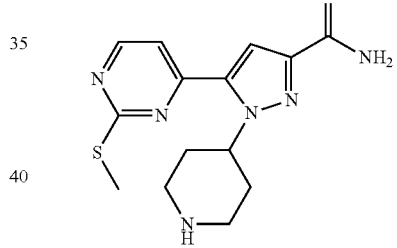

$^1$H NMR (600 MHz, DMSO-$d_6$) δ ppm 8.77 (br. s., 1H), 8.73 (d, J=5.13 Hz, 1H), 8.56 (br. s., 1H), 7.62 (d, J=5.13 Hz, 1H), 7.53 (br. s., 1H), 7.44 (br. s., 1H), 7.41 (s, 1H), 5.44-5.54 (m, 1H), 3.44-3.52 (m, 2H), 2.98-3.09 (m, 2H), 2.59 (s, 3H), 2.26-2.36 (m, 2H), 2.18-2.25 (m, 2H)

HRMS (ESI) calcd for $C_{14}H_{19}N_6OS$ [M+H]$^+$ 319.1336. found 319.1343.

Example 21

1-tert-butyl-5-[2-(methylsulfanyl)pyrimidin-4-yl]-1H-pyrazole-3-carboxamide [(Ia) R1=Me, X=—S—, R2=t-butyl, R3=CONH$_2$, R4=H] cpd 20 conv. c

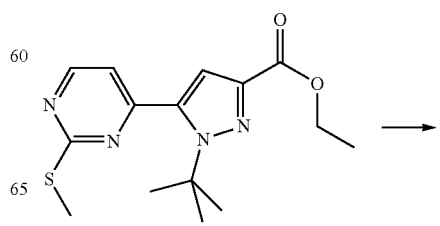

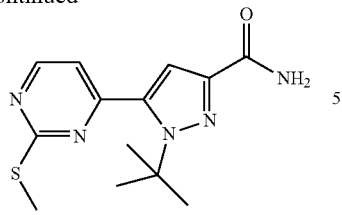

260 mg (0.81 mmol) of ethyl 1-tert-butyl-5-[2-(methylsulfonyl)pyrimidin-4-yl]-1H-pyrazole-3-carboxylate were dissolved in 3.5 mL of NH₃ 7N in MeOH. The solution was heated at 120° by microwave irradiation, with cooling function activated, for 6 h, then concentrated under reduced pressure. The residue was partitioned between H₂O and DCM. The organic layer was washed with brine dried over Na₂SO₄, filtered and concentrated under reduced pressure to provide the title compound (94%).

¹H NMR (600 MHz, DMSO-d₆) δ ppm 8.74 (d, J=4.9 Hz, 1 H), 7.41 (d, J=5.1 Hz, 1 H), 7.29 (br. s., 2 H), 6.91 (s, 1 H), 2.58 (s, 3H), 1.57 ppm (s, 9 H)

HRMS (ESI) calcd for $C_{13}H_{17}N_5NaOS$ [M+Na]⁺ 314.1046. found 314.1046.

Example 22

1-tert-butyl-5-(2-phenylpyrimidin-4-yl)-1H-pyrazole-3-carboxamide [(Ia) R1=phenyl, X=single bond, R2=t-butyl, R3=CONH₂, R4=H] cpd 25 conv. h

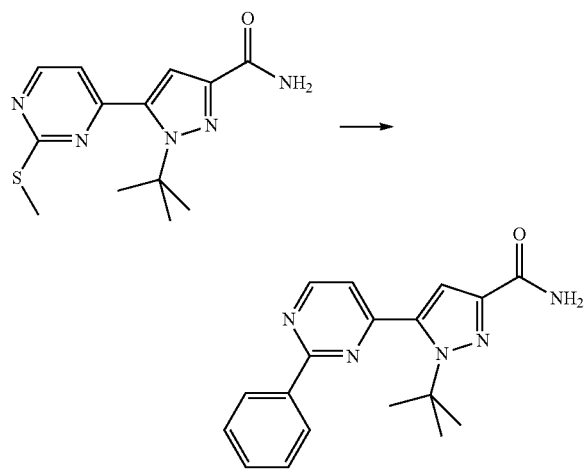

50 mg (0.172 mmol) of 1-tert-butyl-5-[2-(methylsulfanyl)pyrimidin-4-yl]-1H-pyrazole-3-carboxamide, 42 mg (0.343 mmol) of phenyl boronic acid, 98 mg (0.515 mmol) of copper thiophencarboxylate and 20 mg (0.017 mmol) of palladium tetrakis were suspended in 1.5 mL of dry THF under argon atmosphere. The resulting suspension was heated a 130° C. for 1 h by microwave irradiation. The reaction mixture was then filtered on a silica plug, diluted with AcOEt and washed with aqueous NH₄OH. The organic layer was washed with brine, dried over Na₂SO₄, filtered and concentrated under reduced pressure. The residue was purified by preparative HPLC/MS to provide the title compound (23%).

¹H NMR (600 MHz, DMSO-d₆) δ ppm 9.03 (d, J=4.95 Hz, 1H), 8.41 (dd, J=2.93, 6.78 Hz, 2H), 7.66 (d, J=4.95 Hz, 1H), 7.55-7.59 (m, 3H), 7.52 (br. s., 1H), 7.31 (br. s., 1H), 6.98 (s, 1H), 1.63 (s, 9H)

HRMS (ESI) calcd for $C_{18}H_{20}N_5O$ [M+H]⁺ 322.1663. found 322.1659.

Example 23

Ethyl 1-tert-butyl-5-[2-(methylsulfonyl)pyrimidin-4-yl]-1H-pyrazole-3-carboxylate [(Ia) R1=Me, X=—SO₂—, R2=t-butyl, R3=COOEt, R4=H]

conv. d 500 mg (1.56 mmol) of ethyl 1-tert-butyl-5-[2-(methylsulfanyl)pyrimidin-4-yl]-1H-pyrazole-3-carboxylate were dissolved in 16 mL of DCM and 1 g (3.2 mmol) of m-chloroperbenzoic acid was added. The final suspension was stirred at r.t. for 30 min, then the reaction mixture was diluted with 40 mL of DCM and washed twice with NaHCO₃ sat. The organic layer was washed with brine, dried over Na₂SO₄, filtered and concentrated under reduced pressure to provide the title compound (95%).

¹H NMR (600 MHz, DMSO-d₆) δ ppm 9.20 (d, J=5.31 Hz, 1H), 8.13 (d, J=5.13 Hz, 1H), 7.31 (s, 1H), 4.31 (q, J=7.02 Hz, 2H), 3.41-3.48 (m, 3H), 1.62 (s, 9H), 1.30 (t, J=7.05 Hz, 3H)

HRMS (ESI) calcd for $C_{15}H_{21}N_4O_4S$ [M+H]⁺ 375.1097. found 375.1098.

According to the same method, but employing 1-tert-butyl-5-[2-(methylsulfanyl)pyrimidin-4-yl]-1H-pyrazole-3-carboxamide, the following compound was prepared:

1-tert-butyl-5-[2-(methylsulfonyl)pyrimidin-4-yl]-1H-pyrazole-3-carboxamide [(Ia) R1=Me, X=—SO₂—, R2=t-butyl, R3=CONH₂, R4=H] (quant)

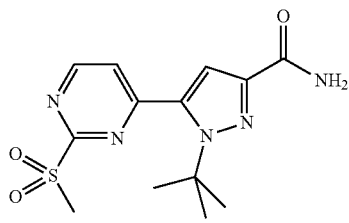 [SMILES: CC(C)(C)n1nc(C(N)=O)cc1-c1ccnc(S(C)(=O)=O)n1]

¹H NMR (600 MHz, DMSO-d₆) δ ppm 9.18 (d, J=5.13 Hz, 1H), 8.10 (d, J=5.13 Hz, 1H), 7.52-7.58 (m, 1H), 7.34 (br. s., 1H), 7.16 (s, 1H), 3.45 (s, 3H), 1.61-1.64 (m, 9H)

Example 24

Ethyl 1-tert-butyl-5-(2-phenoxypyrimidin-4-yl)-1H-pyrazole-3-carboxylate [(Ia) R1=phenyl, X=—O—, R2=t-butyl, R3=COOEt, R4=H]

conv. e

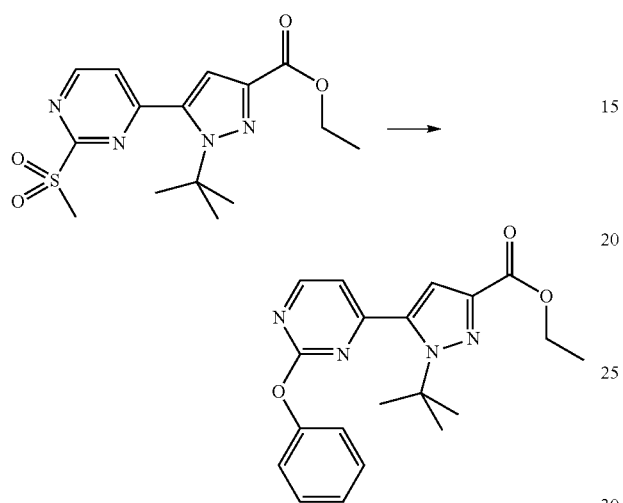

50 mg (0.142 mmol) of ethyl 1-tert-butyl-5-[2-(methylsulfonyl)pyrimidin-4-yl]-1H-pyrazole-3-carboxylate were dissolved in 1.5 mL of dry DMF, 14.7 mg (0.156 mmol) of phenol and 59 mg (0.426 mmol) of potassium carbonate were added. The final suspension was stirred at 70° C. for 3 h then partitioned between H₂O and AcOEt. The organic layer was washed with brine dried over Na₂SO₄, filtered and concentrated under reduced pressure to provide the title compound (77%).

¹H NMR (600 MHz, DMSO-d₆) δ ppm 8.79 (d, J=5.13 Hz, 1H), 7.52 (d, J=4.95 Hz, 1H), 7.42-7.47 (m, 2H), 7.25-7.29 (m, 1H), 7.23 (dd, J=1.01, 8.52 Hz, 2H), 4.28 (q, J=7.14 Hz, 2H), 1.38 (s, 9H), 1.28 (t, J=7.14 Hz, 3H).

HRMS (ESI) calcd for $C_{20}H_{23}N_4O_3$ [M+H]⁺ 367.1765. found 367.1759.

According to this same methodology, but employing suitable substituted derivative, the following compound was prepared:

Ethyl 1-tert-butyl-5-[2-(4-cyanophenoxy)pyrimidin-4-yl]-1H-pyrazole-3-carboxylate [(Ia) R1=p-cyanophenyl, X=—O—, R2=t-butyl, R3=COOEt, R4=H]

¹H NMR (600 MHz, DMSO-d₆) δ ppm 8.83 (d, J=4.95 Hz, 1H), 7.92-7.99 (m, 2H), 7.60 (d, J=5.13 Hz, 1H), 7.48-7.54 (m, 2H), 7.12 (s, 1H), 4.28 (q, J=7.08 Hz, 2H), 1.40 (s, 9H), 1.28 (t, J=7.14 Hz, 3H)

HRMS (ESI) calcd for $C_{21}H_{21}N_5O_3$ [M+H]⁺ 392.1717. found 392.1718.

Example 25

1-tert-butyl-5-{2-[4-(piperazin-1-yl)phenoxy]pyrimidin-4-yl}-1H-pyrazole-3-carboxamide [(Ia) R1=4-(piperazin-yl)phenyl, X=—O—, R2=t-butyl, R3=CONH₂, R4=H] cpd 26 conv. e

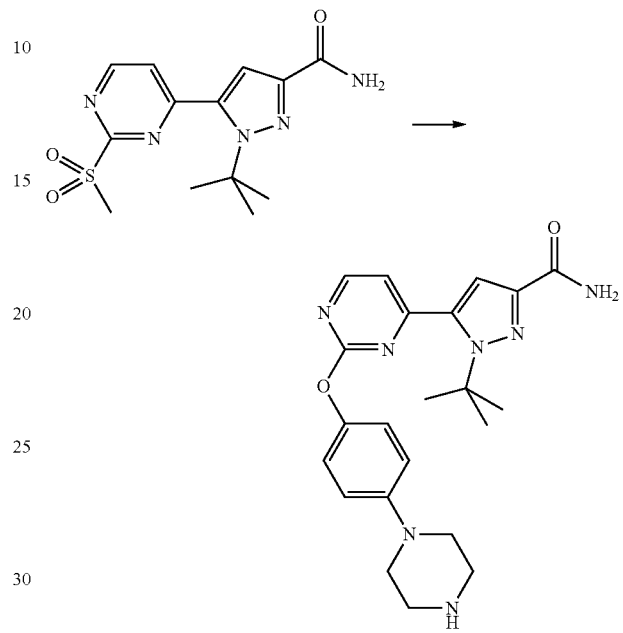

50 mg (0.155 mmol) of 1-tert-butyl-5-[2-(methylsulfonyl)pyrimidin-4-yl]-1H-pyrazole-3-carboxamide were dissolved in 1.5 mL of dry DMF; then, 30 mg (0.17 mmol) of 4-piperazin-1-yl-phenol and 64 mg (0.464 mmol) of potassium carbonate were added. The final suspension was stirred at 70° C. for 1 h then the final mixture was purified by preparative HPLC/MS to provide the title compound (20%).

¹H NMR (600 MHz, DMSO-d₆) δ ppm 8.75 (d, J=4.95 Hz, 1H), 7.44 (d, J=5.13 Hz, 2H), 7.27 (br. s., 1H), 7.03-7.08 (m, 2H), 6.95-6.98 (m, 2H), 6.94 (s, 1H), 3.00-3.07 (m, 4H), 2.85-2.93 (m, 4H), 1.39 (s, 9H)

HRMS (ESI) calcd for $C_{22}H_{28}N_7O_2$ [M+H]⁺ 422.2299. found 422.2303.

According to this same methodology, but employing suitable substituted derivative, the following compound was prepared:

1-tert-butyl-5-(2-methoxypyrimidin-4-yl)-1H-pyrazole-3-carboxamide [(Ia) R1=Me, X=—O—, R2=t-butyl, R3=CONH₂, R4=H] cpd 28

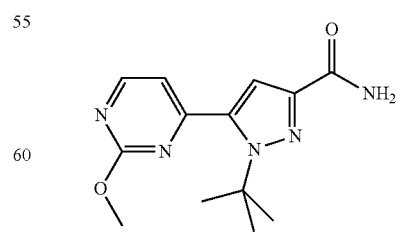

¹H NMR (600 MHz, DMSO-d₆) δ ppm 8.72 (d, J=4.95 Hz, 1H), 7.49 (s, 1H), 7.36 (d, J=4.95 Hz, 1H), 6.91 (s, 1H), 3.96 (s, 3H), 1.60 (s, 9H)

HRMS (ESI) calcd for $C_{13}H_{18}N_5O_2$ [M+H]$^+$ 276.1455. found 276.1459.

Example 26

Ethyl 1-tert-butyl-5-{2-[(1-methyl piperidin-4-yl)amino]pyrimidin-4-yl}-1H-pyrazole-3-carboxylate [(Ia) R1=1-methylpiperazin-4-yl, X=—NH—, R2=t-butyl, R3=COOEt, R4=H]

conv. f

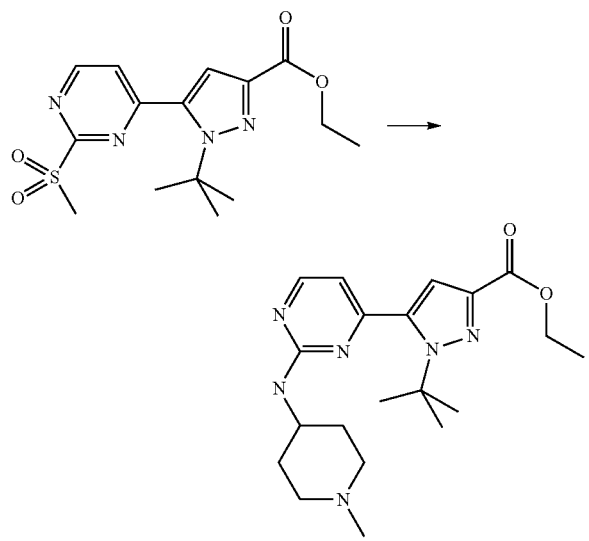

50 mg (0.142 mmol) of ethyl 1-tert-butyl-5-[2-(methylsulfonyl)pyrimidin-4-yl]-1H-pyrazole-3-carboxylate were dissolved in 1.5 mL of dry dioxane and 35.6 µl (0.284 mmol) of 4-amino-1-methyl-piperidine were added. The resulting suspension was heated a 150° C. for 2 h by microwave irradiation. The residue was dried and purified by flash chromatography (DCM:MeOH 9:1) to give the title compound (50%).

$^1$H NMR (600 MHz, DMSO-d$_6$) δ ppm 8.36 (d, J=4.76 Hz, 1H), 7.35 (br. s., 1H), 6.88 (br. s., 1H), 6.72 (d, J=4.76 Hz, 1H), 4.28 (q, J=7.02 Hz, 1H), 3.67 (br. s., 1H), 2.77 (d, J=10.62 Hz, 2H), 2.16 (br. s., 3H), 1.91 (m, 2H), 1.80 (br. s., 2H), 1.58-1.65 (m, 9H), 1.48-1.56 (m, 3H), 1.29 (t, J=7.05 Hz, 3H)

HRMS (ESI) calcd for $C_{20}H_{31}N_6O_2$ [M+H]$^+$ 387.2503. found 387.2503.

According to this same methodology, but employing suitable substituted derivatives, the following compounds were prepared:

Ethyl 5-[2-(phenylamino)pyrimidin-4-yl]-1H-pyrazole-3-carboxylate [(Ia) R1=phenyl, X=—NH—, R2=H, R3=COOEt, R4=H]

$^1$H NMR (600 MHz, DMSO-d$_6$) δ ppm 14.07-14.63 (m, 1H), 9.63 (s, 1H), 8.53 (br. s., 1H), 7.82 (d, J=7.69 Hz, 2H), 7.24-7.46 (m, 4H), 6.97 (t, J=7.23 Hz, 2H), 4.27-4.41 (m, 2H), 1.34 (t, J=6.78 Hz, 3H)

HRMS (ESI) calcd for $C_{16}H_{16}N_5O_2$ [M+H]$^+$ 310.1299. found 310.1293.

Ethyl 1-tert-butyl-5-[2-(phenylamino)pyrimidin-4-yl]-1H-pyrazole-3-carboxylate [(Ia) R1=phenyl, X=—NH—, R2=t-butyl, R3=COOEt, R4=H]

$^1$H NMR (600 MHz, DMSO-d$_6$) δ ppm 9.74 (s, 1H), 8.59 (d, J=4.95 Hz, 1H), 7.71 (d, J=7.88 Hz, 2H), 7.27 (t, J=7.88 Hz, 2H), 6.94-7.02 (m, 2H), 6.90 (s, 1H), 4.29 (q, J=7.14 Hz, 2H), 1.54 (s, 9H), 1.29 (t, J=7.05 Hz, 3H)

HRMS (ESI) calcd for $C_{20}H_{24}N_5O_2$ [M+H]$^+$ 366.1925. found 366.1927.

Ethyl 1-tert-butyl-5-[2-(dimethylamino)pyrimidin-4-yl]-1H-pyrazole-3-carboxylate [(Ia) R1=dimethyl, X=—NH—, R2=t-butyl, R3=COOEt, R4=H]

$^1$H NMR (600 MHz, DMSO-d$_6$) δ ppm 8.45 (d, J=4.76 Hz, 1H), 6.89 (s, 1H), 6.77 (d, J=4.76 Hz, 1H), 4.29 (q, J=7.14 Hz, 2H), 3.15 (s, 6H), 1.57-1.63 (m, 9H), 1.29 (t, J=7.14 Hz, 3H)

HRMS (ESI) calcd for $C_{16}H_{23}N_5O_2$ [M+H]$^+$ 318.1925. found 318.1934.

Ethyl 1-tert-butyl-5-[2-(propan-2-ylamino)pyrimidin-4-yl]-1H-pyrazole-3-carboxylate [(Ia) R1=isopropyl, X=—NH—, R2=t-butyl, R3=COOEt, R4=H]

$^1$H NMR (600 MHz, DMSO-d$_6$) δ ppm 8.36 (d, J=4.76 Hz, 1H), 7.49 (s, 0H), 7.25 (br. s., 1H), 6.86 (s, 1H), 6.70 (d, J=4.76 Hz, 1H), 4.28 (q, J=7.02 Hz, 2H), 4.05 (d, J=6.41 Hz, 1H), 1.56-1.62 (m, 9H), 1.29 (t, J=7.14 Hz, 3H), 1.15 (d, J=6.59 Hz, 6H)

HRMS (ESI) calcd for $C_{17}H_{25}N_5O_2$ [M+H]$^+$ 332.2081. found 332.2074.

Example 27

1-tert-butyl-5-[2-(dimethylamino)pyrimidin-4-yl]-1H-pyrazole-3-carboxamide [(Ia) R1=Me, X=—N(Me)—, R2=t-butyl, R3=CONH$_2$, R4=H] cpd 27 conv. f

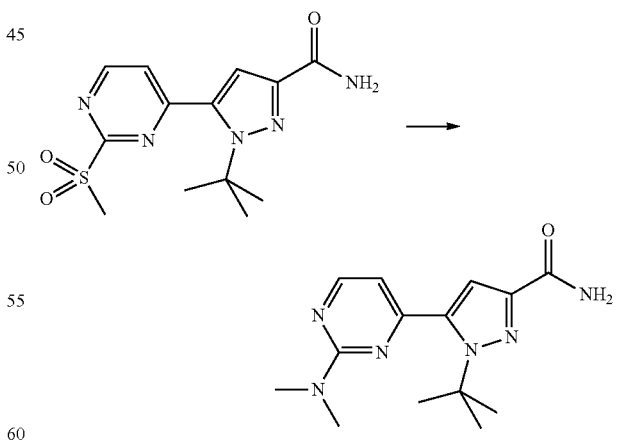

35 mg (0.108 mmol) of 1-tert-butyl-5-[2-(methylsulfonyl)pyrimidin-4-yl]-1H-pyrazole-3-carboxamide were dissolved in 1.5 mL of dimethylamine 2N in THF and the resulting solution was heated at 125° C. for 1 h by microwave irradiation. The final mixture was purified by preparative HPLC/MS to provide the title compound (33%).

$^1$H NMR (600 MHz, DMSO-$d_6$) δ ppm 8.44 (d, J=4.76 Hz, 1H), 7.44 (br. s., 1H), 7.25 (br. s., 1H), 6.76 (s, 1H), 6.74 (d, J=4.95 Hz, 1H), 3.14 (s, 6H), 1.60 (s, 9H)

HRMS (ESI) calcd for $C_{14}H_{21}N_6O$ [M+H]$^+$ 289.1772. found 289.1772.

Example 28

N-hydroxy-5-[2-(methylsulfanyl)pyrimidin-4-yl]-1H-pyrazole-3-carboxamide [(I) R1=Me, X=—S—, R2=H, R3=CONHOH, R4=H] cpd 29 conv. b

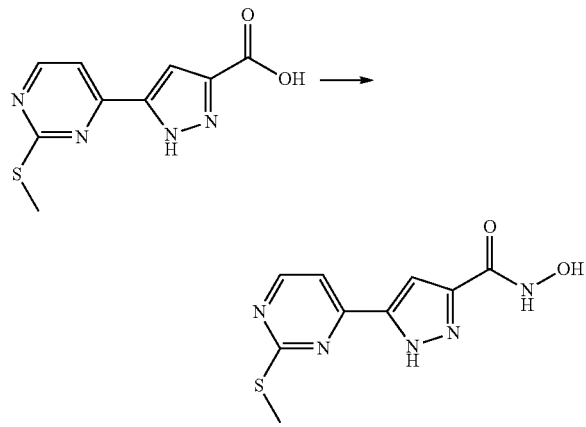

5-(2-methylsulfanyl-pyrimidin-4-yl)-1H-pyrazole-3-carboxylic acid (60 mg, 0.25 mmol) was reacted in dry DCM/DMF 9:1 mixture (2 mL) with O-(tetrahydro-2H-pyran-2-yl)hydroxylamine (44.6 mg, 0.38 mmol), EDC.HCl (73 mg, 0.38 mmol), HOBt (51.5 mg, 0.38 mmol) and DIPEA (0.087 mL, 0.51 mmol) at r.t. for 4 h. The reaction was worked up with water, NH$_4$Cl sat. sol., NaHCO$_3$ sat. sol. and extracted with AcOEt. The organic layer was washed with brine dried over Na$_2$SO$_4$, filtered and concentrated under reduced pressure. The crude was purified by silica gel flash chromatography eluting with DCM/MeOH 19/1 to provide 5-[2-(methylsulfanyl)pyrimidin-4-yl]-N-(tetrahydro-2H-pyran-2-yloxy)-1H-pyrazole-3-carboxamide 40 mg (48%) as a colorless oil.

$^1$H NMR (600 MHz, DMSO-$d_6$) δ ppm 14.24 (br.s., 1H), 11.41-12.05 (m, 1H), 8.55-8.80 (m, 1H), 7.61-7.70 (m, 1H), 7.48-7.53 (m, 1H), 4.98-5.03 (m, 1H), 5.01 (br. s., 1H), 4.01-4.14 (m, 1H), 3.51-3.61 (m, 1H), 2.59 (s, 3H), 1.32-1.80 (m, 6H)

HRMS (ESI) calcd for $C_{14}H_{18}N_5O_3S$ [M+H]$^+$ 336.1125. found 336.1131.

5-[2-(methylsulfanyl)pyrimidin-4-yl]-N-(tetrahydro-2H-pyran-2-yloxy)-1H-pyrazole-3-carboxamide (35 mg, 0.1 mmol) was reacted with 4 M HCl in dioxane (2 mL). The solution was stirred at r.t. for 20 min, then the volatiles were removed in vacuo to afford the title product (27 mg, quant.) as a white solid.

$^1$H NMR (600 MHz, DMSO-$d_6$) δ ppm 14.25 (br.s., 1H), 11.28 (br.s., 1H), 8.66 (d, J=5.13 Hz, 1H), 7.64 (d, J=5.13 Hz, 1H), 7.45 (s, 1H), 2.56-2.60 (m, 3H)

HRMS (ESI) calcd for $C_9H_{10}N_5O_2S$ [M+H]$^+$ 252.0550. found 252.0551.

Example 29

Ethyl 5-[2-(methylsulfanyl)pyrimidin-4-yl]-1H-pyrazole-3-carboxylate [(I), R1=Me, X=—S—, R2 and R4=H, R3=COOEt]

step 9

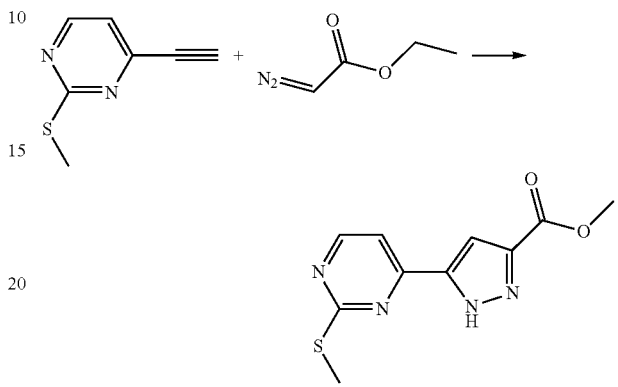

4-Ethynyl-2-(methylsulfanyl)pyrimidine (75 mg, 0.5 mmol) and ethyl diazoacetate (60 mg, 0.5 mmol) in THF (1.5 mL) were refluxed for 16 h. The solvent was removed and the residue was taken up in water. The formed precipitate was then recovered and purified on silica gel (eluant from hexane/ethylacetate 9:1 to hexane/ethylacetate 4:6) providing 40 mg of the title compound (30%).

LC/MS (254 nm) HPLC method 3: Rt 4.78 min $^1$H NMR (600 MHz, DMSO-$d_6$) δ ppm 13.94-14.66 (m, 1H), 8.68 (br. s., 1H), 7.69 (d, J=5.13 Hz, 1H), 7.5 (br. s., 1H), 4.24-4.46 (m, J=6.23 Hz, 2H), 2.56-2.63 (m, 3H), 1.33 (t, J=7.14 Hz, 3H)

HRMS (ESI) calcd for $C_{11}H_{13}N_4O_2S$ [M+H]$^+$ 265.0754. found 265.0755.

Example 30

5-(2-methoxypyrimidin-4-yl)-1H-pyrazole-3-carboxylic acid [(I) R1=Me, X=—O—, R2=H, R3=COOH, R4=H]

conv. d, conv. e

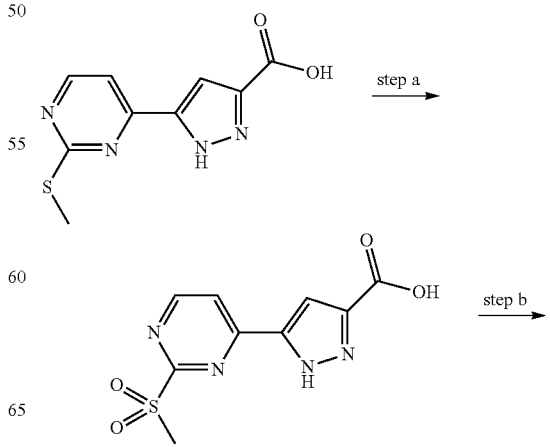

-continued

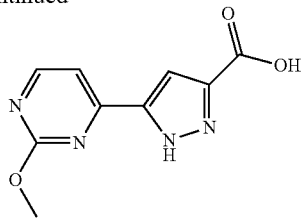

Step a: 100 mg (0.42 mmol) of 5-[2-(methylsulfanyl)pyrimidin-4-yl]-1H-pyrazole-3-carboxylic acid were dissolved in 10 mL of DCM and 291 mg (1.6 mmol) of m-chloroperbenzoic acid were added. The final suspension was stirred at r.t. for 1 h, then the reaction mixture was filtered and the solid washed twice with DCM. The solid obtained (110 mg) was an inseparable mixture of the desired product and m-chlorobenzoic acid, therefore it was used for the next step without any further treatment.

Step b: 110 mg of the previous mixture were dissolved in MeOH and stirred at 60° C. for 4 h. The volatiles were removed under vacuum and the crude purified by preparative HPLC, method 1, to provide the title compound (30 mg, 32% over two steps).

$^1$H NMR (600 MHz, DMSO-$d_6$) δ ppm 8.54 (d, J=4.95 Hz, 1H), 7.54 (d, J=5.13 Hz, 1H), 6.94 (br. s., 1H), 3.95 (s, 3H)

HRMS (ESI) calcd for $C_9H_9N_4O_3$[M+H]$^+$ 221.0669. found 221.0667.

Example 31

N-benzyl-1-tert-butyl-5-(2-phenoxypyrimidin-4-yl)-1H-pyrazole-3-carboxamide [(Ia) R1=phenyl, X=—O—, R2=t-butyl, R3=CONHR", R"=benzyl, R4=H] cpd 30 conv. c

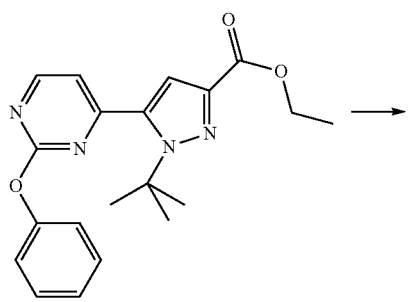

A dry microwave vessel (0.5-2 mL) was charged with a magnetic stirrer bar and benzylamine (11.7 μl, 0.11 mmol). THF (1 mL) was added along with DABAL-Me$_3$ (57.2 mg, 0.12 mmol) and ethyl 1-tert-butyl-5-(2-phenoxypyrimidin-4-yl)-1H-pyrazole-3-carboxylate (30 mg, 0.08 mmol). The microwave vial was flushed with Ar for 5 min, sealed with a microwave cap and irradiated at 130° C. for 20 min. The reaction mixture was quenched with 1M HCl (1.5 mL), extracted with DCM (3×1 mL) and with Alltech aqueous/organic separator columns, the organic layers were separated and then evaporated to yield the crude product. The product was purified using a Waters Autopurification System FractionLynx™ (HPLC/MS preparative method 2) yielding 18.6 mg of the title compound (53%).

$^1$H NMR (600 MHz, DMSO-$d_6$) δ ppm 8.79 (d, J=4.95 Hz, 1H), 8.63 (t, J=6.32 Hz, 1H), 7.49-7.52 (m, 1H), 7.41-7.47 (m, 2H), 7.29-7.34 (m, 4H), 7.25-7.28 (m, 1H), 7.20-7.25 (m, 3H), 7.00 (s, 1H), 4.43 (d, J=6.41 Hz, 2H), 1.39 (s, 9H)

HRMS (ESI) calcd for $C_{25}H_{26}N_5O_2$ [M+H]$^+$ 428.2081. found 428.2077.

According to this same methodology, but employing suitable substituted derivatives, the following compounds were prepared:

1-tert-butyl-5-(2-phenoxypyrimidin-4-yl)-N-(propan-2-yl)-1H-pyrazole-3-carboxamide [(Ia) R1=phenyl, X=—O—, R2=t-butyl, R3=CONHR", R"=—CH(CH$_3$)$_2$, R4=H] cpd 31

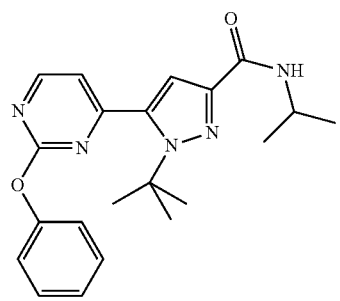 [SMILES: CC(C)NC(=O)c1cc(-c2ccnc(Oc3ccccc3)n2)n(C(C)(C)C)n1]

$^1$H NMR (600 MHz, DMSO-$d_6$) δ ppm 8.78 (d, J=4.95 Hz, 1H), 7.69 (d, J=8.24 Hz, 1H), 7.47-7.51 (m, 1H), 7.40-7.47 (m, 2H), 7.26 (t, J=7.42 Hz, 1H), 7.19-7.25 (m, 2H), 6.97 (s, 1H), 3.99-4.15 (m, 1H), 1.39 (s, 9H), 1.15 (d, J=6.59 Hz, 6H)

HRMS (ESI) calcd for $C_{21}H_{26}N_5O_2$ [M+H]$^+$ 380.2081. found 380.2076.

1-tert-butyl-5-(2-phenoxypyrimidin-4-yl)-N-phenyl-1H-pyrazole-3-carboxamide [(Ia) R1=phenyl, X=—O—, R2=t-butyl, R3=CONHR", R"=phenyl, R4=H] cpd 32

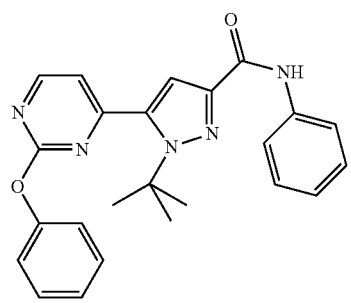 [SMILES: CC(C)(C)n1nc(C(=O)Nc2ccccc2)cc1-c1ccnc(Oc2ccccc2)n1]

$^1$H NMR (600 MHz, DMSO-$d_6$) δ ppm 9.80 (s, 1H), 8.81 (d, J=5.13 Hz, 1H), 7.76 (d, J=7.88 Hz, 2H), 7.54 (d, J=4.95 Hz, 1H), 7.43-7.48 (m, 2H), 7.34 (t, J=7.88 Hz, 2H), 7.26-7.29 (m, 1H), 7.25 (d, J=7.88 Hz, 2H), 7.14 (s, 1H), 7.10 (t, J=7.42 Hz, 1H), 1.44 (s, 9H)

HRMS (ESI) calcd for $C_{24}H_{24}N_5O_2$ [M+H]$^+$ 414.1925. found 414.1927.

1-tert-butyl-N-methyl-5-(2-phenoxypyrimidin-4-yl)-
1H-pyrazole-3-carboxamide [(Ia) R1=phenyl,
X=—O—, R2=t-butyl, R3=CONHR", R"=methyl,
R4=H] cpd 33

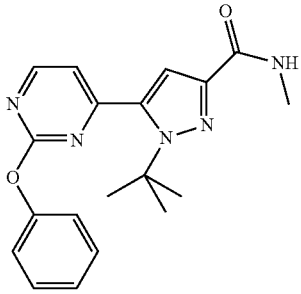 [SMILES: CNC(=O)c1cc(-c2ccnc(Oc3ccccc3)n2)n(C(C)(C)C)n1]

$^1$H NMR (600 MHz, DMSO-d$_6$) δ ppm 8.77 (d, J=5.13 Hz, 1H), 8.00 (d, J=4.64 Hz, 1H), 7.48-7.50 (m, 1H), 7.42-7.47 (m, 2H), 7.25-7.29 (m, 1H), 7.23 (d, J=8.06 Hz, 2H), 6.95 (s, 1H), 2.75 (d, J=4.76 Hz, 3H), 1.38 (s, 9H)
HRMS (ESI) calcd for C$_{19}$H$_{22}$N$_5$O$_2$ [M+H]$^+$ 352.1768. found 352.1765.

1-tert-butyl-N,N-diethyl-5-(2-phenoxypyrimidin-4-yl)-1H-pyrazole-3-carboxamide [(Ia) R1=phenyl,
X=—O—, R2=t-butyl, R3=CONR"R'",
R"=R'"=CH$_2$CH$_3$, R4=H] cpd 34

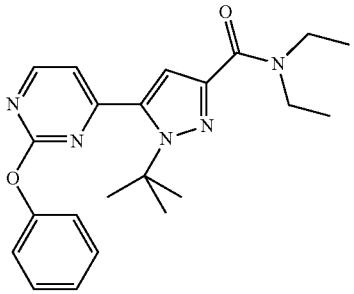 [SMILES: CCN(CC)C(=O)c1cc(-c2ccnc(Oc3ccccc3)n2)n(C(C)(C)C)n1]

$^1$H NMR (600 MHz, DMSO-d$_6$) δ ppm 8.77 (d, J=5.00 Hz, 1H), 7.49 (d, J=5.00 Hz, 1H), 7.42-7.47 (m, 2H), 7.26-7.29 (m, 1H), 7.22-7.25 (m, 2H), 6.91 (s, 1H), 3.64 (d, J=6.59 Hz, 2H), 1.37 (s, 9H), 1.19 (t, J=6.84 Hz, 3H), 1.11 (t, J=7.02 Hz, 3H)
HRMS (ESI) calcd for C$_{22}$H$_{28}$N$_5$O$_2$ [M+H]$^+$ 394.2238. found 394.2240.

1-tert-butyl-5-[2-(4-cyanophenoxy)pyrimidin-4-yl]-
N-methyl-1H-pyrazole-3-carboxamide [(Ia) R1=p-cyanophenyl, X=—O—, R2=t-butyl, R3=CONHR",
R"=Me, R4=H] cpd 35

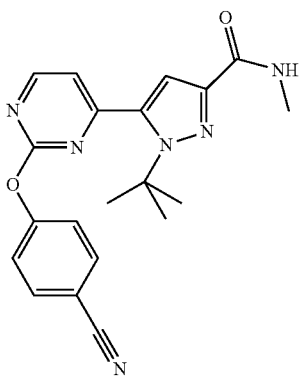 [SMILES: CNC(=O)c1cc(-c2ccnc(Oc3ccc(C#N)cc3)n2)n(C(C)(C)C)n1]

$^1$H NMR (600 MHz, DMSO-d$_6$) δ ppm 8.81 (d, J=4.95 Hz, 1H), 8.02 (d, J=4.76 Hz, 1H), 7.93-7.97 (m, 2H), 7.57 (d, J=4.95 Hz, 1H), 7.50-7.53 (m, 2H), 6.98 (s, 1H), 2.75 (d, J=4.76 Hz, 3H), 1.40 (s, 9H)
HRMS (ESI) calcd for C$_{20}$H$_{21}$N$_6$O$_2$ [M+H]$^+$ 377.1721. found 377.1711.

1-tert-butyl-5-[2-(4-cyanophenoxy)pyrimidin-4-yl]-
N-(propan-2-yl)-1H-pyrazole-3-carboxamide [(Ia)
R1=p-cyanophenyl, X=—O—, R2=t-butyl,
R3=CONHR", R"=CH(CH$_3$)$_2$, R4=H] cpd 36

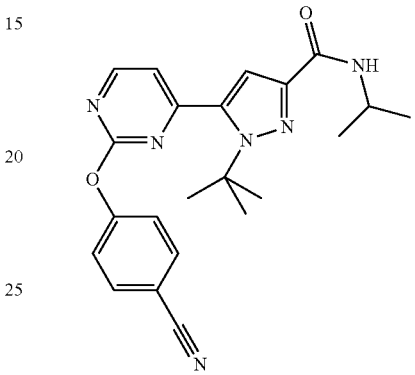

$^1$H NMR (600 MHz, DMSO-d$_6$) δ ppm 8.82 (d, J=4.95 Hz, 1H), 7.94-7.98 (m, 2H), 7.71 (d, J=8.24 Hz, 1H), 7.56 (d, J=4.95 Hz, 1H), 7.49-7.52 (m, 2H), 7.00 (s, 1H), 4.07 (td, J=6.59, 8.06 Hz, 1H), 1.39-1.42 (m, 9H), 1.16 (d, J=6.59 Hz, 6H)
HRMS (ESI) calcd for C$_{22}$H$_{25}$N$_6$O$_2$ [M+H]$^+$ 405.2034. found 405.2039.

1-tert-butyl-5-[2-(4-cyanophenoxy)pyrimidin-4-yl]-
N-phenyl-1H-pyrazole-3-carboxamide [(Ia) R1=p-cyanophenyl, X=—O—, R2=t-butyl, R3=CONHR",
R"=phenyl, R4=H] cpd 37

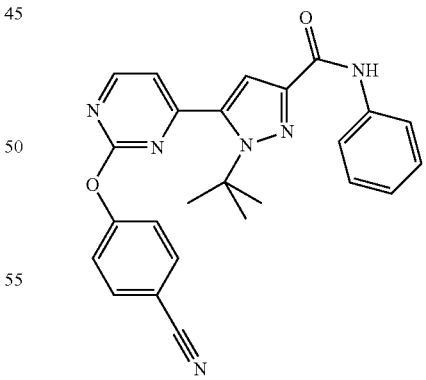

$^1$H NMR (600 MHz, DMSO-d$_6$) δ ppm 9.82 (s, 1H), 8.85 (d, J=4.95 Hz, 1H), 7.94-7.98 (m, 2H), 7.76 (d, J=7.69 Hz, 2H), 7.61 (d, J=5.13 Hz, 1H), 7.50-7.54 (m, 2H), 7.35 (t, J=7.97 Hz, 2H), 7.16 (s, 1H), 7.10 (t, J=7.33 Hz, 1H), 1.46 (s, 9H)
HRMS (ESI) calcd for C$_{25}$H$_{23}$N$_6$O$_2$ [M+H]$^+$ 439.1877. found 439.1882.

N-benzyl-1-tert-butyl-5-[2-(4-cyanophenoxy)pyrimidin-4-yl]-1H-pyrazole-3-carboxamide [(Ia) R1=p-cyanophenyl, X=—O—, R2=t-butyl, R3=CONHR", R"=benzyl, R4=H] cpd 38

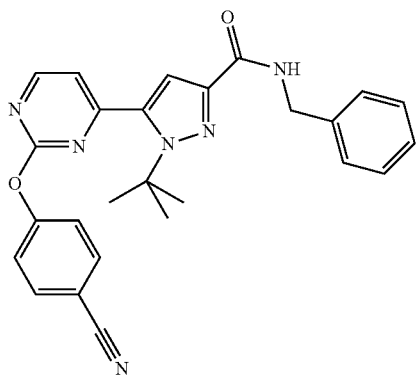 [SMILES: CC(C)(C)n1nc(C(=O)NCc2ccccc2)cc1-c1ccnc(Oc2ccc(C#N)cc2)n1]

$^1$H NMR (600 MHz, DMSO-d$_6$) δ ppm 8.82 (d, J=4.95 Hz, 1H), 8.65 (t, J=6.23 Hz, 1H), 7.92-7.98 (m, 2H), 7.58 (d, J=4.95 Hz, 1H), 7.48-7.54 (m, 2H), 7.27-7.35 (m, 4H), 7.19-7.25 (m, 1H), 7.02 (s, 1H), 4.44 (d, J=6.23 Hz, 2H), 1.41 (s, 9H)

HRMS (ESI) calcd for C$_{26}$H$_{25}$N$_6$O$_2$ [M+H]$^+$ 453.2034. found 453.2043.

1-tert-butyl-5-[2-(dimethylamino)pyrimidin-4-yl]-N-methyl-1H-pyrazole-3-carboxamide [(Ia) R1=dimethyl, X=—N—, R2=t-butyl, R3=CONHR", R"=Me, R4=H] cpd 39

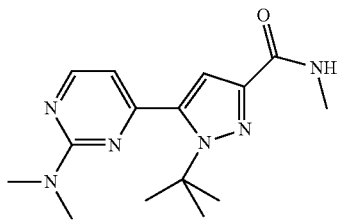

$^1$H NMR (600 MHz, DMSO-d$_6$) δ ppm 8.44 (d, J=4.88 Hz, 1H), 7.99 (d, J=4.39 Hz, 1H), 6.72-6.76 (m, 2H), 3.14 (s, 6H), 2.76 (d, J=4.76 Hz, 3H), 1.60 (s, 9H)

HRMS (ESI) calcd for C$_{15}$H$_{23}$N$_6$O [M+H]$^+$ 303.1928. found 303.1930.

1-tert-butyl-5-[2-(dimethylamino)pyrimidin-4-yl]-N-(propan-2-yl)-1H-pyrazole-3-carboxamide [(Ia) R1=methyl, X=—NR'—, R'=methyl, R2=t-butyl, R3=CONHR", R"=CH(CH$_3$)$_2$, R4=H] cpd 40

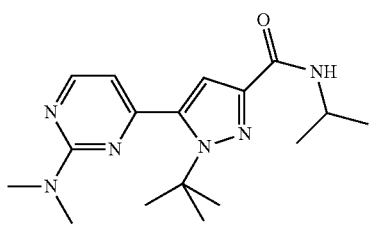 [SMILES: CC(C)NC(=O)c1cc(-c2ccnc(N(C)C)n2)n(C(C)(C)C)n1]

$^1$H NMR (401 MHz, DMSO-d$_6$) δ ppm 8.44 (d, J=4.88 Hz, 1H), 7.67 (d, J=8.42 Hz, 1H), 6.77 (s, 1H), 6.74 (d, J=4.88 Hz, 1H), 4.08 (d, J=7.81 Hz, 1H), 3.14 (s, 6H), 1.61 (s, 9H), 1.16 (s, 6H)

HRMS (ESI) calcd for C$_{17}$H$_{27}$N$_6$O [M+H]$^+$ 331.2241. found 331.2245.

1-tert-butyl-5-[2-(dimethylamino)pyrimidin-4-yl]-N-phenyl-1H-pyrazole-3-carboxamide [(Ia) R1=methyl, X=—NR'—, R'=methyl, R2=t-butyl, R3=CONHR", R"=phenyl, R4=H] cpd 41

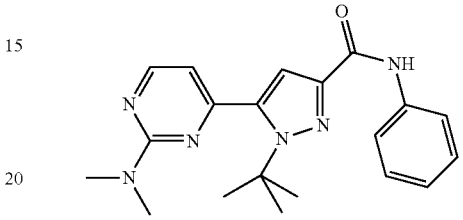

$^1$H NMR (401 MHz, DMSO-d$_6$) δ ppm 9.80 (s, 1H), 8.47 (d, J=4.88 Hz, 1H), 7.77 (d, J=8.30 Hz, 2H), 7.35 (t, J=7.87 Hz, 2H), 7.07-7.13 (m, 1H), 6.94 (s, 1H), 6.79 (d, J=4.88 Hz, 1H), 3.16 (s, 6H), 1.65 (s, 9H)

HRMS (ESI) calcd for C$_{20}$H$_{25}$N$_6$O [M+H]$^+$ 365.2085. found 365.2089.

N-benzyl-1-tert-butyl-5-[2-(dimethylamino)pyrimidin-4-yl]-1H-pyrazole-3-carboxamide [(Ia) R1=methyl, X=—NR'—, R'=methyl, R2=t-butyl, R3=CONHR", R"=benzyl, R4=H] cpd 42

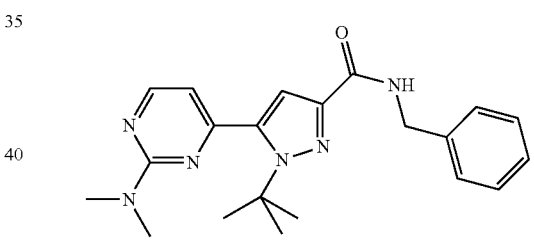

$^1$H NMR (401 MHz, DMSO-d$_6$) δ ppm 8.62 (t, J=6.35 Hz, 1H), 8.44 (d, J=4.88 Hz, 1H), 7.29-7.35 (m, 4H), 7.21-7.26 (m, 1H), 6.80 (s, 1H), 6.75 (d, J=4.88 Hz, 1H), 4.42-4.47 (m, 2H), 3.14 (s, 6H), 1.55-1.64 (m, 9H)

HRMS (ESI) calcd for C$_{21}$H$_{27}$N$_6$O [M+H]$^+$ 379.2241. found 379.2252.

1-tert-butyl-5-[2-(morpholin-4-yl)pyrimidin-4-yl]-N-phenyl-1H-pyrazole-3-carboxamide [(Ia) R1=morpholin, X=—N—, R2=t-butyl, R3=CONHR", R"=phenyl, R4=H] cpd 43

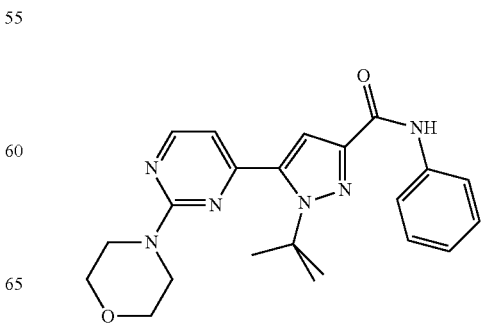

$^1$H NMR (600 MHz, DMSO-d$_6$) δ ppm 9.80 (s, 1H), 8.52 (d, J=4.95 Hz, 1H), 7.78 (d, J=7.88 Hz, 2H), 7.35 (t, J=7.88 Hz, 2H), 7.10 (t, J=7.33 Hz, 1H), 6.95 (s, 1H), 6.88 (d, J=4.94 Hz, 1H), 3.61-3.78 (m, 8H), 1.63 (s, 9H)

HRMS (ESI) calcd for C$_{22}$H$_{27}$N$_6$O$_2$ [M+H]$^+$ 407.2190. found 407.2186.

N-benzyl-1-tert-butyl-5-[2-(morpholin-4-yl)pyrimidin-4-yl]-1H-pyrazole-3-carboxamide [(Ia) R1=morpholin, X=—N—, R2=t-butyl, R3=CONHR", R"=benzyl, R4=H] cpd 44

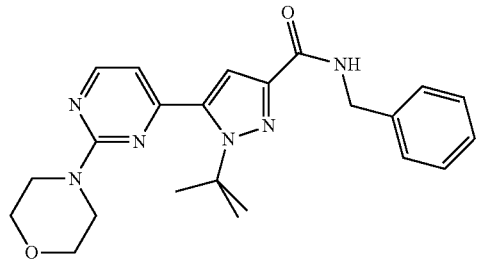 [SMILES: CC(C)(C)n1nc(C(=O)NCc2ccccc2)cc1-c1ccnc(N2CCOCC2)n1]

$^1$H NMR (600 MHz, DMSO-d$_6$) δ ppm 8.63 (t, J=6.41 Hz, 1H), 8.50 (d, J=4.95 Hz, 1H), 7.28-7.36 (m, 4H), 7.19-7.26 (m, 1H), 6.84 (d, J=4.94 Hz, 1H), 6.81 (s, 1H), 4.45 (d, J=6.23 Hz, 2H), 3.65-3.75 (m, 8H), 1.57-1.60 (m, 9H)

HRMS (ESI) calcd for C$_{23}$H$_{29}$N$_6$O$_2$ [M+H]$^+$ 421.2347. found 421.2334.

Preparation K (5-Chloro-2-ethylphenyl)boronic acid (XVIa)

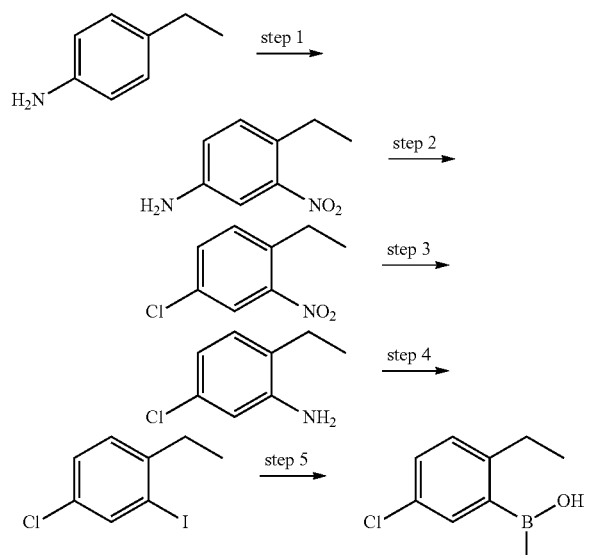

Step 1: 4-Ethyl-3-nitroaniline

4-Ethylaniline (10.3 mL, 82.5 mmol) was added dropwise to sulfuric acid (96%, 63 mL), cooled to 8° C., maintaining the temperature below 10° C. After the addition, the reaction mixture was cooled to −5° C., before the addition of a mixture of nitric acid (100%, 4 mL) and sulfuric acid (96%, 10 mL), keeping the temperature below 0° C. The reaction mixture was then stirred at the same temperature for 1 h. The reaction mixture was poured into ice (200 mL) and the precipitate filtered and washed with water. The solid was suspended with water (100 mL) and neutralized with ammonium hydroxide (35%). The precipitate was filtered and dried in the oven to obtain a light-brown solid (10 g, 73%).

$^1$H NMR (400 MHz, DMSO-d$_6$) δ ppm 1.11 (t, J=7.45 Hz, 3 H), 2.63 (q, J=7.45 Hz, 2 H), 5.53 (s, 2 H), 6.81 (dd, J=8.30, 2.44 Hz, 1 H), 7.04 (d, J=2.44 Hz, 1 H), 7.11 (d, J=8.30 Hz, 1 H)

Step 2: 4-Chloro-1-ethyl-2-nitrobenzene

A solution of sodium nitrite in water (4.2 g, 60 mmol, 5 M, 12 mL) was added dropwise to a cooled (0° C.) solution of 4-ethyl-3-nitroaniline (10 g, 60 mmol) in HCl (conc., 200 mL) and the reaction mixture was stirred at the same temperature for 1.5 h. Copper(I) chloride (9.5 g, 96 mmol) was then added and the solution was stirred at r.t. for 1 h and then at 80° C. for an additional hour. After cooling down the reaction mixture was extracted with DCM (3×100 mL) and the combined organic layers were dried over sodium sulfate. The crude was then purified by flash chromatography (hexane:AcOEt 9:1) to obtain the title compound as a yellow oil (6.28 g, 56%).

$^1$H NMR (400 MHz, DMSO-d$_6$) δ ppm 1.19 (t, J=7.45 Hz, 3 H), 2.78 (q, J=7.45 Hz, 2 H), 7.57 (d, J=8.42 Hz, 1 H), 7.74 (dd, J=8.36, 2.26 Hz, 1 H), 8.03 (d, J=2.32 Hz, 1 H).

Step 3: 5-Chloro-2-ethylaniline

A solution of hydrazine hydrate (6.95 mL, 134.7 mmol) in MeOH (50 mL) was added dropwise to a solution of 4-chloro-1-ethyl-2-nitrobenzene (6.25 g, 33.7 mmol) in MeOH (120 mL), in the presence of iron(III) chloride (547 mg, 3.4 mmol) and activated charcoal (547 mg), and the reaction mixture was stirred under reflux for 13 h. The solids were filtered over celite, the filtrate concentrated and purified by flash chromatography (hexane:AcOEt 9:1) to obtain the title compound as a light-pink oil (5.09 g, 97%).

$^1$H NMR (400 MHz, DMSO-d$_6$) δ ppm 1.09 (t, J=7.51 Hz, 3 H), 2.39 (q, J=7.49 Hz, 2 H), 5.13 (s, 2 H), 6.47 (dd, J=8.06, 2.20 Hz, 1 H), 6.62 (d, J=2.20 Hz, 1 H), 6.89 (d, J=8.06 Hz, 1 H).

Step 4: 4-Chloro-1-ethyl-2-iodobenzene

A mixture of 5-chloro-2-ethylaniline (3.35 g, 21.5 mmol), p-toluensulfonic acid (12.29 g, 64.6 mmol) and water (0.1 mL per mmol of aniline) were ground in a mortar for few minutes to obtain a homogeneous paste to which solid sodium nitrite (3.71 g, 53.8 mmol) was added and the paste was furtherly ground for 10 min. At last, solid potassium iodide (8.94 g, 53.8 mmol) was added and the paste ground for another 20 min. The paste was then dissolved in water (50 mL) and treated with sodium sulfite (10% aq. sol.) before being extracted with AcOEt (3×100 mL). The combined organic layers were dried over sodium sulfate and the crude was purified by flash chromatography (hexane) to obtain the title compound as a light-yellow oil (4.35 g, 76%).

$^1$H NMR (400 MHz, DMSO-d$_6$) δ ppm 1.12 (t, J=7.51 Hz, 3 H), 2.66 (q, J=7.53 Hz, 2 H), 7.29-7.35 (m, 1 H), 7.42 (dd, J=8.30, 2.20 Hz, 1 H), 7.87 (d, J=2.20 Hz, 1 H).

Step 5: (5-Chloro-2-ethylphenyl)boronic acid i-Propylmagnesium chloride (2 M in THF, 8.98 mL, 17.95 mmol) was added dropwise to a cooled (−30° C.) solution of 4-chloro-1-ethyl-2-iodobenzene (4.35 g, 16.3 mmol) in dry THF (40 mL) and the reaction mixture was stirred at the same temperature for 30 min, under argon. After this time, trimethylborate (3.63 mL, 32.6 mmol) was added dropwise and the reaction mixture was stirred at the same temperature for 1.5 h. HCl (1 M, 16 mL) was added and the reaction mixture extracted with AcOEt (3×50 mL). The combined organic layers were dried over sodium sulfate and, after removal of the solvent, a solid was obtained, which was triturated with hexane to obtain the title compound as a white solid (2.15 g, 72%).

$^1$H NMR (400 MHz, DMSO-d$_6$) δ ppm 1.12 (t, J=7.51 Hz, 3 H), 2.72 (q, J=7.69 Hz, 2 H), 7.17 (d, J=8.18 Hz, 1 H), 7.25-7.32 (m, 1 H), 7.36 (d, J=2.32 Hz, 1 H), 8.19 (s, 2 H).

Preparation L

4-Ethynyl-2-(methylsulfanyl)pyrimidine [(XX) R1=Me, X=—S—, R4=H]

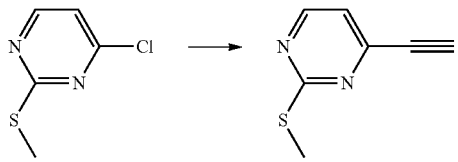

To a solution of Pd(PPh$_3$).CH$_2$Cl$_2$ (22 mg, 0.031 mmol) and PPh$_3$ (17 mg, 0.065 mmol) in THF (200 mL), TEA (300 mL), and 4-Chloro-2-methylsulfanyl-pyrimidine (1.0 g, 6.75 mmol, 1 eq.) were added under argon. CuI (13 mg, 0.065 mmol) and trimethylsilylacetylene (725 mg, 7.25 mmol, 1.1 eq) were then added sequentially. The reaction mixture was heated at reflux for 8 h and cooled to rt. The precipitate was filtered off and washed with AcOEt. The filtrate solution was concentrated and the residue was diluted with DCM and 3 g of silica gel. The solvent was removed and the residue was loaded on silica column. The product was eluted with 10% AcOEt/hexanes to provide the desilylated product (540 mg, 3.6 mmol, 53%).

LC/MS (254 nm) HPLC method 2: Rt 4.23 min $^1$H NMR (600 MHz, DMSO-d$_6$) δ ppm 8.66 (d, J=5.1 Hz, 1 H), 7.33 (d, J=5.1 Hz, 1 H), 4.77 (s, 1 H), 2.50 (s, 3 H)

HRMS (ESI) calcd for C$_7$H$_6$N$_2$S [M+H]$^+$ 151.0325. found 151.0328.

Pharmacology

The compounds of formula (I) are active as protein kinase inhibitors and are therefore useful, for instance, to restrict the unregulated proliferation of tumour cells.

In therapy, they may be used in the treatment of various tumours, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The short forms and abbreviations used herein have the following meaning:
Ci Curie
DMSO dimethylsulfoxide
KDa kiloDalton
microCi microCurie
mg milligram
microg microgram
ng nanogram
L liter
mL milliliter
μL microliter
M molar
mM millimolar
μM micromolar
nM nanomolar Biochemical Assay for Inhibitors of PIM1 Kinase Activity The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00.

The washed resin is stable for more than one week; the stock resin is kept at 4° C. before use.

ii. Kinase Buffer (KB)

The buffer for PIM1 assay was composed of HEPES 50 mM, at pH 7.5, with 10 mM MgCl$_2$, 1 mM DTT, 3 μM NaVO$_3$, and 0.2 mg/mL BSA.

Full-length human PIM1 was expressed and purified as described in Bullock A N, et al., J. Biol. Chem. 2005, 280, 41675-82.

The enzyme showed a linear kinetic after a step of pre-activation by auto-phosphorylation in the following conditions:

1.7 μM PIM1 was incubated 1 h at 28° C. in the presence of 125 μM ATP.

iii. Assay Conditions

ATP concentration: 200 μM $^{33}$P-γ-ATP: 6 nM

Enzyme concentration: 1 nM

Substrate concentration Aktide (Chemical Abstract Service Registry Number 324029-01-8): 25 μM iv. Robotized Dowex Assay The test mix consisted of:

1) 3× Enzyme mix (done in Kinase Buffer 3×), 5 μL/well
2) 3× substrate and ATP mix (done in ddH$_2$O), together with $^{33}$P-γ-ATP, 5 μL/well
3) 3× test compounds (diluted into ddH$_2$O-3% DMSO)-5 μL/well See below for compound dilution and assay scheme v. Dilution of Compounds For IC$_{50}$ determination, test compounds were received as a 1 mM solution in 100% DMSO and distributed into 96-well plates: compounds were then plated into the first column of a new 96-well plate (A1 to G1), 100 μl/well.

An automated station (Biomek FX, Beckman) was used for serial dilutions, producing 1:3 dilutions in 100% DMSO, from line A1 to A10, for all the compounds in the column. Moreover, 4-5 copies of daughter plates are prepared by reformatting 5 μL of this first set of 100% DMSO dilution plates into 384-deep well plates: one copy of these serial dilution plates with the test compounds is thawed on the day of study, reconstituted at the working concentration (3-fold the final concentration) with 162 μL/well of water and used for IC$_{50}$ determination assays. In a standard experiment, the highest concentration (3×) of compounds is typically 30 μM, while the lowest one is typically 1.5 nM. Each 384-well plate generates at least one curve of the standard inhibitor staurosporine and reference wells (total enzyme activity vs. no enzymatic activity) for evaluation of Z' and signal to background (S/B) ratio.

vi. Assay Scheme 384-well plates, V bottom (test plates) are prepared with 5 μl of compound diluted as previously described (3×) and then placed onto a PlateTrak 12 robotized station (Perkin Elmer; the robot has one 384-tip pipetting head for assay start, plus one 96-tip head for dispensing resin) together with one reservoir for Enzyme mix (3×) and one for ATP mix (3×).

Data are analyzed by an internally customized version of the "Assay Explorer" SW package, which provides sigmoidal fitting of the ten-dilution curves for IC$_{50}$ determination in secondary assay/hit confirmation routines.

Method for PIM2 Kinase Inhibition Assay: Dowex Technique i. Kinase Buffer (KB)

The buffer for PIM2 assay was composed of HEPES 50 mM, at pH 7.5, with 1 mM MgCl$_2$, 1 mM DTT, 3 μM Na$_3$VO$_4$, and 0.2 mg/mL BSA.

Full-length human PIM2 was expressed and purified as described in Fedorov O, et al., PNAS 2007 104, 51, 20523-28.

ii. Assay Conditions (Final Concentrations)

Enzyme concentration=1.5 nM

Aktide substrate (Chemical Abstract Service Registry Number 324029-01-8)=5 μM

ATP=4 μM $^{33}$P-γ-ATP=1 nM iii. Robotized Dowex Assay

See above: same procedure as described for PIM1.

Cloning, Expression and Purification of Recombinant MPS1 Full Length Protein.

MPS1 full length (corresponding to residues 2-857 of the full length sequence, see Swiss-Prot accession number P33981) was PCR amplified from the full-length human MPS1 gene present in house as clone pGEX4t_MPS1.

Amplification was performed using the forward oligonucleotide:
5'ggggacaagtttgtacaaaaaagcaggcttactggaagttctgttccaggggcccgaatccgaggatttaagtggcagag3' and the reverse oligonucleotide:
5'ggggaccactttgtacaagaaagctgggttttatttttttcccctttttttttcaaaagtcttggaggatgaag3'.

Both the oligonucleotides are described in WO2009/156315 published on 30 Dec. 2009.

For cloning purposes, the oligonucleotides included attB sites in order to obtain an attB-flanked PCR product suitable for cloning using the Gateway® technology (Invitrogen). Furthermore, for purification purposes, forward primer included a protease cleavage site. The resulting PCR product was cloned in the pDONR201 plasmid and then transferred in the baculovirus expression vector pVL1393GST (Invitrogen) Gateway®-modified. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 72 h of infection at 21° C., cells were recovered, pelletted and freezed at −80° C. For purification of recombinant protein, pellet was thawed, resuspended in lysis buffer (PBS, NaCl 150 mM, Glycerol 10%, CHAPS 0.1%, DTT 20 mM, protease and phosphatase inhibitors) and lysed by Gaulin. Lysate was cleared by centrifugation and loaded on a GST affinity column. After extensive wash, recombinant protein was cleaved by a specific protease and eluted by incubation.

To get a fully activated enzyme, the protein was then subjected to auto-phosphorylation in presence of ATP 1 mM at 25° C. for 2 h in kinase buffer (Hepes pH 7.5 50 mM, MgCl$_2$ 2.5 mM, MnCl$_2$ 1 mM, DTT 1 mM, phosphatase inhibitors); ATP was then removed with a desalting column.

Biochemical Assay for Inhibitors of MPS1 Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by β-counting.

Reagents/Assay Conditions i. Dowex Resin Preparation

See above: same procedure as described for PIM1.

ii. Kinase Buffer (KB)

The buffer for MPS1 assay was composed of HEPES 50 mM, at pH 7.5, with 2.5 mM MgCl$_2$, 1 mM MnCl$_2$, 1 mM DTT, 3 μM Na$_3$VO$_4$, 2 mM β-glycerophosphate and 0.2 mg/mL BSA.

iii. Assay Conditions

The assay was run with a final concentration MPS1 of 5 nM, in the presence of 15 μM ATP and 1.5 nM $^{33}$P-γ-ATP; the substrate was P38-tide, used at 200 μM.

iv. Robotized Dowex Assay

See above: same procedure as described for PIM1.

Compound dilution and assay scheme is defined below:

v. Dilution of Compounds

Test compounds are received as a 1 mM solution in 100% DMSO, distributed into 96 or 384 well plates:

a) for percent inhibition studies (HTS), individual dilution plates at 1 mM are diluted at a 3× concentration (30 μM) in ddH$_2$O (3% DMSO=final concentration) using a Beckman NX automated pipetting platform. The same instrument is used for distributing the diluted mother plates into the test plates.

b) for IC$_{50}$ determination (KSS platform), see above: same procedure as described for PIM1.

vi. Assay Scheme 384-well plates, V bottom (test plates) are prepared with 5 μL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 μL of ATP mix, makes an air gap inside the tips (2 μL) and aspirates 5 μL of MPS1 mix. The following dispensation into the plates allows the kinase reaction to start upon 3 cycles of mixing, done by the robot itself.

At this point, the correct concentration is restored for all reagents.

The robot incubates the plates for 60 min at r.t., and then stops the reaction by pipetting 70 μL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about 1 h in order to maximize ATP capture. At this point, 22 μL of the supernatant are transferred into 384-Optiplates (Perkin-Elmer), with 50 μL of Microscint 40 (Perkin-Elmer); after 5 min of orbital shaking the plates are read on a Perkin-Elmer Top Count radioactivity counter.

vii. Data Analysis

Data are analysed by an internally customized version of the SW package "Assay Explorer" that provides either % inhibition for primary assays or sigmoidal fittings of the ten-dilutions curves for $IC_{50}$ determination in the secondary assays/hit confirmation routines.

Biochemical Assay for Inhibitors of JAKs Kinase Activity

General Principle—Specific JAK2, JAK1 or JAK3 peptide substrates are trans-phosphorylated by JAKs kinase in the presence of ATP traced with $^{33}P$-γ-ATP. At the end of the phosphorylation reaction, the unreacted ATP, cold and radioactive, is captured by an excess of Dowex ion exchange resin that eventually settles by gravity to the bottom of the reaction plate. The supernatant is subsequently withdrawn and transferred into a counting plate that is then evaluated by β-counting.

Dowex Resin Preparation—See above: same procedure as described for PIM1.

Kinase Buffer (KB)—Kinase buffer was composed of 50 mM HEPES pH 7.5 containing 10 mM $MgCl_2$, 2.5 mM DTT, 10 μM $Na_3VO_4$ and 0.2 mg/mL BSA.

JAK2 Specific Assay Condition

Enzyme—The assay has been performed using the commercial available JAK2 kinase domain (Invitrogen, Eugene, Oreg.). The JAK2 kinase domain showed a linear kinetic without prephosphorylation.

Assay conditions—The JAK2 kinase assay was run with a final enzyme concentration of 1 nM, in the presence of 60 μM ATP, 3 nM $^{33}P$-γ-ATP and 64 μM of substrate BioDBn*306 (Aminoacid sequence: LPLDKDYYWREPGQ—SEQ ID NO: 1). The peptidic substrate was purchased from American Peptide Company (Sunnyvale, Calif.).

JAK1 Specific Assay Condition

Enzyme—The assay has been performed using JAK1 kinase domain (residues 861-1152 of the 1154 amino acid long full-length sequence, accession number P23458 of UniProtKB/Swiss-Prot database). The JAK1 kinase domain was pre-activated with ATP for 1 h at 28° C. in order to obtain a linear kinetic.

Assay conditions—The JAK1 kinase assay was run with a final pre-activated enzyme concentration of 2.5 nM, in the presence of 100 μM ATP, 2 nM $^{33}P$-γ-ATP and 154 μM of substrate BioDBn*333 (Aminoacid sequence: KKHTDDGYMPMSPGVA—SEQ ID NO: 2). The peptidic substrate was purchased from American Peptide Company (Sunnyvale, Calif.).

JAK3 Specific Assay Condition

Enzyme—The assay has been performed using the JAK3 kinase domain (residues 781-1124 of the 1124 amino acid long full-length sequence, accession number P52333 of UniProtKB/Swiss-Prot databse). The JAK3 kinase domain showed a linear kinetic without prephosphorylation.

Assay Conditions—The JAK3 kinase assay was run with a final enzyme concentration of 1 nM, in the presence of 22 μM ATP, 1 nM $^{33}P$-γ-ATP and 40 μM of substrate BioDBn*306 (Aminoacid sequence: LPLDKDYYWREPGQ—SEQ ID NO: 1). The peptidic substrate was purchased from American Peptide Company (Sunnyvale, Calif.).

Compound Dilution—For $IC_{50}$ determination, see above: same procedure as described for PIM1.

Assay Scheme—384-well plates, V bottom (test plates) are prepared with 5 μl of the compound dilution (3×) and then placed onto a PlateTrak 12 robotized station (Perkin Elmer; the robot has one 384-tip pipetting head for starting the assay plus one 96-tip head for dispensing the resin) together with one reservoir for the Enzyme mix (3×) and one for the ATP mix (3×). At the start of the run, the robot aspirates 5 μl of ATP mix, makes an air gap inside the tips (3 μl) and aspirates 5 μl of JAK2 mix. The following dispensation into the plates plus 3 cycles of mixing, done by the robot itself, starts the kinase reaction. At this point, the correct concentrations are restored for all the reagents. The robot incubates the plates for 60 min at r.t., and then stops the reaction by pipetting 60 μl of dowex resin suspension into the reaction mix. In order to avoid tip clogging, wide bore tips are used to dispense the resin suspension. Three cycles of mixing are done immediately after the addition of the resin. Another mixing cycle is performed after all the plates are stopped, this time using normal tips: the plates are then allowed to rest for about 1 h in order to allow resin sedimentation. At this point, 27 μl of the supernatant are transferred into 384-Optiplates (Perkin-Elmer), with 50 μl of Microscint 40 (Perkin-Elmer); after 5 min of orbital shaking the plates are read on a Perkin-Elmer Top Count radioactivity counter.

Data Fitting—Data are analyzed by an internally customized version of the SW package "Assay Explorer" that provides sigmoidal fitting of the ten-dilutions curves for $IC_{50}$ determination in the secondary assays/hit confirmation routines.

Representative compounds of the invention of formula (I) were tested on kinases in the specific in vitro kinase assays above described.

In particular, compounds 3, 8, 11 and 13 have an $IC_{50}$ value <0.2 μM on MPS1.

Compound 15 has $IC_{50}$ values <5 μM on JAK2 and JAK3.

Compound 21 has $IC_{50}$ values <10 μM on PIM1 and PIM2.

As can be appreciated by the skilled person, all these representative compounds have an $IC_{50}$ value <10 μM on the tested kinases, and are thus particularly advantageous in therapy against diseases caused by and/or associated with dysregulated protein kinase activity, such as cancer.

The invention claimed is:

1. A compound of formula (I):

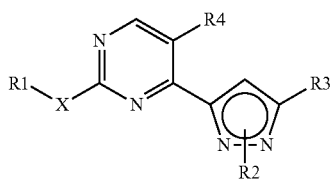

(I)

wherein

R1 is hydrogen, halogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl;

R2 is hydrogen or an optionally substituted group selected from straight or branched ($C_1$-$C_6$) alkyl, straight or branched ($C_2$-$C_6$) alkenyl, ($C_3$-$C_7$) cycloalkyl, cycloalkylalkyl, aryl, arylalkyl, heterocyclyl and heterocyclylalkyl;

R3 is a group selected from CN, —CONR"R'", —CON(OR'")R" and COOR", wherein R" and R'" are, each independently, hydrogen or an optionally substituted group selected from straight or branched ($C_1$-$C_6$) alkyl, ($C_3$-$C_7$) cycloalkyl, cycloalkyl-alkyl, aryl, arylalkyl, heterocyclyl and heterocyclylalkyl or, together with the nitrogen atom to which they are bound, R" and R'" may form a 5-to 7-membered heteroaryl or heterocyclyl group, optionally containing one additional heteroatom selected from N, O and S;

X is a single bond or a divalent radical selected from —NR'—, —O—, —S—, —SO—, —SO$_2$— and —OSO$_2$—, wherein R' is hydrogen or an optionally substituted straight or branched ($C_1$-$C_6$) alkyl, ($C_3$-$C_7$) cycloalkyl, cycloalkyl-alkyl, aryl, arylalkyl, heterocyclyl and heterocyclylalkyl or, together with the nitrogen atom to which they are bound, R' and R1 may form a 5- to 7-membered heteroaryl or heterocyclyl group optionally containing one additional heteroatom selected from N, O and S;

R4 is a group selected from hydrogen, halogen and cyano;

or a pharmaceutically acceptable salt thereof, with the proviso that the following compounds are excluded:

N-tert-butyl-1-(6-methoxypyridin-3-yl)-5-(pyrimidin-4-yl)-1H-pyrazole-3-carboxamide, methyl 1-(6-methoxypyridin-3-yl)-5-[2-(methylsulfanyl)pyrimidin-4-yl]-1H-pyrazole-3-carboxylate, methyl 1-(6-methoxypyridin-3-yl)-5-(pyrimidin-4-yl)-1H-pyrazole-3-carboxylate, 1-(6-methoxypyridin-3-yl)-5-(pyrimidin-4-yl)-1H-pyrazole-3-carboxylic acid and

[1(6-methoxypyridin-3-yl)-5-(pyrimidin-4-yl)-IH-pyrazol-3-yl](4-methylpiperazin-1-yl)methanone and with the proviso that when R3 is —CONR"R'", neither R" nor R'" are arylalkyl.

2. A compound of formula (I) as defined in claim 1 wherein:

R3 is CN, CONR"R'" or CON(OR'")R", wherein R" and R'" are as defined in claim 1.

3. A compound of formula (I) as defined in claim 1 wherein:

X is a single bond or a divalent radical selected from —NR', —O—and —S—, wherein R' is as defined in claim 1.

4. A compound of formula (I) as defined in claim 1 wherein:

R1 is hydrogen or an optionally substituted group selected from straight or branched ($C_1$-$C_6$) alkyl, aryl, arylalkyl, heterocyclyl and heterocyclylalkyl or, together with the nitrogen atom to which they are bound, R' and R1 may form a 5-to 7-membered heteroaryl or heterocyclyl group optionally containing one additional heteroatom selected from N, O and S, wherein R' is as defined in claim 1.

5. A compound of formula (I) as defined in claim 1 wherein:
R3 is CN, CONR"R'" or CONHOR'", wherein R'" is hydrogen and R" is as defined in claim 1.

6. A compound of formula (I) or a pharmaceutically acceptable salt thereof as defined in claim 1 which is selected from the group consisting of:
3-{2-[(4-bromo-2-methoxyphenyl)amino]pyrimidin-4-yl}-N-(2,6-diethylphenyl)-1-methyl-1H-pyrazole-5-carboxamide,
N-(2,6-diethylphenyl)-3-(2-{[2-methoxy-4-(4-methylpiperazin-1-yl)phenyl]amino}pyrimidin-4-yl)-1-methyl-1H-pyrazole-5-carboxamide,
N-(2,6-diethylphenyl)-5-(2-{[2-methoxy-4-(4-methylpiperazin-1-yl)phenyl]amino}pyrimidin-4-yl)-1-methyl-1H-pyrazole-3-carboxamide,
5-{2-[(4-bromo-2-methoxyphenyl)amino]pyrimidin-4-yl}-N-(2,6-diethylphenyl)-1-methyl-1H-pyrazole-3-carboxamide,
3-{2-[(4-bromo-2-methoxyphenyl)amino]pyrimidin-4-yl}-N-(2,6-diethylphenyl)-1-(4-methoxybenzyl)-1H-pyrazole-5-carboxamide,
5-{2-[(4-bromo-2-methoxyphenyl)amino]pyrimidin-4-yl}-N-(2,6-diethylphenyl)-1-(4-methoxybenzyl)-1H-pyrazole-3-carboxamide,
N-(2,6-diethylphenyl)-5-{2-[(2-methoxyphenyl)amino]pyrimidin-4-yl}-1-methyl-1H-pyrazole-3-carboxamide,
N-(2,6-diethylphenyl)-5-[2-({4-[4-(2-hydroxyethyl)piperazin-1-yl]-2-methoxyphenyl}amino)pyrimidin-4-yl]-1-methyl-1H-pyrazole-3-carboxamide,
N-(2,6-diethylphenyl)-1-(4-methoxybenzyl)-5-(2-{[2-methoxy-4-(4-methylpiperazin-1-yl)phenyl]amino}pyrimidin-4-yl)-1H-pyrazole-3-carboxamide,
N-(2,6-diethylphenyl)-1-(4-methoxybenzyl)-5-{2-[(2-methoxyphenyl)amino]pyrimidin-4-yl}-1H-pyrazole-3-carboxamide,
N-(2,6-diethylphenyl)-5-(2-{[2-methoxy-4-(4-methylpiperazin-1-yl)phenyl]amino}pyrimidin-4-yl)-1H-pyrazole-3-carboxamide,
N-(2,6-diethylphenyl)-1-(4-methoxybenzyl)-3-{2-[(2-methoxyphenyl)amino]pyrimidin-4-yl}-1H -pyrazole-5-carboxamide,
N-(2,6-diethylphenyl)-5-[2-({4-[4-(2-hydroxyethyl)piperazin-1-yl]-2-methoxyphenyl}amino)pyrimidin-4-yl]-1H-pyrazole-3-carboxamide,
N-(2,6-diethylphenyl)-5-{2-[(2-methoxyphenyl)amino]pyrimidin-4-yl}-1H-pyrazole-3-carboxamide,
3-(2-aminopyrimidin-4-yl)-1-(5-chloro-2-ethylphenyl)-1H-pyrazole-5-carboxamide,
5-(2-aminopyrimidin-4-yl)-1-(5-chloro-2-ethylphenyl)-1H-pyrazole-3-carboxamide,
5-(2-aminopyrimidin-4-yl)-1-(5-chloro-2-methylphenyl)-1H-pyrazole-3-carboxamide,
3-(2-aminopyrimidin-4-yl)-1-(5-chloro-2-methylphenyl)-1H-pyrazole-5-carboxamide,
5-[2-(methylsulfanyl)pyrimidin-4-yl]-1H-pyrazole-3-carboxamide,
1-tert-butyl-5-[2-(methylsulfanyl)pyrimidin-4-yl]-1H-pyrazole-3-carboxamide,
5-[2-(methylsulfanyl)pyrimidin-4-yl]-1-(piperidin-4-yl)-1H-pyrazole-3-carboxamide,
3-[2-(methylsulfanyl)pyrimidin-4-yl]-1-(piperidin-4-yl)-1H-pyrazole-5-carboxamide,
3-(2-hydroxypyrimidin-4-yl)-1-(3-methoxybenzyl)-1H-pyrazole-5-carboxamide,
1-(3-methoxybenzyl)-3-(2-methylpyrimidin-4-yl)-1H-pyrazole-5-carboxamide,
1-tert-butyl-5-(2-phenylpyrimidin-4-yl)-1H-pyrazole-3-carboxamide,
1-tert-butyl-5-{2[4-(piperazin-1-yl)phenoxy]pyrimidin-4-yl}-1H-pyrazole-3-carboxamide,
1-tert-butyl-5-[2-(dimethylamino)pyrimidin-4-yl]-1H-pyrazole-3-carboxamide,
1-tert-butyl-5-(2-methoxypyrimidin-4-yl)-1H-pyrazole-3-carboxamide,
N-hydroxy-5-[2-(methylsulfanyl)pyrimidin-4-yl]-1H-pyrazole-3-carboxamide,
N-benzyl-1-tert-butyl-5-(2-phenoxypyrimidin-4-yl)-1H-pyrazole-3-carboxamide,
1-tert-butyl-5-(2-phenoxypyrimidin-4-yl)-N-(propan-2-yl)-1H-pyrazole-3-carboxamide,
1-tert-butyl-5-(2-phenoxypyrimidin-4-yl)-N-phenyl-1H-pyrazole-3-carboxamide,
1-tert-butyl-N-methyl-5-(2-phenoxypyrimidin-4-yl)-1H-pyrazole-3-carboxamide,
1-tert-butyl-N,N-diethyl-5-(2-phenoxypyrimidin-4-yl)-1H-pyrazole-3-carboxamide,
1-tert-butyl-5-[2-(4-cyanophenoxy)pyrimidin-4-yl]-N-methyl-1H-pyrazole-3-carboxamide,
1-tert-butyl-5-[2-(4-cyanophenoxy)pyrimidin-4-yl]-N-(propan-2-yl-1H-pyrazole-3-carboxamide,
1-tert-butyl-5-[2-(4-cyanophenoxy)pyrimidin-4-yl]-N-phenyl-1H-pyrazole-3-carboxamide,
N-benzyl-1-tert-butyl-5-[2-(4-cyanophenoxy)pyrimidin-4-yl]-1H-pyrazole-3-carboxamide,
1-tert-butyl-5-[2-(dimethylamino)pyrimidin-4-yl]-N-methyl-1H-pyrazole-3-carboxamide,
1-tert-butyl-5-[2-(dimethylamino)pyrimidin-4-yl]-N-(propan-2-yl)-1H-pyrazole-3-carboxamide,
1-tert-butyl-5-[2-(dimethylamino)pyrimidin-4-yl]-N-phenyl-1H-pyrazole-3-carboxamide,
N-benzyl-1-tert-butyl-5-[2-(dimethylamino)pyrimidin-4-yl]-1H-pyrazole-3-carboxamide,
1-tert-butyl-5-[2-(morpholin-4-yl)pyrimidin-4-yl]-N-phenyl-1H-pyrazole-3-carboxamide and
N-benzyl-1-tert-butyl-5-[2-(morpholin-4-yl)pyrimidin-4-yl]-1H-pyrazole-3-carboxamide.

7. A process for preparing a compound of formula (I) as defined in claim 1 or the pharmaceutically acceptable salts thereof, characterized in that the process comprises the following steps:
st. 5) mixing the compound of formula (IV)

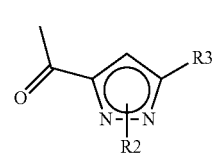

(IV)

wherein R2 is as defined in claims 1 and R3 is a group selected from —CONR"R'" and COOR5, wherein R5 is an optionally substituted ($C_1$-$C_6$) alkyl and R" and R'" are as defined in claim 1, with dimethylformamide-dialkylacetale;

st. 6) reacting the resultant compound of formula (VI)

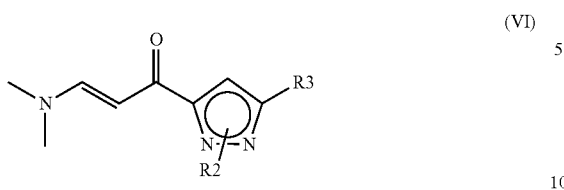

wherein R2 and R3 are as defined above, with a compound of formula (VII):

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; and X is a single bond or a divalent radical selected from —NR'—, —O— and —S—, wherein R' is as defined in claim 1, so as to obtain a compound of formula (I)

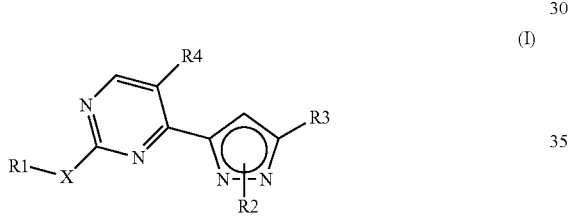

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; X is a single bond or a divalent radical selected from —NR'—, —O— and —S—, wherein R' is as defined in claim 1; R2 is as defined in claim 1; R3 is a group selected from —CONR"R'" and COOR5, wherein R5 is an optionally substituted ($C_1$-$C_6$) alkyl and R" and R'" are as defined in claims 1; and R4 is hydrogen;
or in alternative
st. 7) reacting a compound of formula (VIII):

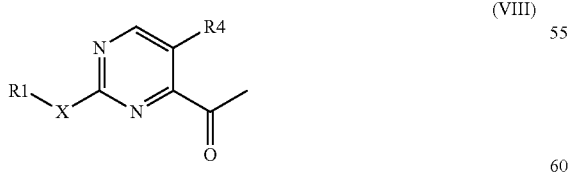

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; X is a single bond or a divalent radical, the divalent radical selected from the group consisting of —NR'—, —O— and —S—,
wherein R' is as defined in claims 1; and R4 is as defined in claim 1, with a compound of formula (IX):

wherein R3 is COOR5, wherein R5 is as defined in claim 1;
st. 8) reacting the resultant compound of formula (X)

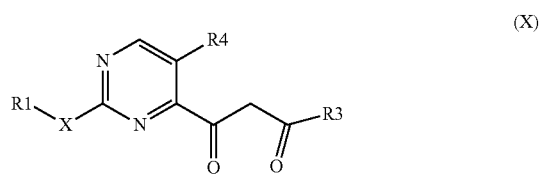

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; X is a single bond or a divalent radical, the divalent radical selected from the group consisting of —NR'—, —O— and —S—, wherein R' is as defined above, R3 is —COOR5, wherein R5 is an optionally substituted ($C_1$-$C_6$) alkyl, and R4 is as defined in claim 1, with a compound of formula (XI) or a salt therof:

R2-NHNH$_2$ (XI)

wherein R2 is as defined in claim 1, so as to obtain a compound of formula (I)

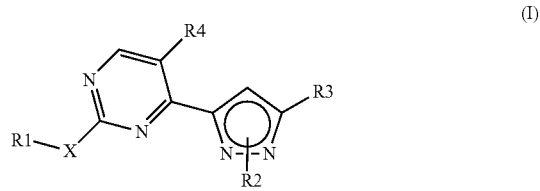

wherein R1 is hydrogen or an optionally substituted group selected from amino, straight or branched ($C_1$-$C_6$) alkyl, ($C_3$-$C_7$) cycloalkyl, cycloalkyl-alkyl, aryl, arylalkyl, heterocyclyl and heterocyclylalkyl; X is a single bond or a divalent radical, the divalent radical selected from the group consisting of —NR'—, —O— and —S—, wherein R' is as defined in claim 1; R2 is as defined in claim 1; R3 is —COOR5, wherein R5 is an optionally substituted ($C_1$-$C_6$) alkyl; and R4 is as defined in claim 1;
or, in alternative,
st. 9) reacting a compound of formula (XX):

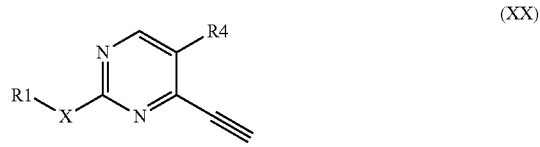

wherein R1 is as defined in claim 1; X is a single bond or a divalent radical selected from —NR'—, —O— and —S—, wherein R' is as defined in claims 1; and R4 is as defined in claim 1, with a compound of formula (III):

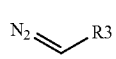
(III)

wherein R3 is —COOR5 or —CONR"R'", wherein R5 is an optionally substituted ($C_1$-$C_6$) alkyl and R' and R" are as defined in claim 1, so as to obtain a compound of formula (I)

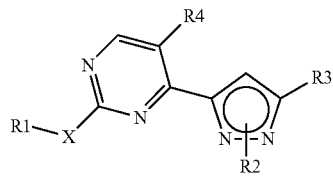
(I)

wherein R1 is as defined in claim 1; X is a single bond or a divalent radical selected from —NR'—, —O— and —S—, wherein R' is as defined in claim 1; R2 is hydrogen; R3 is —COOR5 or —CONR"R'", wherein R5 is an optionally substituted ($C_1$-$C_6$) alkyl and R' and R'" are as defined in claims 1;
and R4 is as defined in claim 1.

8. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

9. A pharmaceutical composition according to claim 8 further comprising one or more chemotherapeutic agents.

* * * * *

SEQUENCE LISTING

<160> NUMBER OF SEQ ID NOS: 2

<210> SEQ ID NO 1
<211> LENGTH: 15
<212> TYPE: PRT
<213> ORGANISM: Artificial
<220> FEATURE:
<223> OTHER INFORMATION: peptide substrate

<400> SEQUENCE: 1

Leu Pro Leu Asp Lys Asp Tyr Tyr Val Val Arg Glu Pro Gly Gln
1               5                   10                  15

<210> SEQ ID NO 2
<211> LENGTH: 16
<212> TYPE: PRT
<213> ORGANISM: Artificial
<220> FEATURE:
<223> OTHER INFORMATION: Peptide substrate

<400> SEQUENCE: 2

Lys Lys His Thr Asp Asp Gly Tyr Met Pro Met Ser Pro Gly Val Ala
1               5                   10                  15